United States Patent
Uchikawa et al.

(10) Patent No.: US 8,247,429 B2
(45) Date of Patent: Aug. 21, 2012

(54) TRICYCLIC COMPOUND AND PHARMACEUTICAL USE THEREOF

(75) Inventors: Osamu Uchikawa, Osaka (JP); Tatsuki Koike, Osaka (JP); Takafumi Takai, Osaka (JP); Yasutaka Hoashi, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 448 days.

(21) Appl. No.: 12/448,366

(22) PCT Filed: Dec. 27, 2007

(86) PCT No.: PCT/JP2007/075159
§ 371 (c)(1),
(2), (4) Date: Jun. 18, 2009

(87) PCT Pub. No.: WO2008/084717
PCT Pub. Date: Jul. 17, 2008

(65) Prior Publication Data
US 2010/0010038 A1    Jan. 14, 2010

(30) Foreign Application Priority Data
Dec. 28, 2006    (JP) .................................. 2006-356344

(51) Int. Cl.
*A61K 31/437* (2006.01)
*A61K 31/416* (2006.01)
*C07D 235/02* (2006.01)

(52) U.S. Cl. .......... 514/292; 514/294; 514/396; 546/80; 548/302.1

(58) Field of Classification Search ............ 546/80; 548/302.1; 514/292, 294, 396
See application file for complete search history.

(56) References Cited

U.S. PATENT DOCUMENTS

| | | | |
|---|---|---|---|
| 6,034,239 | A | 3/2000 | Ohkawa et al. |
| 6,218,429 | B1 | 4/2001 | Ohkawa et al. |
| 6,235,789 | B1 | 5/2001 | Ohkawa et al. |
| 6,423,870 | B1 | 7/2002 | Langlois et al. |

FOREIGN PATENT DOCUMENTS

| | | |
|---|---|---|
| JP | 8-134030 | 5/1996 |
| JP | 10-287665 | 10/1998 |
| JP | 2007/148808 | 12/2007 |
| WO | 97/32871 | 9/1997 |
| WO | 2008/069311 | 6/2008 |

OTHER PUBLICATIONS

Dorwald F. A. Side Reactions in Organic Synthesis, 2005, Wiley: VCH, Weinheim p. IX of Preface.*
International Search Report issued Feb. 19, 2008 in the International (PCT) Application of which the present application is the U.S. National Stage.

* cited by examiner

*Primary Examiner* — Rita Desai
(74) *Attorney, Agent, or Firm* — Wenderoth, Lind & Ponack, L.L.P.

(57) ABSTRACT

The present invention provides a compound represented by the formula

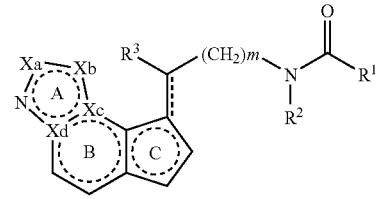

wherein $R^1$ is a hydrocarbon group optionally having substituent(s), amino optionally having substituent(s), hydroxy optionally having a substituent or a heterocyclic group optionally having substituent(s), $R^2$ is a hydrogen atom or a hydrocarbon group optionally having substituent(s), $R^3$ is a hydrogen atom, a halogen atom, a hydrocarbon group optionally having substituent(s), amino optionally having substituent(s), hydroxy optionally having a substituent or mercapto optionally having a substituent, Xa, Xb, Xc and Xd are each a carbon atom or a nitrogen atom, provided that any one or two of Xa, Xb, Xc and Xd is/are nitrogen atom(s), m is 0 to 2, and rings A to C are each a ring optionally having substituent(s), or a salt thereof, which is useful as an agent for the prophylaxis or treatment of a disease relating to an action of melatonin, and the like.

10 Claims, No Drawings

```
SEQUENCE LISTING

<160> NUMBER OF SEQ ID NOS: 2

<210> SEQ ID NO 1
<211> LENGTH: 1053
<212> TYPE: DNA
<213> ORGANISM: Homo sapiens

<400> SEQUENCE: 1
atgcagggca acggcagcgc gctgcccaac gcctcccagc ccgtgctccg cggggacggc      60
gcgcggccct cgtggctggc gtccgccctg gcctgcgtcc tcatcttcac catcgtggtg     120
gacatcctgg gcaacctcct ggtcatcctg tcggtgtatc ggaacaagaa gctcaggaac     180
gcaggaaaca tctttgtggt gagcttagcg gtggcagacc tggtggtggc catttatccg     240
```

```
tacccgttgg tgctgatgtc gatatttaac aacgggtgga acctgggcta tctgcactgc      300
caagtcagtg ggttcctgat gggcctgagc gtcatcggct ccatattcaa catcaccggc      360
atcgccatca accgctactg ctacatctgc cacagtctca agtacgacaa actgtacagc      420
agcaagaact ccctctgcta cgtgctcctc atatggctcc tgacgctggc ggccgtcctg      480
cccaacctcc gtgcagggac tctccagtac gacccgagga tctactcgtg caccttcgcc      540
cagtccgtca gctccgccta caccatcgcc gtggtggttt tccacttcct cgtccccatg      600
atcatagtca tcttctgtta cctgagaata tggatcctgg ttctccaggt cagacagagg      660
gtgaaacctg accgcaaacc caaactgaaa ccacaggact tcaggaattt tgtcaccatg      720
tttgtggttt ttgtcctttt tgccatttgc tgggctcctc tgaacttcat ggcctggcc      780 gtggcctctg accccgccag catggtgcct aggatcccag agtggctgtt tgtggccagt      840
tactacatgg cgtatttcaa cagctgcctc aatgccatta tatacgggct actgaaccaa      900
aatttcagga aggaatacag gagaattata gtctcgctct gtacagccag ggtgttcttt      960
gtggacagct ctaacgacgt ggccgatagg gttaaatgga aaccgtctcc actgatgacc     1020
aacaataatg tagtaaaggt ggactccgtt taa                                  1053

<210> SEQ ID NO 2
<211> LENGTH: 1089
<212> TYPE: DNA
<213> ORGANISM: Homo sapiens

<400> SEQUENCE: 2
atgtcagaga acggctcctt cgccaactgc tgcgaggcgg gcgggtgggc agtgcgcccg       60
ggctggtcgg gggctggcag cgcgcggccc tccaggaccc ctcgacctcc ctgggtggct      120
ccagcgctgt ccgcggtgct catcgtcacc accgccgtgg acgtcgtggg caacctcctg      180
gtgatcctct ccgtgctcag gaaccgcaag ctccggaacg caggtaattt gttcttggtg      240
agtctggcat tggctgacct ggtggtggcc ttctacccct acccgctaat cctcgtggcc      300
atcttctatg acggctgggc cctggggag gagcactgca aggccagcgc ctttgtgatg      360
ggcctgagcg tcatcggctc tgtcttcaat atcactgcca tcgccattaa ccgctactgc      420
tacatctgcc acagcatggc ctaccaccga atctaccggc gctggcacac ccctctgcac      480
atctgcctca tctggctcct caccgtggtg gccttgctgc caacttcttc tgtgggtcc      540 ctggagtacg acccacgcat ctattcctgc accttcatcc agaccgccag cacccagtac      600
acggcggcag tggtggtcat ccacttcctc ctccctatcg ctgtcgtgtc cttctgctac      660
ctgcgcatct gggtgctggt gcttcaggcc cgcaggaaag ccaagccaga gagcaggctg      720
tgcctgaagc ccagcgactt gcggagcttt ctaaccatgt ttgtggtgtt tgtgatcttt      780
gccatctgct gggctccact taactgcatc ggcctcgctg tggccatcaa ccccaagaa      840 atggctcccc agatccctga ggggctattt gtcactagct acttactggc ttatttcaac      900
agctgcctga atgccattgt ctatgggctc ttgaaccaaa acttccgcag ggaatacaag      960
aggatcctct ggccctttg aaccccacgg cactgcattc aagatgcttc caagggcagc     1020
cacgcggagg ggctgcagag cccagctcca cccatcattg gtgtgcagca ccaggcagat     1080
gctctctag                                                             1089
```

TRICYCLIC COMPOUND AND PHARMACEUTICAL USE THEREOF

This application is a U.S. national stage of International Application No. PCT/JP2007/075159 filed Dec. 27, 2007.

TECHNICAL FIELD

The present invention relates to a tricyclic compound having superior affinity for melatonin receptor, and useful as an agent for the prophylaxis or treatment of a disease related to the action of melatonin.

BACKGROUND OF THE INVENTION

Melatonin (N-acetyl-5-methoxytryptamine), which is a hormone synthesized and secreted principally in the pineal gland, increases in dark environments and decreases in light environments. Melatonin acts suppressively on pigment cells and the female gonads, and acts as a synchronous factor of biological clock while taking part in transmittance of photoperiodic code. Therefore, melatonin is expected to be usable for the treatment of diseases related to melatonin activity, such as reproductive and endocrinic disorders, sleep-awake rhythm disorders, jet-lag syndrome, various disorders related to aging and the like. It has been clarified that the production amount of melatonin decreases with aging and there is a report documenting that retention of the production amount of melatonin could prevent aging itself [Ann. N.Y. Acad. Sci., vol. 719, pages 456-460, (1994) (non-patent document 1)]. However, since melatonin is easily metabolized by metabolic enzymes in vivo [Clinical Examinations, vol. 38, No. 11, pages 282-284 (1994) (non-patent document 2)]. Therefore, melatonin is not entirely suitable as a drug.

WO 97/32871 (patent document 1) and U.S. Pat. No. 6,034,239 (patent document 2) disclose a compound represented by the formula:

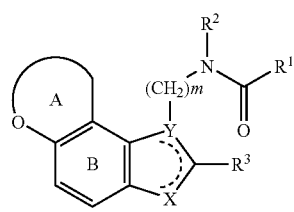

wherein $R^1$ represents an optionally substituted hydrocarbon group, optionally substituted amino or an optionally substituted heterocyclic group; $R^2$ represents a hydrogen atom or an optionally substituted hydrocarbon group; $R^3$ represents a hydrogen atom, an optionally substituted hydrocarbon group or an optionally substituted heterocyclic group; X represents $CHR^4$, $NR^4$, O or S wherein $R^4$ represents a hydrogen atom or an optionally substituted hydrocarbon group; Y represents C, CH or N, provided that when X is $CH_2$, Y is C or CH; ------ is a single bond or a double bond, ring A represents an optionally substituted 5- to 7-membered oxygen-containing heterocyclic ring; ring B represents an optionally substituted benzene ring; and m represents an integer of 1 to 4, or a salt thereof and the like, which has an affinity for melatonin receptor and is useful as a therapeutic agent for sleep disorder and the like.
patent document 1: WO 97/32871
patent document 2: U.S. Pat. No. 6,034,239 non-patent document 1: Ann. N.Y. Acad. Sci., vol. 719, pages 456-460 (1994)

non-patent document 2: Clinical Examinations, vol. 38, No. 11, pages 282-284 (1994)

DISCLOSURE OF THE INVENTION

Melatonin receptor agonists having different structures from that of melatonin, and having superior affinity for melatonin receptor, superior intracerebral mobility and superior metabolic stability are expected to be more effective for the treatment of sleep disorder and the like than melatonin. While the above-mentioned compounds and the like have been reported as melatonin receptor agonists, the development of a novel compound, which is different from the above-mentioned known compounds in the chemical structure, has superior agonistic activity for melatonin receptor, and is useful as a pharmaceutical product, is desired.

The present inventors have conducted various studies and first succeeded in the production of a novel compound represented by the following formula (I) and a salt thereof. They have further found that the compound and a salt thereof unexpectedly have superior properties as melatonin agonists and are useful as pharmaceutical agents and, based on these findings, completed the present invention.

Accordingly, the present invention relates to

[1] a compound represented by the formula:

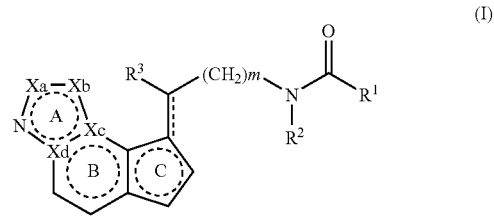

wherein $R^1$ is a hydrocarbon group optionally having substituent(s), amino optionally having substituent(s), hydroxy optionally having a substituent or a heterocyclic group optionally having substituent(s), $R^2$ is a hydrogen atom or a hydrocarbon group optionally having substituent(s), $R^3$ is a hydrogen atom, a halogen atom, a hydrocarbon group optionally having substituent(s), amino optionally having substituent(s), hydroxy optionally having a substituent or mercapto optionally having a substituent, Xa, Xb, Xc and Xd are each a carbon atom or a nitrogen atom, provided that any one or two of Xa, Xb, Xc and Xd is/are nitrogen atom(s), m is 0, 1 or 2, ring A is a 5-membered ring optionally having substituent(s), ring B is a 6-membered ring optionally having substituent(s), ring C is a 5-membered ring optionally having substituent(s), and ------ is a single bond or a double bond, or a salt thereof (hereinafter sometimes to be abbreviated as compound (I));

[2] the compound of the aforementioned [1], wherein the tricycle consisting of ring A, ring B and ring C is a ring represented by the formula

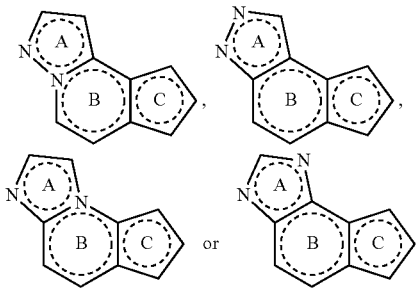

wherein each symbol is as defined in the aforementioned [1];
[3] the compound of the aforementioned [1], wherein $R^1$ is $C_{1-6}$ alkyl optionally having substituent(s), $C_{3-6}$ cycloalkyl optionally having substituent(s), $C_{2-6}$ alkenyl optionally having substituent(s) or $C_{1-6}$ alkoxy optionally having substituent(s);
[4] the compound of the aforementioned [1], wherein $R^2$ is a hydrogen atom or $C_{1-6}$ alkyl optionally having substituent(s);
[5] the compound of the aforementioned [1], wherein $R^3$ is a hydrogen atom or $C_{1-6}$ alkyl optionally having substituent(s);
[6] the compound of the aforementioned [1], wherein m is 1;
[7] the compound of the aforementioned [1], wherein ring A is a 5-membered ring optionally having 1 or 2 substituents selected from a halogen atom, a hydrocarbon group optionally having substituent(s), amino optionally having substituent(s), hydroxy optionally having a substituent and mercapto optionally having a substituent;
[8] the compound of the aforementioned [1], wherein ring B is a 6-membered ring optionally having 1 or 2 substituents selected from a halogen atom, a hydrocarbon group optionally having substituent(s), amino optionally having substituent(s), hydroxy optionally having a substituent and mercapto optionally having a substituent;
[9] the compound of the aforementioned [1], wherein ring C is a 5-membered ring optionally having 1 or 2 substituents selected from a halogen atom, a hydrocarbon group optionally having substituent(s), hydroxy optionally having a substituent and a heterocyclic group optionally having substituent(s);
[10] the compound of the aforementioned [1], wherein $R^1$ is $C_{1-6}$ alkyl, $C_{3-6}$ cycloalkyl or $C_{1-6}$ alkoxy;
$R^2$ is a hydrogen atom;
$R^3$ is a hydrogen atom;
m is 1;
ring A is a 5-membered ring optionally having 1 or 2 substituents selected from a halogen atom, $C_{1-6}$ alkyl, $C_{6-10}$ aryl and $C_{1-6}$ alkoxy-carbonyl;
ring B is a 6-membered ring optionally having one halogen atom;
ring C is an unsubstituted 5-membered ring;
Xa is (1) CH optionally substituted by $C_{1-6}$ alkyl or $C_{6-10}$ aryl or (2) NH optionally substituted by $C_{1-6}$ alkyl;
Xb is (1) CH optionally substituted by a halogen atom, $C_{1-6}$ alkyl or $C_{1-6}$ alkoxy-carbonyl or (2) NH optionally substituted by $C_{1-6}$ alkyl;
Xc is C or N; and
Xd is C or N;

[11] N-[2-(2-methyl-6,7-dihydrocyclopenta[e]indazol-8 (2H)-ylidene)ethyl]acetamide,
N-[2-(2-methyl-2,6,7,8-tetrahydrocyclopenta[e]indazol-8-yl)ethyl]acetamide,
N-[2-(2-methyl-2,6,7,8-tetrahydrocyclopenta[e]indazol-8-yl)ethyl]propanamide,
N-[2-(1-fluoro-2-methyl-2,6,7,8-tetrahydrocyclopenta[e]indazol-8-yl)ethyl]acetamide,
N-[2-(1-chloro-2-methyl-2,6,7,8-tetrahydrocyclopenta[e]indazol-8-yl)ethyl]acetamide,
N-[2-(5-fluoro-2-methyl-2,6,7,8-tetrahydrocyclopenta[e]indazol-8-yl)ethyl]acetamide,
N-[2-(5-chloro-2-methyl-2,6,7,8-tetrahydrocyclopenta[e]indazol-8-yl)ethyl]acetamide,
N-[2-(2-methyl-8,9-dihydro-7H-cyclopenta[c]pyrazolo[1,5-a]pyridin-9-yl)ethyl]acetamide,
N-[2-(2-methyl-8,9-dihydro-7H-cyclopenta[c]pyrazolo[1,5-a]pyridin-9-yl)ethyl]propanamide, or
N-[2-(2-methyl-7,8-dihydro-6H-cyclopenta[e]imidazo[1,2-a]pyridin-8-yl)ethyl]acetamide, or a salt thereof;
[12] a prodrug of the compound of the aforementioned [1];
[13] a pharmaceutical composition comprising the compound of the aforementioned [1] or a prodrug thereof;
[14] the pharmaceutical composition of the aforementioned [13], which is a melatonin receptor agonist;
[15] the pharmaceutical composition of the aforementioned [13], which is an agent for the prophylaxis or treatment of sleep disorder;
[16] a compound represented by the formula

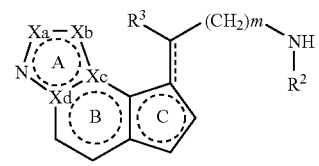

wherein
$R^2$ is a hydrogen atom or a hydrocarbon group optionally having substituent(s),
$R^3$ is a hydrogen atom, a halogen atom, a hydrocarbon group optionally having substituent(s), amino optionally having substituent(s), hydroxy optionally having a substituent or mercapto optionally having a substituent,
Xa, Xb, Xc and Xd are each a carbon atom or a nitrogen atom, provided that any one or two of Xa, Xb, Xc and Xd is/are nitrogen atom(s),
m is 0, 1 or 2,
ring A is a 5-membered ring optionally having substituent(s),
ring B is a 6-membered ring optionally having substituent(s),
ring C is a 5-membered ring optionally having substituent(s), and
------ is a single bond or a double bond,
or a salt thereof;
[17] a method for preventing or treating sleep disorder in a mammal, comprising administering an effective amount of the compound of the aforementioned [1] or a salt thereof or a prodrug thereof to the mammal;
[18] use of the compound of the aforementioned [1] or a salt thereof or a prodrug thereof for producing an agent for the prophylaxis or treatment of sleep disorder, and the like.

Since compound (I) shows superior affinity for melatonin receptors, superior pharmacokinetics (e.g., metabolic stability) and the like, a clinically useful agent for the prophylaxis or treatment of diseases related to the action of melatonin in the living body can be provided.

As the "halogen atom" used in the present specification, fluorine, chlorine, bromine or iodine can be mentioned.

As the "hydrocarbon group" of the term "hydrocarbon group optionally having substituent(s)" used in the present specification, for example, aliphatic hydrocarbon group, monocyclic saturated hydrocarbon group and aromatic hydrocarbon group and the like can be mentioned, with preference given to those having 1 to 16 carbon atoms. Specifically, for example, alkyl, alkenyl, alkynyl, cycloalkyl, aryl and the like are used.

The "alkyl" is preferably, for example, lower alkyl or the like, and, for example, $C_{1-6}$ alkyl such as methyl, ethyl, propyl, isopropyl, butyl, isobutyl, sec-butyl, tert-butyl, pentyl, hexyl etc., and the like are widely used.

The "alkenyl" is preferably, for example, lower alkenyl or the like, and, for example, $C_{2-6}$ alkenyl such as vinyl, 1-propenyl, allyl, isopropenyl, butenyl, isobutenyl etc., and the like are widely used.

The "alkynyl" is preferably, for example, lower alkynyl or the like, and, for example, $C_{2-6}$ alkynyl such as ethynyl, propargyl, 1-propynyl etc., and the like are widely used.

The "cycloalkyl" is preferably, for example, lower cycloalkyl or the like, and, for example, $C_{3-6}$ cycloalkyl such as cyclopropyl, cyclobutyl, cyclopentyl and cyclohexyl, and the like are widely used.

The "aryl" is preferably, for example, $C_{6-14}$ aryl such as phenyl, 1-naphthyl, 2-naphthyl, biphenylyl, 2-anthryl etc., or the like, more preferably $C_{6-10}$ aryl, and, for example, phenyl and the like are widely used.

As the substituent which the "hydrocarbon group" of the "hydrocarbon group optionally having substituent(s)" may have, for example, (1) halogen atom (e.g., fluorine, chlorine, bromine, iodine),
(2) nitro,
(3) cyano,
(4) hydroxy,
(5) lower alkyl optionally having substituent(s) (e.g., $C_{1-6}$ alkyl optionally having 1 to 5 substituents selected from a halogen atom, nitro, cyano, hydroxy, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, isobutyl, sec-butyl, tert-butyl, 4,4,4-trifluorobutyl, pentyl, isopentyl, neopentyl, 5,5,5-trifluoropentyl, hexyl, 6,6,6-trifluorohexyl and the like),
(6) lower alkoxy optionally having substituent(s) (e.g., $C_{1-6}$ alkoxy optionally having 1 to 5 substituents selected from a halogen atom, nitro, cyano, hydroxy, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, optionally halogenated $C_{1-6}$ alkoxy such as methoxy, ethoxy, propoxy, isopropoxy, butoxy, isobutoxy, pentyloxy, hexyloxy, trifluoromethoxy etc., and the like),
(7) amino,
(8) mono-lower alkylamino optionally having substituent(s) (e.g., mono-$C_{1-6}$ alkylamino optionally having 1 to 5 substituents selected from a halogen atom, nitro, cyano, hydroxy, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, mono-$C_{1-6}$ alkylamino such as methylamino, ethylamino, propylamino, isopropylamino, butylamino etc., and the like),
(9) di-lower alkylamino optionally having substituent(s) (e.g., di-$C_{1-6}$ alkylamino optionally having 1 to 5 substituents selected from a halogen atom, nitro, cyano, hydroxy, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, di-$C_{1-6}$ alkylamino such as dimethylamino, diethylamino, dipropylamino, diisopropylamino, dibutylamino, N-ethyl-N-methylamino etc., and the like),
(10) carboxy,
(11) lower alkylcarbonyl optionally having substituent(s) (e.g., $C_{1-6}$ alkyl-carbonyl optionally having 1 to 5 substituents selected from a halogen atom, nitro, cyano, hydroxy, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, $C_{1-6}$ alkyl-carbonyl such as acetyl, propionyl etc., and the like),
(12) lower alkoxycarbonyl optionally having substituent(s) (e.g., $C_{1-6}$ alkoxy-carbonyl optionally having 1 to 5 substituents selected from a halogen atom, nitro, cyano, hydroxy, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, $C_{1-6}$ alkoxy-carbonyl such as methoxycarbonyl, ethoxycarbonyl, propoxycarbonyl, butoxycarbonyl etc., and the like),
(13) carbamoyl,
(14) mono-lower alkylcarbamoyl optionally having substituent(s) (e.g., mono-$C_{1-6}$ alkyl-carbamoyl optionally having 1 to 5 substituents selected from a halogen atom, nitro, cyano, hydroxy, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, mono-$C_{1-6}$ alkyl-carbamoyl such as methylcarbamoyl, ethylcarbamoyl etc., and the like),
(15) di-lower alkylcarbamoyl optionally having substituent(s) (e.g., di-$C_{1-6}$ alkyl-carbamoyl optionally having 1 to 5 substituents selected from a halogen atom, nitro, cyano, hydroxy, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, di-$C_{1-6}$ alkyl-carbamoyl such as dimethylcarbamoyl, diethylcarbamoyl, ethylmethylcarbamoyl etc., and the like),
(16) arylcarbamoyl optionally having substituent(s) (e.g., $C_{6-10}$ aryl-carbamoyl optionally having 1 to 5 substituents selected from a halogen atom, nitro, cyano, hydroxy, optionally halogenated $C_{1-6}$ alkyl, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, $C_{6-10}$ aryl-carbamoyl such as phenylcarbamoyl, naphthylcarbamoyl etc., and the like),

(17) aryl optionally having substituent(s) (e.g., $C_{6-10}$ aryl optionally having 1 to 5 substituents selected from a halogen atom, nitro, cyano, hydroxy, optionally halogenated $C_{1-6}$ alkyl, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, phenyl, naphthyl and the like),

(18) aryloxy optionally having substituent(s) (e.g., $C_{6-10}$ aryloxy optionally having 1 to 5 substituents selected from a halogen atom, nitro, cyano, hydroxy, optionally halogenated $C_{1-6}$ alkyl, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, $C_{6-10}$ aryloxy such as phenyloxy, naphthyloxy etc., and the like),

(19) lower alkylcarbonylamino optionally having substituent(s) (e.g., $C_{1-6}$ alkyl-carbonylamino optionally having 1 to 5 substituents selected from a halogen atom, nitro, cyano, hydroxy, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, optionally halogenated $C_{1-6}$ alkyl-carbonylamino such as acetylamino, trifluoroacetylamino etc., and the like),

(20) oxo,
(21) formyl,
(22) arylcarbonyl (e.g., $C_{6-10}$ aryl-carbonyl such as benzoyl, naphthoyl etc., and the like),
(23) formyloxy,
(24) lower alkanoyloxy (e.g., $C_{1-6}$ alkyl-carbonyloxy such as acetyloxy, propionyloxy, butyryloxy, isobutyryloxy etc., and the like),
(25) arylcarbonyloxy (e.g., $C_{6-10}$ aryl-carbonyloxy such as benzoyloxy, naphthoyloxy etc., and the like),
(26) aralkyloxycarbonyl (e.g., $C_{7-12}$ aralkyloxy-carbonyl such as benzyloxycarbonyl etc., and the like),
(27) amidino,
(28) imino,
(29) 3- to 6-membered cyclic amino optionally containing, besides a carbon atom and one nitrogen atom, 1 to 3 hetero atoms selected from a nitrogen atom, an oxygen atom and a sulfur atom and optionally having substituent(s) (e.g., 3- to 6-membered cyclic amino optionally containing, besides a carbon atom and one nitrogen atom, 1 to 3 hetero atoms selected from a nitrogen atom, an oxygen atom and a sulfur atom and optionally having 1 to 5 substituents selected from a halogen atom, nitro, cyano, hydroxy, optionally halogenated $C_{1-6}$ alkyl, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino, oxo and the like; for example, aziridinyl, azetidinyl, pyrrolidinyl, pyrrolinyl, pyrrolyl, imidazolyl, pyrazolyl, imidazolidinyl, piperidyl, morpholinyl, dihydropyridyl, tetrahydropyridyl, piperazinyl, N-methylpiperazinyl, N-ethylpiperazinyl and the like),

(30) alkylenedioxy (e.g., $C_{1-3}$ alkylenedioxy such as methylenedioxy, ethylenedioxy etc., and the like),
(31) mercapto,
(32) sulfo,
(33) sulfino,
(34) phosphono,
(35) sulfamoyl,
(36) mono-lower alkylsulfamoyl (e.g., mono-$C_{1-6}$ alkylsulfamoyl such as N-methylsulfamoyl, N-ethylsulfamoyl, N-propylsulfamoyl, N-isopropylsulfamoyl, N-butylsulfamoyl etc., and the like),
(37) di-lower alkylsulfamoyl (e.g., di-$C_{1-6}$ alkylsulfamoyl such as N,N-dimethylsulfamoyl, N,N-diethylsulfamoyl, N,N-dipropylsulfamoyl, N,N-dibutylsulfamoyl etc., and the like),
(38) lower alkylthio (e.g., $C_{1-6}$ alkylthio such as methylthio, ethylthio, propylthio, isopropylthio, butylthio, sec-butylthio, tert-butylthio etc., and the like),
(39) arylthio (e.g., $C_{6-10}$ arylthio such as phenylthio, naphthylthio etc., and the like),
(40) lower alkylsulfinyl (e.g., $C_{1-6}$ alkylsulfinyl such as methylsulfinyl, ethylsulfinyl, propylsulfinyl, butylsulfinyl etc., and the like),
(41) arylsulfinyl (e.g., $C_{6-10}$ arylsulfinyl such as phenylsulfinyl, naphthylsulfinyl etc., and the like),
(42) lower alkylsulfonyl (e.g., $C_{1-6}$ alkylsulfonyl such as methylsulfonyl, ethylsulfonyl, propylsulfonyl, butylsulfonyl etc., and the like),
(43) arylsulfonyl (e.g., $C_{6-10}$ arylsulfonyl such as phenylsulfonyl, naphthylsulfonyl etc., and the like) and the like are used. The "hydrocarbon group" of the "hydrocarbon group optionally having substituent(s)" may have 1 to 5, preferably 1 to 3, substituents selected from the aforementioned substituents at substitutable position(s) of the hydrocarbon group. When the number of substituents is two or more, each substituent may be the same or different.

As the "heterocyclic group" of the term "heterocyclic group optionally having substituent(s)" used in the present specification, for example, a 5- to 14-membered (preferably 5- to 10-membered) (monocyclic, bicyclic or tricyclic, preferably monocyclic or bicyclic) heterocyclic group containing, besides a carbon atom, 1 to 4 (preferably 1 to 3) hetero atoms of one or two kinds selected from a nitrogen atom, an oxygen atom and a sulfur atom, can be mentioned. For example, a 5-membered ring group containing, besides a carbon atom, 1 to 4 hetero atoms selected from a nitrogen atom, an oxygen atom and a sulfur atom, such as 2- or 3-thienyl, 2- or 3-furyl, 1-, 2- or 3-pyrrolyl, 1-, 2- or 3-pyrrolidinyl, 2-, 4- or 5-oxazolyl, 3-, 4- or 5-isoxazolyl, 2-, 4- or 5-thiazolyl, 3-, 4- or 5-isothiazolyl, 3-, 4- or 5-pyrazolyl, 2-, 3- or 4-pyrazolidinyl, 2-, 4- or 5-imidazolyl, 2- or 4-imidazolinyl, 1,2,3-triazolyl, 1,2,4-triazolyl, 1H- or 2H-tetrazolyl and the like; for example, a 6-membered ring group containing, besides a carbon atom, 1 to 4 hetero atoms selected from a nitrogen atom, an oxygen atom and a sulfur atom, such as 2-, 3- or 4-pyridyl, N-oxido-2-, 3- or 4-pyridyl, 2-, 4- or 5-pyrimidinyl, N-oxido-2-, 4- or 5-pyrimidinyl, thiomorpholinyl, morpholinyl, piperidino, 2-, 3- or 4-piperidyl, thiopyranyl, 1,4-oxazinyl, 1,4-thiazinyl, 1,3-thiazinyl, 1- or 2-piperazinyl, triazinyl, 3- or 4-pyridazinyl, pyrazinyl, N-oxido-3- or 4-pyridazinyl and the like; for example, a bicyclic or tricyclic fused ring group containing, besides a carbon atom, 1 to 4 hetero atoms selected from a nitrogen atom, an oxygen atom and a sulfur atom (preferably, a group formed by condensation of the aforementioned 5- or 6-membered ring with one or two 5- or 6-membered ring group(s) optionally containing, besides a carbon atom, 1 to 4 hetero atoms selected from a nitrogen atom, an oxygen atom and a sulfur atom), such as indolyl, benzofuryl, benzothiazolyl, benzoxazolyl, benzimidazolyl, quinolyl, isoquinolyl, phthalazinyl, quinazolinyl, quinoxalinyl, indolizinyl, quinolizinyl, 1,8-naphthyridinyl, dibenzofuranyl, carbazolyl, acridinyl, phenanthridinyl, chromanyl, phenothiazinyl, phenoxazinyl and the like; and the like are used. Of these, a 5- to 7-membered (preferably 5- or 6-membered) heterocyclic group containing, besides a carbon atom, 1 to 3 hetero atoms selected from a nitrogen atom, an oxygen atom and a sulfur atom is preferable.

As the substituent that the "heterocyclic group" of the "heterocyclic group optionally having substituent(s)" may have, the aforementioned "hydrocarbon group optionally having substituent(s)", and the groups recited as examples of the substituents that the "hydrocarbon group optionally having substituent(s)" may have can be mentioned. Particularly preferably, for example, (1) a halogen atom (e.g., fluorine, chlorine, bromine, iodine),
(2) lower alkyl (e.g., $C_{1-6}$ alkyl such as methyl, ethyl, propyl, isopropyl, butyl, isobutyl, sec-butyl, tert-butyl, pentyl, hexyl etc., and the like),
(3) cycloalkyl (e.g., $C_{3-6}$ cycloalkyl such as cyclopropyl, cyclobutyl, cyclopentyl, cyclohexyl, and the like),
(4) lower alkynyl (e.g., $C_{2-6}$ alkynyl such as ethynyl, 1-propynyl, propargyl etc., and the like),
(5) lower alkenyl (e.g., $C_{2-6}$ alkenyl such as vinyl, allyl, isopropenyl, butenyl, isobutenyl etc., and the like),
(6) aralkyl (e.g., $C_{7-12}$ aralkyl such as benzyl, α-methylbenzyl, phenethyl etc., and the like),
(7) aryl (e.g., $C_{6-10}$ aryl such as phenyl, naphthyl etc., and the like, preferably phenyl),
(8) lower alkoxy (e.g., $C_{1-6}$ alkoxy such as methoxy, ethoxy, propoxy, isopropoxy, butoxy, isobutoxy, sec-butoxy, tert-butoxy etc., and the like),
(9) aryloxy (e.g., $C_{6-10}$ aryloxy such as phenoxy etc., and the like),
(10) lower alkanoyl (e.g., formyl; $C_{1-6}$ alkyl-carbonyl such as acetyl, propionyl, butyryl, isobutyryl etc., and the like),
(11) arylcarbonyl (e.g., $C_{6-10}$ aryl-carbonyl such as benzoyl, naphthoyl etc., and the like),
(12) lower alkanoyloxy (e.g., formyloxy; $C_{1-6}$ alkyl-carbonyloxy such as acetyloxy, propionyloxy, butyryloxy, isobutyryloxy etc., and the like),
(13) arylcarbonyloxy (e.g., $C_{6-10}$ aryl-carbonyloxy such as benzoyloxy, naphthoyloxy etc., and the like),
(14) carboxy,
(15) lower alkoxycarbonyl (e.g., $C_{1-6}$ alkoxy-carbonyl such as methoxycarbonyl, ethoxycarbonyl, propoxycarbonyl, isopropoxycarbonyl, butoxycarbonyl, isobutoxycarbonyl, tert-butoxycarbonyl etc., and the like),
(16) aralkyloxycarbonyl (e.g., $C_{7-12}$ aralkyloxy-carbonyl such as benzyloxycarbonyl etc., and the like),
(17) carbamoyl,
(18) lower halogenoalkyl (e.g., mono-, di- or tri-halogeno-$C_{1-6}$ alkyl such as chloromethyl, dichloromethyl, trifluoromethyl, 2,2,2-trifluoroethyl etc., and the like),
(19) oxo,
(20) amidino,
(21) imino,
(22) amino,
(23) mono-lower alkylamino (e.g., mono-$C_{1-6}$ alkylamino such as methylamino, ethylamino, propylamino, isopropylamino, butylamino etc., and the like),
(24) di-lower alkylamino (e.g., di-$C_{1-6}$ alkylamino such as dimethylamino, diethylamino, dipropylamino, diisopropylamino, dibutylamino, N-ethyl-N-methylamino etc., and the like),
(25) 3- to 6-membered cyclic amino optionally containing, besides a carbon atom and one nitrogen atom, 1 to 3 hetero atoms selected from a nitrogen atom, an oxygen atom and a sulfur atom, which optionally has substituent(s) (e.g., 3- to 6-membered cyclic amino optionally containing, besides a carbon atom and one nitrogen atom, 1 to 3 hetero atoms selected from a nitrogen atom, an oxygen atom and a sulfur atom, which optionally has 1 to 5 substituents selected from a halogen atom, nitro, cyano, hydroxy, optionally halogenated $C_{1-6}$ alkyl, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino, oxo and the like; for example, aziridinyl, azetidinyl, pyrrolidinyl, pyrrolinyl, pyrrolyl, imidazolyl, pyrazolyl, imidazolidinyl, piperidyl, morpholinyl, dihydropyridyl, tetrahydropyridyl, piperazinyl, N-methylpiperazinyl, N-ethylpiperazinyl and the like),
(26) alkylenedioxy (e.g., $C_{1-3}$ alkylenedioxy such as methylenedioxy, ethylenedioxy etc., and the like),
(27) hydroxy,
(28) nitro,
(29) cyano,
(30) mercapto,
(31) sulfo,
(32) sulfino,
(33) phosphono,
(34) sulfamoyl,
(35) mono-lower alkylsulfamoyl (e.g., mono-$C_{1-6}$ alkylsulfamoyl such as N-methylsulfamoyl, N-ethylsulfamoyl, N-propylsulfamoyl, N-isopropylsulfamoyl, N-butylsulfamoyl etc., and the like),
(36) di-lower alkylsulfamoyl (e.g., di-$C_{1-6}$ alkylsulfamoyl such as N,N-dimethylsulfamoyl, N,N-diethylsulfamoyl, N,N-dipropylsulfamoyl, N,N-dibutylsulfamoyl etc., and the like),
(37) lower alkylthio (e.g., $C_{1-6}$ alkylthio such as methylthio, ethylthio, propylthio, isopropylthio, butylthio, sec-butylthio, tert-butylthio etc., and the like),
(38) arylthio (e.g., $C_{6-10}$ arylthio such as phenylthio, naphthylthio etc., and the like),
(39) lower alkylsulfinyl (e.g., $C_{1-6}$ alkylsulfinyl such as methylsulfinyl, ethylsulfinyl, propylsulfinyl, butylsulfinyl etc., and the like),
(40) arylsulfinyl (e.g., $C_{6-10}$ arylsulfinyl such as phenylsulfinyl, naphthylsulfinyl etc., and the like),
(41) lower alkylsulfonyl (e.g., $C_{1-6}$ alkylsulfonyl such as methylsulfonyl, ethylsulfonyl, propylsulfonyl, butylsulfonyl etc., and the like),
(42) arylsulfonyl (e.g., $C_{6-10}$ arylsulfonyl such as phenylsulfonyl, naphthylsulfonyl etc., and the like) and the like are used. The "heterocyclic group" of the "heterocyclic group optionally having substituent(s)" may have 1 to 5, preferably 1 to 3, substituents selected from the aforementioned substituents, at substitutable position(s) of the heterocyclic group. When the number of the substituents is two or more, each substituent may be the same or different.

The term used in the present specification "amino optionally having substituent(s)" means amino optionally having, as substituent, 1 or 2, the same or different groups selected from, for example, the aforementioned "hydrocarbon group optionally having substituent(s)", and the groups recited as examples of the substituent that the "hydrocarbon group optionally having substituent(s)" may have and the like. Preferable examples of the substituent that the "amino" may have include $C_{1-6}$ alkyl optionally having substituent(s), $C_{6-10}$ aryl optionally having substituent(s) and the like. As the substituent that the "$C_{1-6}$ alkyl" and "$C_{6-10}$ aryl" may have, those similar to the substituents that the aforementioned "hydrocarbon group" may have are used.

The term used in the present specification "hydroxy optionally having a substituent" means (1) hydroxy or (2) hydroxy having, instead of the hydrogen atom of hydroxy, one group selected from, for example, the aforementioned "hydrocarbon group optionally having substituent(s)", the groups recited as examples of the substituent that the "hydrocarbon group optionally having substituent(s)" may have and the like. As the "hydroxy optionally having a substituent", for example, hydroxy, $C_{1-6}$ alkoxy optionally having substituent(s), $C_{2-6}$ alkenyloxy optionally having substituent(s), $C_{2-6}$ alkynyloxy optionally having substituent(s), $C_{3-6}$ cycloalkyloxy optionally having substituent(s), $C_{6-14}$ aryloxy optionally having substituent(s) and the like can be mentioned. Preferred are hydroxy, $C_{1-6}$ alkoxy optionally having substituent(s), $C_{6-14}$ aryloxy optionally having substituent(s) and the like. As the substituent that the "$C_{1-6}$ alkoxy", "$C_{2-6}$ alkenyloxy", "$C_{2-6}$ alkynyloxy", "$C_{3-6}$ cycloalkyloxy" and "$C_{6-14}$ aryloxy" may have, those similar to the substituents that the aforementioned "hydrocarbon group" may have are used.

The term used in the present specification "mercapto optionally having a substituent" means (1) mercapto or (2) mercapto having, instead of the hydrogen atom of mercapto, one group selected from, for example, the aforementioned "hydrocarbon group optionally having substituent(s)", the groups recited as examples of the substituent that the "hydrocarbon group optionally having substituent(s)" may have and the like. As the "mercapto optionally having a substituent", for example, mercapto, $C_{1-6}$ alkylthio optionally having substituent(s), $C_{2-6}$ alkenylthio optionally having substituent(s), $C_{2-6}$ alkynylthio optionally having substituent(s), $C_{3-6}$ cycloalkylthio optionally having substituent(s), $C_{6-14}$ arylthio optionally having substituent(s) and the like can be mentioned. Preferred are mercapto, $C_{1-6}$ alkylthio optionally having substituent(s), $C_{6-14}$ arylthio optionally having substituent(s) and the like. As the substituent that the "$C_{1-6}$ alkylthio", "$C_{2-6}$ alkenylthio", "$C_{2-6}$ alkynylthio", "$C_{3-6}$ cycloalkylthio" and "$C_{6-14}$ arylthio" may have, those similar to the substituents that the aforementioned "hydrocarbon group" may have are used.

As the "lower alkyl" of the term "lower alkyl optionally having substituent(s)" used in the present specification, for example, $C_{1-6}$ alkyl such as methyl, ethyl, propyl, isopropyl, butyl, isobutyl, sec-butyl, tert-butyl etc., and the like can be mentioned. The "lower alkyl" may have, as the substituent, for example, 1 to 3 substituents that the aforementioned "hydrocarbon group" may have, and the like.

In the aforementioned formulas, $R^1$ is a hydrocarbon group optionally having substituent(s), amino optionally having substituent(s), hydroxy optionally having a substituent or a heterocyclic group optionally having substituent(s).

Preferable examples of the "hydrocarbon group" of the "hydrocarbon group optionally having substituent(s)" for $R^1$ include alkyl (e.g., $C_{1-6}$ alkyl such as methyl, ethyl, propyl, isopropyl etc., and the like), alkenyl (e.g., $C_{2-6}$ alkenyl such as vinyl etc., and the like), alkynyl (e.g., $C_{2-6}$ alkynyl such as ethynyl etc., and the like), cycloalkyl (e.g., $C_{3-6}$ cycloalkyl such as cyclopropyl, cyclobutyl, cyclopentyl, cyclohexyl, and the like), aryl (e.g., $C_{6-14}$ aryl such as phenyl etc., and the like) and the like. More preferable examples include alkyl (e.g., $C_{1-6}$ alkyl such as methyl, ethyl etc., and the like), alkenyl (e.g., $C_{2-6}$ alkenyl such as vinyl etc., and the like), cycloalkyl (e.g., $C_{3-6}$ cycloalkyl such as cyclopropyl etc., and the like), phenyl and the like. The "alkyl", "alkenyl", "alkynyl", "cycloalkyl" and "aryl" may have, for example, 1 to 5, preferably 1 to 3, from the substituents that the aforementioned "hydrocarbon group" may have (preferably, a halogen atom such as chlorine, fluorine etc.; $C_{1-6}$ alkoxy such as methoxy, ethoxy etc.; hydroxy; and the like), and the like.

As the substituent of the "amino optionally having substituent(s)" for $R^1$, preferably, for example, 1 or 2 from lower alkyl optionally having substituent(s), aryl optionally having substituent(s) and the like are used, and particularly, one from lower alkyl optionally having substituent(s) and the like is used. The "lower alkyl" optionally has, for example, 1 to 3 from the substituents that the aforementioned "hydrocarbon group" optionally has and the like. Examples of the "aryl" include $C_{6-10}$ aryl such as phenyl etc., and the like are used. The "aryl" optionally has, for example, 1 to 5, preferably 1 to 3, from the substituents that the aforementioned "hydrocarbon group" optionally has (preferably, a halogen atom such as fluorine, chlorine etc.; $C_{1-6}$ alkoxy such as methoxy, ethoxy etc.; and the like). Examples of the "amino optionally having substituent(s)" include $C_{6-10}$ arylamino (e.g., phenylamino and the like) optionally having 1 to 3 $C_{1-6}$ alkoxy (e.g., methoxy and the like), mono- or di-$C_{1-6}$ alkylamino (e.g., methylamino, ethylamino, propylamino, isopropylamino, butylamino, tert-butylamino, dimethylamino, diethylamino, N-ethyl-N-methylamino and the like) and the like.

Preferable examples of the "hydroxy optionally having a substituent" for $R^1$ include hydroxy, $C_{1-6}$ alkoxy (e.g., methoxy, ethoxy, propoxy, isopropoxy, tert-butoxy and the like) optionally having substituent(s), $C_{2-6}$ alkenyloxy (e.g., vinyloxy and the like) optionally having substituent(s), $C_{2-6}$ alkynyloxy (e.g., ethynyloxy and the like) optionally having substituent(s), $C_{3-6}$ cycloalkyloxy (e.g., cyclopropyloxy, cyclobutyloxy, cyclopentyloxy, cyclohexyloxy and the like) optionally having substituent(s), $C_{6-14}$ aryloxy (e.g., phenoxy and the like) optionally having substituent(s) and the like, particularly, $C_{1-6}$ alkoxy (e.g., methoxy, tert-butoxy and the like) optionally having substituent(s), $C_{2-6}$ alkenyloxy (e.g., vinyloxy and the like) optionally having substituent(s), $C_{3-6}$ cycloalkyloxy (e.g., cyclopropyloxy and the like) optionally having substituent(s) and the like can be mentioned. The "$C_{1-6}$ alkoxy", "$C_{2-6}$ alkenyloxy", "$C_{2-6}$ alkynyloxy", "$C_{3-6}$ cycloalkyloxy" and "$C_{6-14}$ aryloxy" optionally have, for example, 1 to 5, preferably 1 to 3, from the substituents that the aforementioned "hydrocarbon group" optionally has (preferably, a halogen atom such as chlorine, fluorine etc.; $C_{1-6}$ alkoxy such as methoxy, ethoxy etc.; and the like) and the like.

Preferable examples of the "heterocyclic group" of the "heterocyclic group optionally having substituent(s)" for $R^1$ include a 5- or 6-membered heterocyclic group containing, besides a carbon atom, 1 to 3 hetero atoms selected from a nitrogen atom, an oxygen atom and a sulfur atom, and the like. Specifically, for example, 1-, 2- or 3-pyrrolidinyl, 2- or 4-imidazolinyl, 2-, 3- or 4-pyrazolidinyl, piperidino, 2-, 3- or 4-piperidyl, 1- or 2-piperazinyl, morpholinyl, 2- or 3-thienyl, 2-, 3- or 4-pyridyl, 2- or 3-furyl, pyrazinyl, 2-pyrimidinyl, 3-pyrrolyl, 3-pyridazinyl, 3-isothiazolyl, 3-isoxazolyl and the like can be mentioned. Particularly preferably, 6-membered nitrogen-containing heterocyclic group (e.g., pyridyl and the like) and the like are used. Preferable examples of the substituent of the "heterocyclic group optionally having substituent(s)" for $R^1$ include a halogen atom (e.g., chlorine, fluorine and the like), $C_{1-6}$ alkyl (e.g., methyl, ethyl and the like), $C_{1-6}$ alkoxy (e.g., methoxy, ethoxy and the like), aralkyloxycarbonyl (e.g., $C_{7-12}$ aralkyloxy-carbonyl such as benzyloxycarbonyl etc., and the like) and the like.

$R^1$ is preferably, for example, (i) $C_{1-6}$ alkyl optionally having substituent(s), (ii) $C_{3-6}$ cycloalkyl optionally having substituent(s), (iii) $C_{2-6}$ alkenyl optionally having substituent(s), (iv) $C_{1-6}$ alkoxy optionally having substituent(s) or the like. These groups optionally have, as substituents, for example, 1 to 5 from the substituents that the aforementioned "hydrocarbon group" optionally has and the like. As $R^1$, particularly, $C_{1-6}$ alkyl, $C_{3-6}$ cycloalkyl or $C_{1-6}$ alkoxy is preferable. Particularly, $C_{1-6}$ alkyl (e.g., methyl, ethyl) is more preferable, and methyl is most preferable.

In the aforementioned formulas, $R^2$ is a hydrogen atom or a hydrocarbon group optionally having substituent(s).

Preferable examples of the "hydrocarbon group" of the "hydrocarbon group optionally having substituent(s)" for $R^2$ include alkyl (e.g., $C_{1-6}$ alkyl such as methyl, ethyl, propyl, isopropyl etc., and the like), alkenyl (e.g., $C_{2-6}$ alkenyl such as vinyl etc., and the like), alkynyl (e.g., $C_{2-6}$ alkynyl such as ethynyl etc., and the like), cycloalkyl (e.g., $C_{3-6}$ cycloalkyl such as cyclopropyl, cyclobutyl, cyclopentyl, cyclohexyl etc., and the like), aryl (e.g., $C_{6-14}$ aryl such as phenyl etc., and the like) and the like, particularly alkyl (e.g., $C_{1-6}$ alkyl such as methyl etc., and the like), aryl (e.g., $C_{6-14}$ aryl such as phenyl etc., and the like) and the like. The "alkyl", "alkenyl", "alkynyl", "cycloalkyl" and "aryl" optionally have, for example, 1 to 5, preferably 1 to 3, from the substituents that the aforementioned "hydrocarbon group" optionally has (preferably, a halogen atom such as chlorine, fluorine etc.; $C_{1-6}$ alkoxy such as methoxy, ethoxy etc.; and the like) and the like.

As $R^2$, a hydrogen atom or $C_{1-6}$ alkyl optionally having substituent(s) is preferable, more preferably a hydrogen atom or $C_{1-6}$ alkyl, particularly preferably a hydrogen atom.

In the aforementioned formulas, $R^3$ is a hydrogen atom, a halogen atom, a hydrocarbon group optionally having substituent(s), amino optionally having substituent(s), hydroxy optionally having a substituent or mercapto optionally having a substituent.

As the "halogen atom" for $R^3$, fluorine, chlorine or bromine is preferable.

Preferable examples of the "hydrocarbon group" of the "hydrocarbon group optionally having substituent(s)" for $R^3$ include alkyl (e.g., $C_{1-6}$ alkyl such as methyl, ethyl, propyl, isopropyl etc., and the like), alkenyl (e.g., $C_{2-6}$ alkenyl such as vinyl etc., and the like), alkynyl (e.g., $C_{2-6}$ alkynyl such as ethynyl etc., and the like), cycloalkyl (e.g., $C_{3-6}$ cycloalkyl such as cyclopropyl, cyclobutyl, cyclopentyl, cyclohexyl etc., and the like), aryl (e.g., $C_{6-14}$ aryl such as phenyl etc., and the like) and the like, particularly alkyl (e.g., $C_{1-6}$ alkyl such as methyl etc., and the like), alkenyl (e.g., $C_{2-6}$ alkenyl such as vinyl etc., and the like) and the like. The "alkyl", "alkenyl", "alkynyl", "cycloalkyl" and "aryl" optionally have, for example, 1 to 5, preferably 1 to 3, from the substituents that the aforementioned "hydrocarbon group" optionally has and the like.

Preferable examples of the substituent of the "amino optionally having substituent(s)" for $R^3$ include 1 or 2 from lower alkyl optionally having substituent(s), aryl optionally having substituent(s) and the like, particularly one from lower alkyl optionally having substituent(s) and the like. Examples of the "lower alkyl" include $C_{1-6}$ alkyl such as methyl, ethyl, propyl, isopropyl, butyl, isobutyl, sec-butyl, tert-butyl and the like, and the like. The "lower alkyl" optionally has, for example, 1 to 3 from the substituents that the aforementioned "hydrocarbon group" optionally has. Examples of the "aryl" include $C_{6-10}$ aryl such as phenyl and the like, and the like. The "aryl" optionally has, for example, 1 to 5, preferably 1 to 3, from the substituents that the aforementioned "hydrocarbon group" optionally has (preferably, a halogen atom such as fluorine, chlorine etc.; $C_{1-6}$ alkoxy such as methoxy, ethoxy etc.; and the like). General examples of the "amino optionally having substituent(s)" include $C_{6-10}$ arylamino (e.g., phenylamino and the like) optionally having 1 to 3 $C_{1-6}$ alkoxy (e.g., methoxy and the like), mono- or di-$C_{1-6}$ alkylamino (e.g., methylamino, ethylamino, propylamino, isopropylamino, butylamino, tert-butylamino, dimethylamino, diethylamino, N-ethyl-N-methylamino and the like) and the like.

Preferable examples of the "hydroxy optionally having a substituent" for $R^3$ include hydroxy, $C_{1-6}$ alkoxy (e.g., methoxy, ethoxy, propoxy, isopropoxy and the like) optionally having substituent(s), $C_{2-6}$ alkenyloxy (e.g., vinyloxy and the like) optionally having substituent(s), $C_{2-6}$ alkynyloxy (e.g., ethynyloxy and the like) optionally having substituent(s), $C_{3-6}$ cycloalkyloxy (e.g., cyclopropyloxy, cyclobutyloxy, cyclopentyloxy, cyclohexyloxy and the like) optionally having substituent(s), $C_{6-14}$ aryloxy (e.g., phenoxy and the like) optionally having substituent(s) and the like, particularly, hydroxy, $C_{1-6}$ alkoxy (e.g., methoxy and the like) optionally having substituent(s), $C_{6-14}$ aryloxy (e.g., phenoxy and the like) optionally having substituent(s) and the like. The "$C_{1-6}$ alkoxy", "$C_{2-6}$ alkenyloxy", "$C_{2-6}$ alkynyloxy", "$C_{3-6}$ cycloalkyloxy" and "$C_{6-14}$ aryloxy" optionally have, for example, 1 to 5, preferably 1 to 3, from the substituents that the aforementioned "hydrocarbon group" optionally has (preferably, a halogen atom such as chlorine, fluorine etc.; $C_{1-6}$ alkoxy such as methoxy, ethoxy etc.; and the like) and the like.

Preferable examples of the "mercapto optionally having a substituent" for $R^3$ include mercapto, $C_{1-6}$ alkylthio (e.g., methylthio, ethylthio, propylthio, isopropylthio and the like) optionally having substituent(s), $C_{2-6}$ alkenylthio (e.g., vinylthio and the like) optionally having substituent(s), $C_{2-6}$ alkynylthio (e.g., ethynylthio and the like) optionally having substituent(s), $C_{3-6}$ cycloalkylthio (e.g., cyclopropylthio, cyclobutylthio, cyclopentylthio, cyclohexylthio and the like) optionally having substituent(s), $C_{6-14}$ arylthio (e.g., phenylthio and the like) optionally having substituent(s) and the like. Specific examples include mercapto, $C_{1-6}$ alkylthio (e.g., methylthio and the like) optionally having substituent(s), $C_{6-14}$ arylthio (e.g., phenylthio and the like) optionally having substituent(s) and the like. The "$C_{1-6}$ alkylthio", "$C_{2-6}$ alkenylthio", "$C_{2-6}$ alkynylthio", "$C_{3-6}$ cycloalkylthio" and "$C_{6-14}$ arylthio" may have, for example, 1 to 5, preferably 1 to 3, from the substituents that the aforementioned "hydrocarbon group" may have (preferably, a halogen atom such as chlorine, fluorine etc.; $C_{1-6}$ alkoxy such as methoxy, ethoxy etc.; and the like), and the like.

$R^3$ is preferably a hydrogen atom or $C_{1-6}$ alkyl optionally having substituent(s), more preferably, a hydrogen atom or $C_{1-6}$ alkyl, particularly preferably, a hydrogen atom.

In the aforementioned formulas, ring A is a 5-membered ring optionally having substituent(s).

As the substituent of the "5-membered ring optionally having substituent(s)", for example, a halogen atom, a hydrocarbon group optionally having substituent(s), amino optionally having substituent(s), hydroxy optionally having a substituent, mercapto optionally having a substituent, a heterocyclic group optionally having substituent(s) and the like can be mentioned. Ring A may have 1 or 2 of the above-mentioned substituents at substitutable position(s).

Preferable examples of the "halogen atom" include fluorine, chlorine and bromine.

Preferable examples of the "hydrocarbon group" of the "hydrocarbon group optionally having substituent(s)" include alkyl (e.g., $C_{1-6}$ alkyl such as methyl, ethyl, propyl, isopropyl etc., and the like), alkenyl (e.g., $C_{2-6}$ alkenyl such as vinyl etc., and the like), alkynyl (e.g., $C_{2-6}$ alkynyl such as ethynyl etc., and the like), cycloalkyl (e.g., $C_{3-6}$ cycloalkyl such as cyclopropyl, cyclobutyl, cyclopentyl, cyclohexyl, and the like), aryl (e.g., $C_{6-14}$ aryl such as phenyl etc., and the like) and the like. Of these, preferable examples include alkyl (e.g., $C_{1-6}$ alkyl such as methyl etc., and the like), alkenyl (e.g., $C_{2-6}$ alkenyl such as vinyl etc., and the like) and the like. The "alkyl", "alkenyl", "alkynyl", "cycloalkyl" and "aryl" may have, for example, 1 to 5, preferably 1 to 3, substituents that the aforementioned "hydrocarbon group" may have, and the like.

Preferable examples of the "amino optionally having substituent(s)" include amino, $C_{1-6}$ alkylamino optionally having substituent(s), $C_{6-10}$ arylamino optionally having substituent(s) and the like. Of these, examples include amino, mono- or di-$C_{1-6}$ alkylamino (e.g., methylamino, ethylamino, propylamino, isopropylamino, butylamino, tert-butylamino, dimethylamino, diethylamino, N-ethyl-N-methylamino and the like), $C_{6-10}$ arylamino (e.g., phenylamino and the like) and the like.

Preferable examples of the "hydroxy optionally having a substituent" include hydroxy, $C_{1-6}$ alkoxy (e.g., methoxy, ethoxy, propoxy, isopropoxy and the like) optionally having substituent(s), $C_{2-6}$ alkenyloxy (e.g., vinyloxy and the like) optionally having substituent(s), $C_{2-6}$ alkynyloxy (e.g., ethynyloxy and the like) optionally having substituent(s), $C_{3-6}$ cycloalkyloxy (e.g., cyclopropyloxy, cyclobutyloxy, cyclopentyloxy, cyclohexyloxy and the like) optionally having substituent(s), $C_{6-14}$ aryloxy (e.g., phenoxy and the like) optionally having substituent(s) and the like. Of these, preferable examples include hydroxy, $C_{1-6}$ alkoxy (e.g., methoxy and the like) optionally having substituent(s), $C_{6-14}$ aryloxy (e.g., phenoxy and the like) optionally having substituent(s) and the like. The "$C_{1-6}$ alkoxy", "$C_{2-6}$ alkenyloxy", "$C_{2-6}$ alkynyloxy", "$C_{3-6}$ cycloalkyloxy" and "$C_{6-14}$ aryloxy" may have, for example, 1 to 5, preferably 1 to 3, from the substituents that the aforementioned "hydrocarbon group" may have (preferably, a halogen atom such as chlorine, fluorine etc.; $C_{1-6}$ alkoxy such as methoxy, ethoxy etc.; and the like), and the like.

Preferable examples of the "mercapto optionally having a substituent" include mercapto, $C_{1-6}$ alkylthio (e.g., methylthio, ethylthio, propylthio, isopropylthio and the like) optionally having substituent(s), $C_{2-6}$ alkenylthio (e.g., vinylthio and the like) optionally having substituent(s), $C_{2-6}$ alkynylthio (e.g., ethynylthio and the like) optionally having substituent(s), $C_{3-6}$ cycloalkylthio (e.g., cyclopropylthio, cyclobutylthio, cyclopentylthio, cyclohexylthio and the like) optionally having substituent(s), $C_{6-14}$ arylthio (e.g., phenylthio and the like) optionally having substituent(s) and the like. Of these, preferable examples include mercapto, $C_{1-6}$ alkylthio (e.g., methylthio and the like) optionally having substituent(s), $C_{6-14}$ arylthio (e.g., phenylthio and the like) optionally having substituent(s) and the like. The "$C_{1-6}$ alkylthio", "$C_{2-6}$ alkenylthio", "$C_{2-6}$ alkynylthio", "$C_{3-6}$ cycloalkylthio" and "$C_{6-14}$ arylthio" may have, for example, 1 to 5, preferably 1 to 3, from the substituents that the aforementioned "hydrocarbon group" may have (preferably, a halogen atom such as chlorine, fluorine etc.; $C_{1-6}$ alkoxy such as methoxy, ethoxy etc.; and the like), and the like.

Preferable examples of the "heterocyclic group" of the "heterocyclic group optionally having substituent(s)" include a 5- or 6-membered heterocyclic group containing, besides a carbon atom, 1 to 3 hetero atoms selected from a nitrogen atom, an oxygen atom and a sulfur atom and the like. Specifically, for example, 1-, 2- or 3-pyrrolidinyl, 2- or 4-imidazolinyl, 2-, 3- or 4-pyrazolidinyl, piperidino, 2-, 3- or 4-piperidyl, 1- or 2-piperazinyl, morpholinyl, 2- or 3-thienyl, 2-, 3- or 4-pyridyl, 2- or 3-furyl, pyrazinyl, 2-pyrimidinyl, 3-pyrrolyl, 3-pyridazinyl, 3-isothiazolyl, 3-isoxazolyl and the like can be mentioned. Specific preferable examples include a 6-membered nitrogen-containing heterocyclic group (e.g., pyridyl and the like) and the like. Preferable examples of the substituent of the "heterocyclic group optionally having substituent(s)" include a halogen atom (e.g., chlorine, fluorine and the like), $C_{1-6}$ alkyl (e.g., methyl, ethyl and the like), $C_{1-6}$ alkoxy (e.g., methoxy, ethoxy and the like), aralkyloxycarbonyl (e.g., $C_{7-12}$ aralkyloxy-carbonyl such as benzyloxycarbonyl etc., and the like), amino, mono-$C_{1-6}$ alkylamino (e.g., methylamino, ethylamino and the like), di-$C_{1-6}$ alkylamino (e.g., dimethylamino, diethylamino and the like) and the like.

Ring A is preferably a 5-membered ring optionally having 1 or 2 substituents selected from a halogen atom, a hydrocarbon group optionally having substituent(s), amino optionally having substituent(s), hydroxy optionally having a substituent and mercapto optionally having a substituent.

Ring A is, more preferably, a 5-membered ring optionally having 1 or 2 substituents selected from a halogen atom, $C_{1-6}$ alkyl optionally having substituent(s), $C_{2-6}$ alkenyl optionally having substituent(s), $C_{3-6}$ cycloalkyl optionally having substituent(s) and $C_{6-10}$ aryl optionally having substituent(s). More preferably, a 5-membered ring optionally having 1 or 2 substituents selected from a halogen atom (e.g. fluorine, chlorine, bromine), $C_{1-6}$ alkyl (e.g. methyl, ethyl), $C_{6-10}$ aryl (e.g. phenyl) and $C_{1-6}$ alkoxy-carbonyl (e.g. ethoxycarbonyl). Particularly, a 5-membered ring optionally having 1 or 2 $C_{1-6}$ alkyl (e.g. methyl, ethyl) is preferable. Moreover, 5-membered ring optionally having one $C_{1-6}$ alkyl (e.g. methyl) is preferable.

In the aforementioned formulas, ring B is a 6-membered ring optionally having substituent(s).

As the substituent of the "6-membered ring optionally having substituent(s)", a halogen atom, a hydrocarbon group optionally having substituent(s), amino optionally having substituent(s), hydroxy optionally having a substituent, mercapto optionally having a substituent, a heterocyclic group optionally having substituent(s) and the like can be mentioned. Ring B optionally has 1 or 2 substituents mentioned above at substitutable position(s). Preferable examples of these substituents include preferable examples of the substituent of ring A and the like.

Ring B is preferably a 6-membered ring optionally having 1 or 2 substituents selected from a halogen atom, a hydrocarbon group optionally having substituent(s), amino optionally having substituent(s), hydroxy optionally having a substituent and mercapto optionally having a substituent.

Ring B is, more preferably, a 6-membered ring optionally having 1 or 2 substituents selected from a halogen atom, hydroxy optionally having a substituent and $C_{1-6}$ alkyl optionally having substituent(s). Particularly, a 6-membered ring optionally having 1 or 2 halogen atoms (e.g. fluorine, chlorine) is preferable. Moreover, an unsubstituted 6-membered ring is preferable.

In the aforementioned formulas, ring C is a 5-membered ring optionally having substituent(s).

As the substituent of the "5-membered ring optionally having substituent(s)", for example, a halogen atom, a hydrocarbon group optionally having substituent(s), hydroxy optionally having a substituent, a heterocyclic group optionally having substituent(s) and the like can be mentioned. Ring C optionally has 1 or 2 substituents mentioned above at substitutable position(s).

Preferable examples of the "halogen atom" include fluorine, chlorine and bromine.

Preferable examples of the "hydrocarbon group" of the "hydrocarbon group optionally having substituent(s)" include alkyl (e.g., $C_{1-6}$ alkyl such as methyl, ethyl, propyl, isopropyl etc., and the like), alkenyl (e.g., $C_{2-6}$ alkenyl such as vinyl etc., and the like), alkynyl (e.g., $C_{2-6}$ alkynyl such as ethynyl etc., and the like), cycloalkyl (e.g., $C_{3-6}$ cycloalkyl such as cyclopropyl, cyclobutyl, cyclopentyl, cyclohexyl, and the like), aryl (e.g., $C_{6-14}$ aryl such as phenyl etc., and the like) and the like. More preferable examples include alkyl (e.g., $C_{1-6}$ alkyl such as methyl etc., and the like), aryl (e.g., $C_{6-14}$ aryl such as phenyl etc., and the like) and the like. The "alkyl", "alkenyl", "alkynyl", "cycloalkyl" and "aryl" may have, for example, 1 to 5, preferably 1 to 3, from the substituents that the aforementioned "hydrocarbon group" optionally has (preferably, a halogen atom such as chlorine, fluorine etc.; $C_{1-6}$ alkoxy such as methoxy, ethoxy etc.; and the like) and the like.

As a preferable example of the "heterocyclic group" of the "heterocyclic group optionally having substituent(s)", for example, a 5- or 6-membered heterocyclic group containing, besides a carbon atom, 1 to 3 hetero atoms selected from a nitrogen atom, an oxygen atom and a sulfur atom and the like can be mentioned. Specifically, for example, 1-, 2- or 3-pyrrolidinyl, 2- or 4-imidazolinyl, 2-, 3- or 4-pyrazolidinyl, piperidino, 2-, 3- or 4-piperidyl, 1- or 2-piperazinyl, morpholinyl, 2- or 3-thienyl, 2-, 3- or 4-pyridyl, 2- or 3-furyl, pyrazinyl, 2-pyrimidinyl, 3-pyrrolyl, 3-pyridazinyl, 3-isothiazolyl, 3-isoxazolyl and the like can be mentioned. Particularly preferably, a 6-membered nitrogen-containing heterocyclic group (e.g., pyridyl and the like) and the like can be mentioned. Preferable examples of the substituent of the "heterocyclic group optionally having substituent(s)" include a halogen atom (e.g., chlorine, fluorine and the like), $C_{1-6}$ alkyl (e.g., methyl, ethyl and the like), $C_{1-6}$ alkoxy (e.g., methoxy, ethoxy and the like), aralkyloxycarbonyl (e.g., $C_{7-12}$ aralkyloxy-carbonyl such as benzyloxycarbonyl etc., and the like), amino, mono-$C_{1-6}$ alkylamino (e.g., methylamino, ethylamino and the like), di-$C_{1-6}$ alkylamino (e.g., dimethylamino, diethylamino and the like) and the like.

Ring C is preferably a 5-membered ring optionally having 1 or 2 substituents selected from a halogen atom, a hydrocarbon group optionally having substituent(s) and a heterocyclic group optionally having substituent(s).

Ring C is more preferably a 5-membered ring optionally having 1 or 2 substituents selected from $C_{1-6}$ alkyl optionally having substituent(s), $C_{3-6}$ cycloalkyl optionally having substituent(s), $C_{6-10}$ aryl group optionally having substituent(s) and a 5- or 6-membered heterocyclic group optionally having 1 or 2 substituents. Examples of the substituent include 1 or 2 substituents selected from a halogen atom, $C_{1-6}$ alkyl group, $C_{6-10}$ aryl group, $C_{1-6}$ alkoxy group, amino group, mono-$C_{1-6}$ alkylamino group, di-$C_{1-6}$ alkylamino group and the like. Ring C is more preferably a 5-membered ring optionally having one substituent selected from optionally halogenated $C_{1-6}$ alkyl group, optionally halogenated $C_{3-6}$ cycloalkyl group, optionally halogenated $C_{6-10}$ aryl group, optionally halogenated $C_{7-12}$ aralkyl group and optionally halogenated 5- or 6-membered heterocyclic group. Particularly, as ring C, an unsubstituted 5-membered ring is preferable.

Examples of the tricycle consisting of ring A, ring B and ring C include rings represented by the formulas

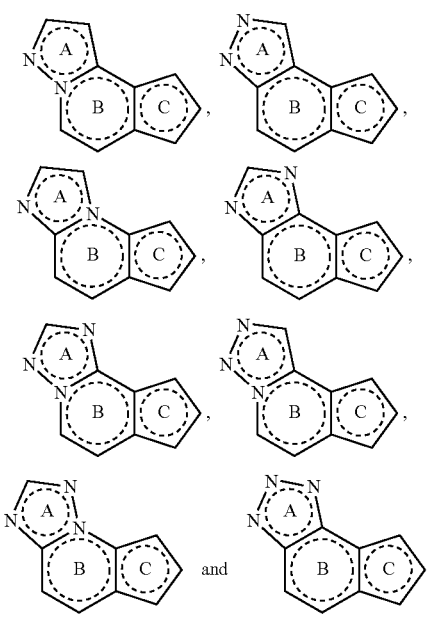

wherein each symbol is as defined above, and the like.

Preferable examples include rings represented by the formulas

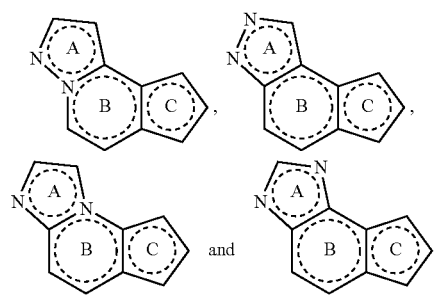

wherein each symbol is as defined above, and the like.

More preferable examples include rings represented by the formulas

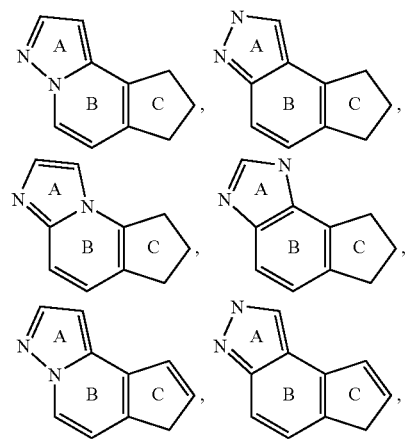

-continued

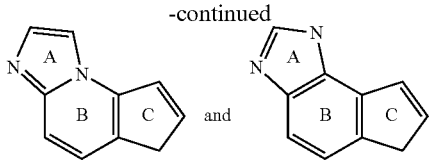

wherein each symbol is as defined above, and the like. Particularly preferably, in the above-mentioned formulas, ring A is a 5-membered ring optionally having 1 or 2 substituents selected from a halogen atom, a hydrocarbon group optionally having substituent(s), amino optionally having substituent(s), hydroxy optionally having a substituent and mercapto optionally having a substituent; ring B is a 6-membered ring optionally having 1 or 2 substituents selected from a halogen atom, a hydrocarbon group optionally having substituent(s), amino optionally having substituent(s), hydroxy optionally having a substituent and mercapto optionally having a substituent; and ring C is a 5-membered ring optionally having or 2 substituents selected from a halogen atom, a hydrocarbon group optionally having substituent(s), hydroxy optionally having a substituent and a heterocyclic group optionally having substituent(s) and the like.

As compound (I), a compound wherein
$R^1$ is $C_{1-6}$ alkyl optionally having substituent(s), $C_{3-6}$ cycloalkyl optionally having substituent(s), $C_{2-6}$ alkenyl optionally having substituent(s) or $C_{1-6}$ alkoxy optionally having substituent(s);
$R^2$ is a hydrogen atom or $C_{1-6}$ alkyl optionally having substituent(s);
$R^3$ is a hydrogen atom or $C_{1-6}$ alkyl optionally having substituent(s);
m is 1;
ring A is a 5-membered ring optionally having 1 or 2 substituents selected from a halogen atom, a hydrocarbon group optionally having substituent(s), amino optionally having substituent(s), hydroxy optionally having a substituent and mercapto optionally having a substituent;
ring B is a 6-membered ring optionally having 1 or 2 substituents selected from a halogen atom, a hydrocarbon group optionally having substituent(s), amino optionally having substituent(s), hydroxy optionally having a substituent and mercapto optionally having a substituent; and
ring C is a 5-membered ring optionally having 1 or 2 substituents selected from a halogen atom, a hydrocarbon group optionally having substituent(s), hydroxy optionally having a substituent and a heterocyclic group optionally having substituent(s) and the like are preferable.

Particularly, a compound wherein
$R^1$ is $C_{1-6}$ alkyl, $C_{3-6}$ cycloalkyl or $C_{1-6}$ alkoxy;
$R^2$ is a hydrogen atom;
$R^3$ is a hydrogen atom;
m is 1;
ring A is a 5-membered ring optionally having 1 or 2 substituents selected from a halogen atom, $C_{1-6}$ alkyl, $C_{6-10}$ aryl and $C_{1-6}$ alkoxy-carbonyl;
ring B is a 6-membered ring optionally having one halogen atom;
ring C is an unsubstituted 5-membered ring;
Xa is (1) CH optionally substituted by $C_{1-6}$ alkyl or $C_{6-10}$ aryl or (2) NH optionally substituted by $C_{1-6}$ alkyl;
Xb is (1) CH optionally substituted by a halogen atom, $C_{1-6}$ alkyl or $C_{1-6}$ alkoxy-carbonyl or (2) NH optionally substituted by $C_{1-6}$ alkyl;
Xc is C or N; and
Xd is C or N, are preferable.

Preferable examples of compound (I) include compounds represented by the formulas

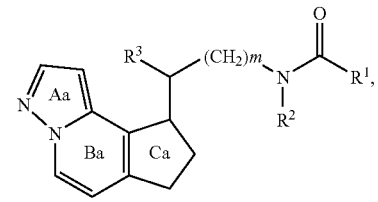

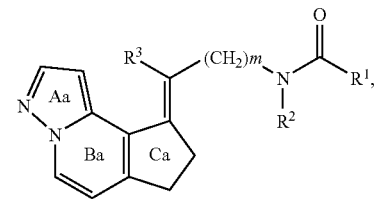

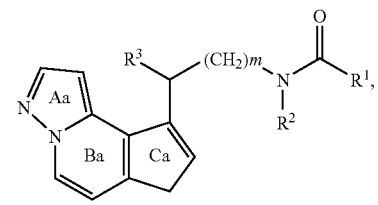

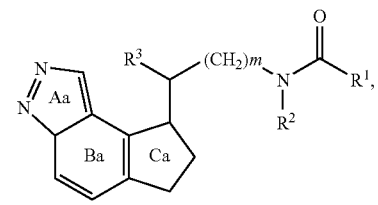

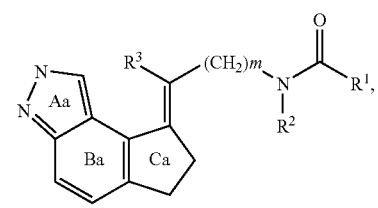

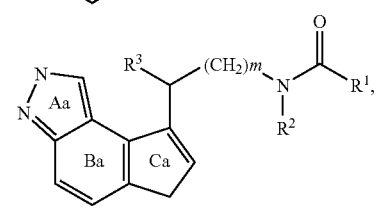

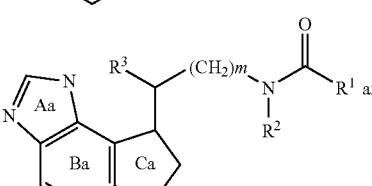 and

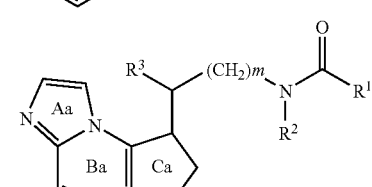

wherein ring Aa is as defined for the above-mentioned ring A, ring Ba is as defined for the above-mentioned ring B, ring Ca is as defined for the above-mentioned ring C, and other symbols are as defined above, and the like.

Particularly, a compound wherein $R^1$ is $C_{1-6}$ alkyl, $C_{3-6}$ cycloalkyl or $C_{1-6}$ alkoxy; $R^2$ is a hydrogen atom; $R^3$ is a hydrogen atom; m is 1; ring Aa is a 5-membered ring optionally having 1 or 2 substituents selected from a halogen atom, $C_{1-6}$ alkyl, $C_{6-10}$ aryl and $C_{1-6}$ alkoxy-carbonyl; ring Ba is a 6-membered ring optionally having one halogen atom; ring Ca is an unsubstituted 5-membered ring, and the like can be mentioned. Moreover, a compound wherein $R^1$ is $C_{1-6}$ alkyl, $C_{3-6}$ cycloalkyl, $C_{1-6}$ alkoxy or $C_{1-6}$ alkylamino; $R^2$ is a hydrogen atom; $R^3$ is a hydrogen atom or $C_{1-6}$ alkyl; m is 1; ring Aa is a 5-membered ring optionally having 1 or 2 substituents selected from optionally halogenated $C_{1-6}$ alkyl, $C_{1-6}$ alkyl optionally having 1 or 2 $C_{6-10}$ aryl and optionally halogenated $C_{1-6}$ alkoxy-carbonyl; ring Ba is a 6-membered ring optionally having 1 or 2 halogen atoms; ring Ca is a 5-membered ring optionally having one substituent selected from optionally halogenated $C_{1-6}$ alkyl, optionally halogenated $C_{3-6}$ cycloalkyl, optionally halogenated $C_{6-10}$ aryl, optionally halogenated $C_{7-12}$ aralkyl and optionally halogenated 5- or 6-membered heterocyclic group, and the like can be mentioned.

As compound (I), the compounds described in Examples 1 to 34 are specifically preferable. Particularly,
N-[2-(2-methyl-6,7-dihydrocyclopenta[e]indazol-8(2H)-ylidene)ethyl]acetamide,
N-[2-(2-methyl-2,6,7,8-tetrahydrocyclopenta[e]indazol-8-yl)ethyl]acetamide,
N-[2-(2-methyl-2,6,7,8-tetrahydrocyclopenta[e]indazol-8-yl)ethyl]propanamide,
N-[2-(1-fluoro-2-methyl-2,6,7,8-tetrahydrocyclopenta[e]indazol-8-yl)ethyl]acetamide,
N-[2-(1-chloro-2-methyl-2,6,7,8-tetrahydrocyclopenta[e]indazol-8-yl)ethyl]acetamide,
N-[2-(5-fluoro-2-methyl-2,6,7,8-tetrahydrocyclopenta[e]indazol-8-yl)ethyl]acetamide,
N-[2-(5-chloro-2-methyl-2,6,7,8-tetrahydrocyclopenta[e]indazol-8-yl)ethyl]acetamide,
N-[2-(2-methyl-8,9-dihydro-7H-cyclopenta[c]pyrazolo[1,5-a]pyridin-9-yl)ethyl]acetamide,
N-[2-(2-methyl-8,9-dihydro-7H-cyclopenta[c]pyrazolo[1,5-a]pyridin-9-yl)ethyl]propanamide,
N-[2-(2-methyl-7,8-dihydro-6H-cyclopenta[e]imidazo[1,2-a]pyridin-8-yl)ethyl]acetamide, and salts thereof are preferable.

As a salt of compound (I), for example, a pharmacologically acceptable salt and the like are used. For example, a salt with inorganic base, a salt with organic base, a salt with inorganic acid, a salt with organic acid, a salt with basic or acidic amino acid and the like can be mentioned. Preferable examples of salts with inorganic base include alkali metal salt such as sodium salt, potassium salt and the like, alkaline earth metal salt such as calcium salt, magnesium salt and the like, and aluminum salt, ammonium salt and the like. Preferable examples of salts with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of salts with inorganic acid include salts with hydrochloric acid, hydrobromic acid, nitric acid, sulfuric acid, phosphoric acid and the like. Preferable examples of salts with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of salts with basic amino acid include salts with arginine, lysine, ornithine and the like, and preferable examples of salts with acidic amino acid include salts with aspartic acid, glutamic acid and the like. Of these, a pharmaceutically acceptable salt is preferable. Examples thereof when compound (I) has a basic functional group include salts with inorganic acid such as hydrochloric acid, hydrobromic acid, nitric acid, sulfuric acid, phosphoric acid and the like, and salts with organic acid such as acetic acid, phthalic acid, fumaric acid, tartaric acid, maleic acid, citric acid, succinic acid, methanesulfonic acid, p-toluenesulfonic acid and the like. Examples thereof when compound (I) has an acidic functional group include alkali metal salts such as sodium salt, potassium salt and the like, alkaline earth metal salts such as calcium salt, magnesium salt and the like, ammonium salt and the like.

The production methods of compound (I) are described in the following.

The following compounds (II)-(XXXVII) include salts thereof. As the salt, for example, one similar to the salt of compound (I) and the like are used.

The compound obtained in each step can be directly used as a reaction mixture or a crude product for the next reaction. It can be isolated from a reaction mixture according to a conventional method, and can be easily purified by a separation means such as recrystallization, distillation, chromatography and the like.

The reaction schemes thereof are shown below, wherein each symbol of the compound is as defined above. In the formulas,
$R^{4a-4r}$ are each a hydrogen atom, a hydrocarbon group optionally having substituent(s) or a heterocyclic group optionally having substituent(s),
$R^{5a-5l}$ are each a hydrogen atom or a hydrocarbon group optionally having substituent(s), and
Y is a halogen atom.

From among those recited as examples of the solvents used for the production methods of compound (I), the following solvents are specifically used.
alcohols:
methanol, ethanol, 1-propanol, 2-propanol, tert-butyl alcohol and the like
ethers:
diethyl ether, diisopropyl ether, diphenyl ether, tetrahydrofuran, 1,4-dioxane, 1,2-dimethoxyethane and the like
aromatic hydrocarbons:
benzene, toluene, xylene and the like
saturated hydrocarbons:
cyclohexane, hexane and the like amides:
N,N-dimethylformamide, N,N-dimethylacetamide, hexamethylphosphoric triamide and the like
halogenated hydrocarbons:
dichloromethane, chloroform, carbon tetrachloride, 1,2-dichloroethane and the like
nitriles:
acetonitrile, propionitrile and the like
sulfoxides:
dimethyl sulfoxide and the like
acid anhydrides:
acetic anhydride and the like
organic acids:
formic acid, acetic acid, propionic acid, trifluoroacetic acid, methanesulfonic acid and the like
inorganic acids:
sulfuric acid and the like
esters:
methyl acetate, ethyl acetate, butyl acetate and the like
ketones:
acetone, methyl ethyl ketone and the like
aromatic organic bases:
pyridine, lutidine and the like From among those recited as examples of the halogenating agent used for the production methods of compound (I), the following halogenating agents are specifically used.
phosphorus halide:
phosphorus trichloride, phosphorus oxychloride, phosphorus pentachloride, phosphorus tribromide, phosphorus triiodide and the like
succinimides:
bromosuccinimide, iodosuccinimide and the like
halogen:
chlorine, bromine, iodine, iodine monofluoride, iodine monochloride and the like
hydrogen halide:
hydrochloric acid, hydrobromic acid, hydriodic acid and the like
halide salt:
sodium chloride, sodium bromide, potassium iodide and the like From among those recited as examples of the base and deacidifying agent used for the production methods of compound (I), the following bases and deacidifying agents are specifically used.
inorganic bases:
sodium hydroxide, potassium hydroxide, magnesium hydroxide and the like
basic salts:
sodium carbonate, potassium carbonate, cesium carbonate, calcium carbonate, sodium hydrogen carbonate and the like
organic bases:
triethylamine, diisopropylethylamine, tributylamine, cyclohexyldimethylamine, pyridine, lutidine, 4-dimethylaminopyridine, N,N-dimethylaniline, N-methylpiperidine, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene and the like
metal alkoxides:
sodium methoxide, sodium ethoxide, potassium tert-butoxide and the like
alkali metal hydrides:
sodium hydride, potassium hydride and the like
metal amides:
sodium amide, lithium diisopropylamide, lithium hexamethyldisilazide and the like
organic lithiums:
methyllithium, n-butyllithium, sec-butyllithium, tert-butyllithium and the like From among those recited as examples of the acids used for the production methods of compound (I), the following acids are specifically used.
inorganic acids:
hydrochloric acid, sulfuric acid, nitric acid, hydrobromic acid, phosphoric acid and the like
organic acids:
acetic acid, trifluoroacetic acid, oxalic acid, phthalic acid, fumaric acid, tartaric acid, maleic acid, citric acid, succinic acid, methanesulfonic acid, p-toluenesulfonic acid, 10-camphorsulfonic acid and the like From among those recited as examples of the metal catalysts used for the production methods of compound (I), the following metal catalysts are specifically used.
palladium compound:
palladium(II) acetate, tetrakis(triphenylphosphine)palladium(0), bis(triphenylphosphine)palladium(II) chloride, dichlorobis(triethylphosphine)palladium(II), tris(dibenzylideneacetone)dipalladium(0), [2,2'-bis(diphenylphosphino)-1,1'-binaphthyl]palladium(II) chloride, complex of palladium(II) acetate and 1,1'-bis(diphenylphosphino)ferrocene, and the like
nickel compound:
tetrakis(triphenylphosphine)nickel(0), bis(triethylphosphine)nickel(II) chloride, bis(triphenylphosphine)nickel(II) chloride
rhodium compound:
tris(triphenylphosphine)rhodium(III) chloride and the like
copper compound:
copper oxide, copper(II) chloride and the like From among those recited as examples of the reducing agents used for the production methods of compound (I), the following reducing agents are specifically used.
metal hydride:
aluminum hydride, diisobutylaluminum hydride, tributyltin hydride and the like
metal hydride complex compound:
sodium cyanoborohydride, sodium triacetoxyborohydride, sodium borohydride, lithium aluminum hydride and the like
borane complex:
borane tetrahydrofuran complex, borane dimethyl sulfide complex and the like
alkylboranes:
thexylborane, disiamylborane and the like
metals:
zinc, aluminum, tin, iron and the like
(Reaction 01)

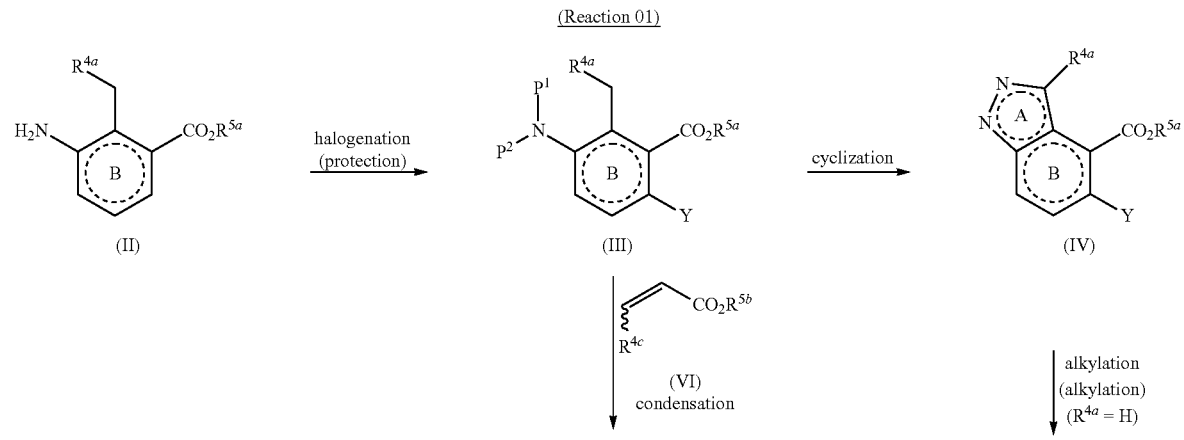

-continued
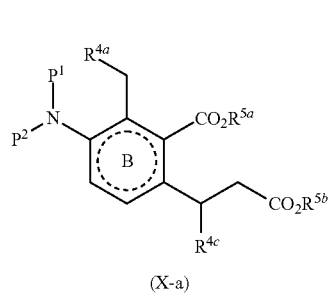
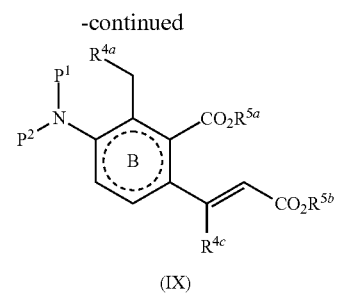
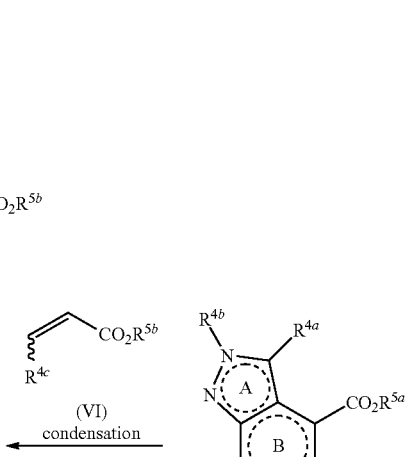
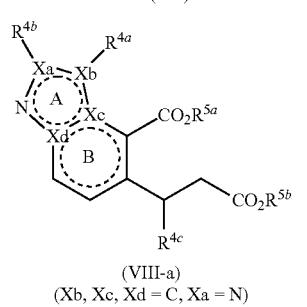
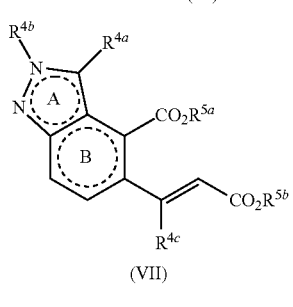
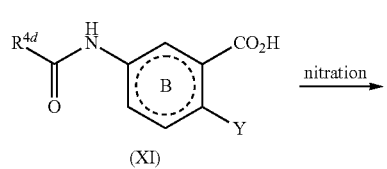
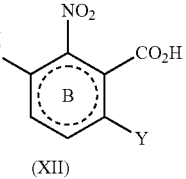
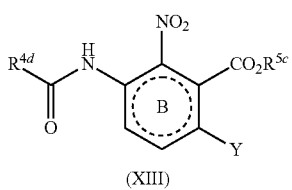
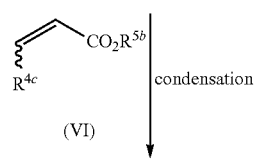
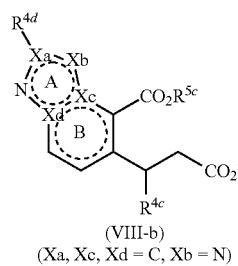
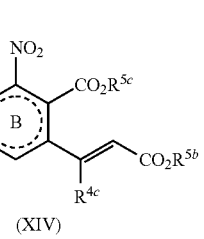
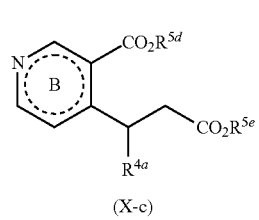
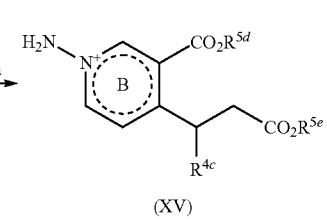
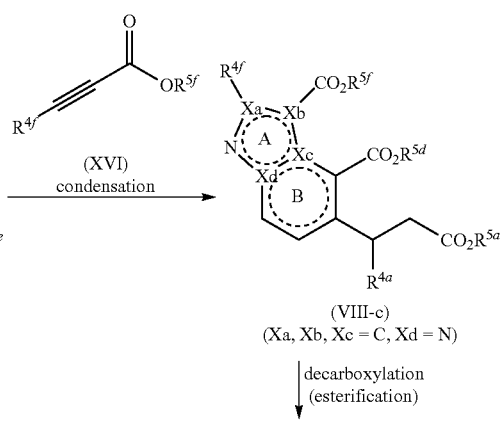

-continued
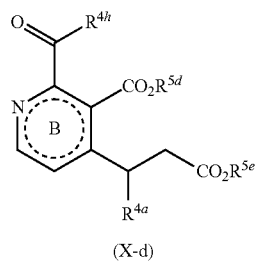
(X-d)
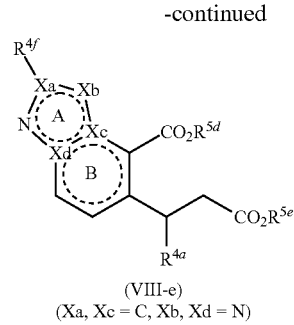
(VIII-e)
(Xa, Xc = C, Xb, Xd = N)
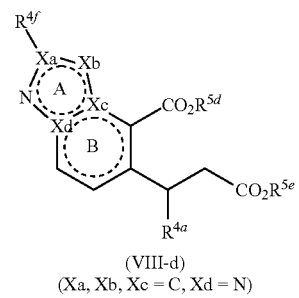
(VIII-d)
(Xa, Xb, Xc = C, Xd = N)
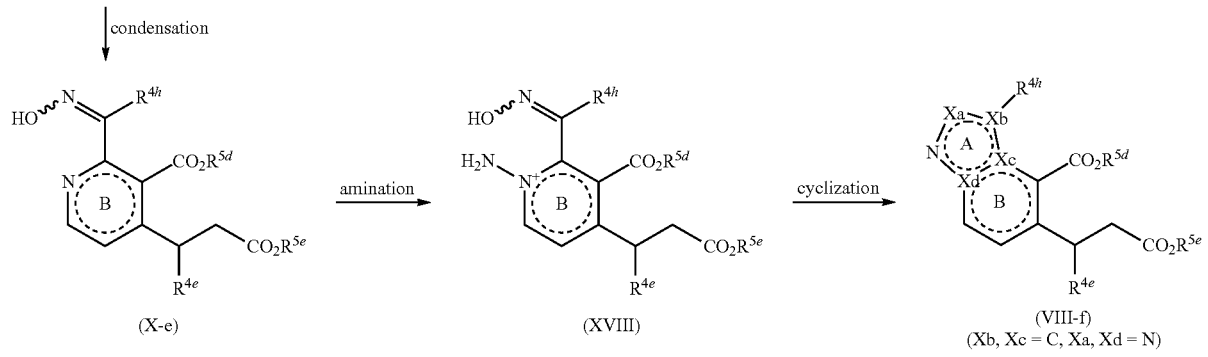
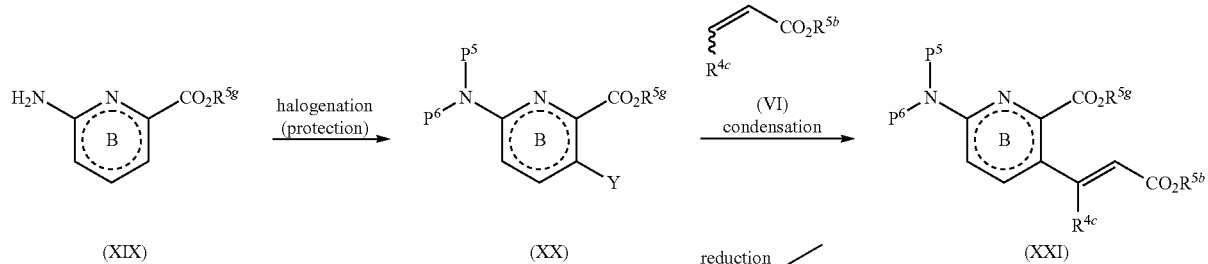
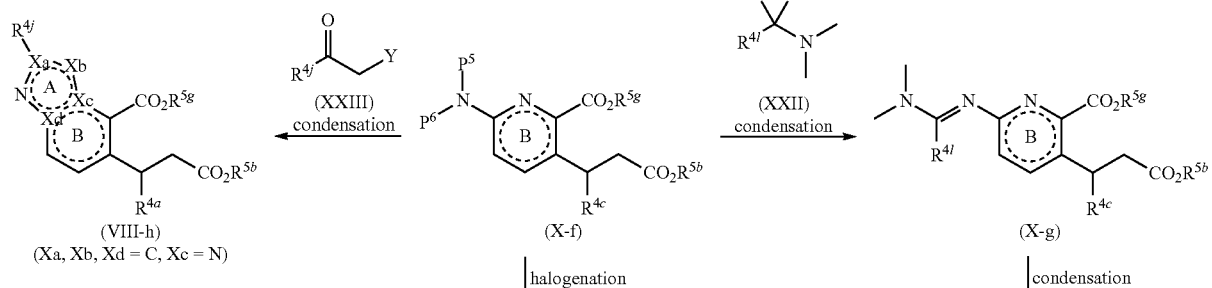
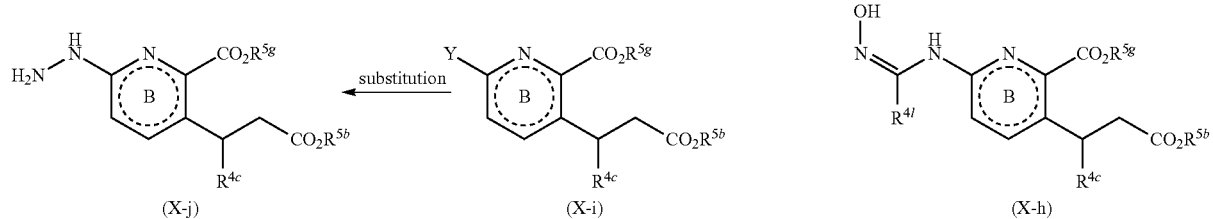

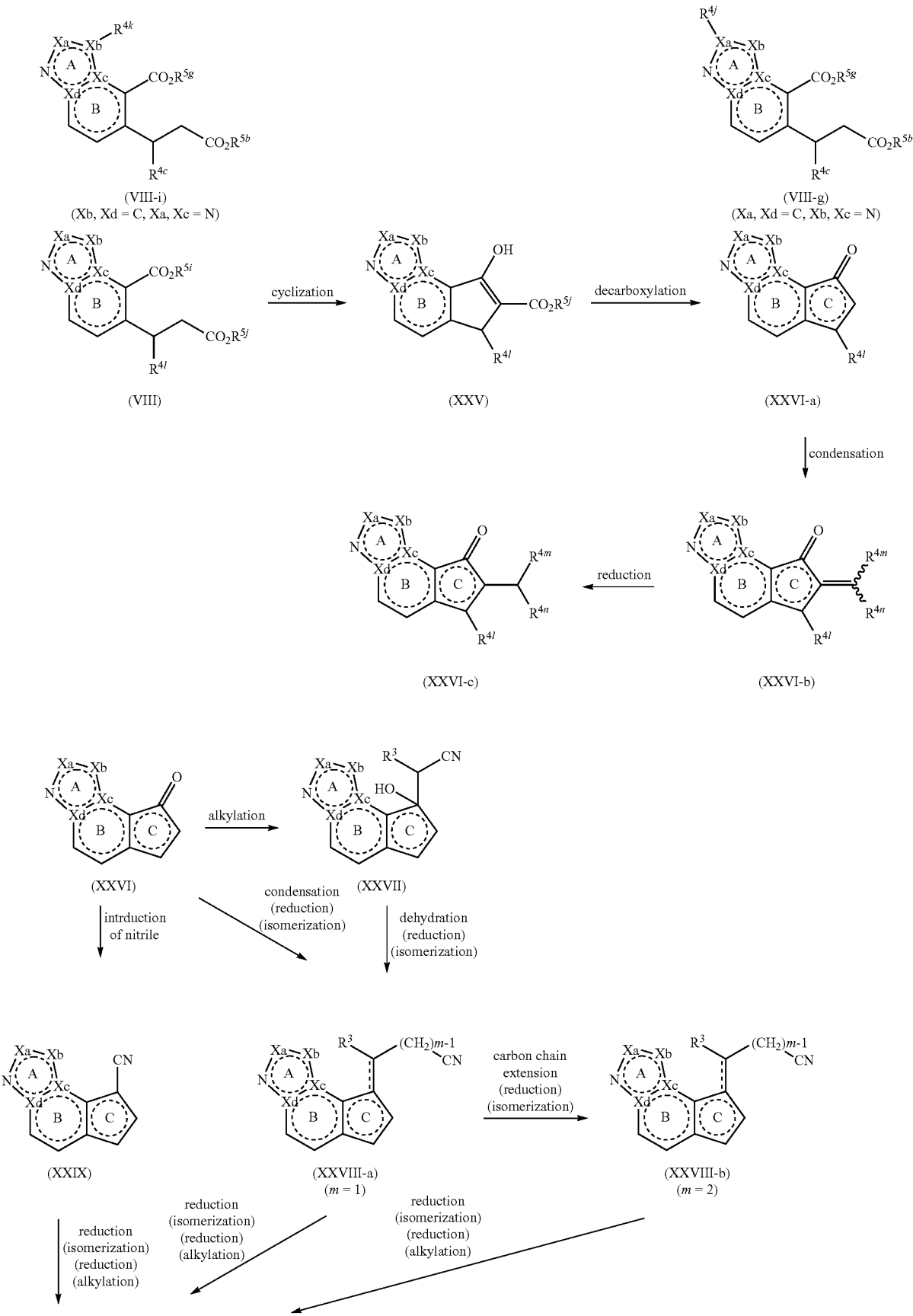

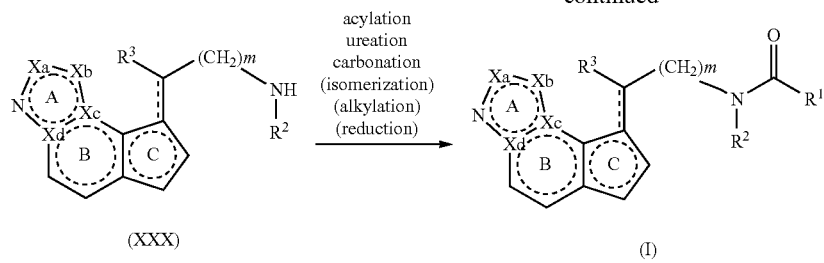

(XXX) → (I)

Compound (X-c) can be produced according to a method known per se, for example, the method described in J. Org. Chem., vol. 58, page 3162 (1993), Monatsh. Chem., vol. 105, page 196 (1974) and the like, or a method analogous thereto.

Compounds (II), (VI), (XI), (XVI), (XIX), (XVII), (XXII), (XXIII) and (XXIV) can be produced according to a method known per se, or a method analogous thereto.

When the compounds used in the explanation of the present production methods are commercially available, such commercially available products can also be used directly.

Compound (III) can be produced by reacting compound (II) with a halogenating agent. Examples of the halogenating agent include phosphorus halide, succinimides, halogen, thionyl chloride, and mixtures thereof and the like. The halogenating agent is used in an amount of about 1.0 to 100 mol, preferably about 1.0 to 10 mol, per 1 mol of compound (II). To promote the reaction, the reaction can be performed in the presence of a base. Examples of the base include inorganic bases, basic salts and the like. This reaction is advantageously performed without solvent or in a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons, nitriles, sulfoxides, acid anhydrides, organic acids, inorganic acids, water and the like or a mixed solvent thereof and the like are preferable. While the reaction time varies depending on the reagent and solvent to be used, it is generally 10 min to 50 hr, preferably 30 min to 12 hr. The reaction temperature is generally 0° C. to 200° C., preferably 10° C. to 100° C.

Amino of compound (III) may be protected as desired by a group represented by $P^1$ or $P^2$ [wherein $P^1$ and $P^2$ are the same or different and each is i) a hydrogen atom, ii) formyl, or iii) $C_{1-6}$ alkyl-carbonyl (e.g., acetyl, propionyl and the like), benzoyl, $C_{1-6}$ alkoxy-carbonyl (e.g., methoxycarbonyl, ethoxycarbonyl, tert-butoxycarbonyl (Boc) and the like), allyloxycarbonyl (Aloc), phenoxycarbonyl, fluorenylmethyloxycarbonyl (Fmoc), $C_{7-10}$ aralkyl-carbonyl (e.g., benzylcarbonyl and the like), $C_{7-10}$ aralkyloxy-carbonyl (e.g., benzyloxycarbonyl (Z) and the like), $C_{7-10}$ aralkyl (e.g., benzyl and the like), trityl, phthaloyl or N,N-dimethylaminomethylene, each optionally having substituent(s), and the like. As the substituent, 1 to 3 substituents selected from phenyl, a halogen atom (e.g., fluorine, chlorine, bromine, iodine and the like), $C_{1-6}$ alkyl-carbonyl (e.g., methylcarbonyl, ethylcarbonyl, butylcarbonyl and the like), nitro and the like can be mentioned]. The group represented by $P^1$ or $P^2$ can be introduced by a method known per se, for example, the method described in Wiley-Interscience, 1999, "Protective Groups in Organic Synthesis, $3^{rd}$ Ed." (by Theodora W. Greene, Peter G. M. Wuts) and the like.

Compound (IV) can by produced by reacting compound (III) with a diazotizing reagent in the presence of an acid. Examples of the acid include inorganic acids, organic acids, boron trifluoride ether complex and the like. Examples of the diazotizing reagent include nitrous acid, nitrite salts such as sodium nitrite, potassium nitrite etc., nitrous acid esters such as ethyl nitrite, amyl nitrite etc., and the like. The acid is used in an amount of about 2.0 to 200 mol, preferably about 5.0 to 100 mol, per 1 mol of compound (III). The diazotizing reagent is used in an amount of about 1.0 to 20 mol, preferably about 1.0 to 3.0 mol, per 1 mol of compound (III). This reaction is advantageously performed in a solvent inert to the reaction. While the solvent is not particularly limited as long as the reaction proceeds, a solvent such as alcohols, ethers, halogenated hydrocarbons, acid anhydrides, organic acids, inorganic acids, water and the like, or a mixed solvent thereof and the like are preferable. While the reaction time varies depending on the reagent and solvent to be used, it is generally 10 min to 170 hr, preferably 1 hr to 80 hr. The reaction temperature is generally 0° C. to 100° C., preferably 0° C. to 30° C.

Compound (IV) can also be produced according to a method known per se, for example, the method described in J. Heterocyclic Chem., vol. 21, p. 1063 (1984) and the like or a method analogous thereto.

Compound (V) can by produced by reacting compound (IV) with an alkylating agent. Examples of the alkylating agent include trimethyloxonium tetrafluoroborate, triethyloxonium hexafluorophosphate and the like. The alkylating agent is used in an amount of about 1.0 to 50 mol, preferably about 1.0 to 3.0 mol, per 1 mol of compound (1V). This reaction is advantageously performed in a solvent inert to the reaction. While the solvent is not particularly limited as long as the reaction proceeds, a solvent such as ethers, halogenated hydrocarbons, esters, ketones and the like or a mixed solvent thereof and the like are preferable. While the reaction time varies depending on the reagent and solvent to be used, it is generally 10 min to 30 hr, preferably 1 hr to 10 hr. The reaction temperature is generally 0° C. to 100° C., preferably 0° C. to 30° C.

Compound (V) can also be produced according to a method known per se, for example, the method described in J. Chem. Soc. Perkin Trans. 1, p. 2371 (1973) and the like, or a method analogous thereto.

Of compound (V), when desired, a compound wherein $R^{4a}$ is a hydrogen atom can be subjected to an alkylation reaction in the presence of a base using an alkylating agent (e.g. alkyl halide represented by $R^{4a}X$ wherein X is a halogen atom, and the like). Examples of the base include inorganic bases, basic salts, organic bases, metal alkoxides, alkali metal hydrides, metal amides and the like. The base is used in an amount of about 1.0 to 5.0 mol, preferably about 1.0 to 2.0 mol, per 1 mol of compound (V). This reaction is advantageously performed in a solvent inert to the reaction. While the solvent is not particularly limited as long as the reaction proceeds, a solvent such as ethers, aromatic hydrocarbons, saturated hydrocarbons, amides, halogenated hydrocarbons, nitrites, sulfoxides and the like or a mixed solvent thereof and the like are preferable. While the reaction time varies depending on the reagent and solvent to be used, it is generally 30 min to 48 hr, preferably 30 min to 6 hr. The reaction temperature is generally −20° C. to 200° C., preferably −10° C. to 150° C.

Alkyl halide represented by $R^{4a}X$ may be a commercially available product or can also be produced according to a method known per se or a method analogous thereto.

Compound (VII) can be produced by condensing compound (V) and compound (VI) in the presence of a metal catalyst. As the metal catalyst, various metal complexes having ligand are used and, for example, palladium compound, nickel compound, rhodium compound, cobalt compound, copper compound, platinum compound and the like can be mentioned. Among these, palladium compound, nickel compound and copper compound are preferable. Compound (VI) is used in an amount of about 0.8 to 10 mol, preferably about 1.0 to 3.0 mol, per 1 mol of compound (V). The metal catalyst is used in an amount of about 0.000001 to 5 mol, preferably about 0.0001 to 1 mol, per 1 mol of compound (V). This reaction is preferably performed in the presence of a base. Examples of the base include inorganic bases, basic salts, organic bases, metal alkoxides, alkali metal hydrides, metal amides and the like. The base is used in an amount of about 1.0 to 20 mol, preferably about 1.0 to 5.0 mol, per 1 mol of compound (V). When a metal catalyst unstable to oxygen is used for this reaction, the reaction is preferably performed, for example, in an inert gas stream such as argon gas, nitrogen gas and the like. This reaction is advantageously performed using a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons, nitrites, sulfoxides, esters, water and the like or a mixed solvent thereof and the like are preferable. While the reaction time varies depending on the reagent and solvent to be used, it is generally 10 min to 100 hr, preferably 30 min to 50 hr. The reaction temperature is −10° C. to 250° C., preferably 0° C. to 150° C.

Compound (VIII-a) wherein Xb, Xc and Xd are carbon atoms and Xa is a nitrogen atom can be produced by subjecting compound (VII) to a reduction reaction. The reduction reaction is performed according to a conventional method and generally using a reducing agent. Examples of the reducing agent include metal hydride, metal hydride complex compound, borane complex, alkylboranes, diborane, metals, alkali metal (e.g., sodium, lithium and the like)/liquid ammonia (Birch reduction) and the like. The amount of the reducing agent to be used is appropriately determined according to the kind of the reducing agent. For example, metal hydride, metal hydride complex compound, borane complex, alkylboranes or diborane is used in an amount of about 0.25 to 10 mol, preferably about 0.5 to 5 mol, per 1 mol of compound (VII), and metal (including alkali metal to be used for Birch reduction) is used in an amount of about 1.0 to 20 mol, preferably about 1.0 to 5.0 mol, per 1 mol of compound (VII). This reaction is advantageously performed using a solvent inert to the reaction. While the solvent is not particularly limited as long as the reaction proceeds, for example, solvents such as alcohols, ethers, aromatic hydrocarbons, amides, halogenated hydrocarbons, organic acids, water and the like or a mixed solvent thereof and the like are preferable. While the reaction time varies depending on the reagent and solvent to be used, it is generally 10 min to 100 hr, preferably 30 min to 50 hr. The reaction temperature is −20° C. to 100° C., preferably 0° C. to 80° C.

In addition, the reduction reaction can also be performed by a hydrogenation reaction. In this case, for example, a catalyst such as palladium carbon, platinum(IV) oxide, Raney nickel, Raney cobalt etc., or the like is used. The catalyst is used in an amount of about 1.0 to 300 wt %, preferably about 10 to 20 wt %, relative to compound (VII). Various hydrogen sources can also be used instead of gaseous hydrogen. As the hydrogen source, for example, formic acid, ammonium formate, triethylammonium formate, sodium phosphinate, hydrazine and the like are used. The hydrogen source is used in an amount of about 1.0 to 10 mol, preferably about 1.0 to 5.0 mol, per 1 mol of compound (VII). This reaction is advantageously performed using a solvent inert to the reaction. For example, solvents such as alcohols, ethers, aromatic hydrocarbons, saturated hydrocarbons, amides, halogenated hydrocarbons, esters, organic acids, water and the like or a mixed solvent thereof and the like are preferable. While the reaction time varies depending on the kind and amount of the reducing agent or the activity and amount of the catalyst to be used, it is generally 30 min to 100 hr, preferably 1 hr to 50 hr. The reaction temperature is generally −20° C. to 120° C., preferably 0° C. to 80° C. When a hydrogenation catalyst is used, the pressure of hydrogen is generally 1 to 100 atm.

Compound (IX) can be produced by condensing compound (III) and compound (VI) in the presence of a metal catalyst. The condensation reaction can be performed by a method similar to the method of producing compound (VII) from compound (V).

Compound (X-a) can be produced by subjecting compound (IX) to a reduction reaction. The reduction reaction can be performed by a method similar to the method of producing compound (VIII-a) from compound (VII).

Compound (XII) can be produced by reacting compound (XI) with a nitrating reagent. Examples of the nitrating reagent include metal nitrate salts such as sodium nitrate, potassium nitrate and the like, acetyl nitrate, dinitrogen pentoxide, nitronium salt, nitric acid, mixed acid (mixture of nitric acid and sulfuric acid), and a mixture thereof. The nitrating reagent is used in an amount of about 0.8 to 20 mol, preferably about 1.0 to 2.0 mol, per 1 mol of compound (XI). When nitric acid, mixed acid and the like are used as nitrating reagents, an excess amount thereof can also be used as a reaction solvent. This reaction is advantageously performed in a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons, nitrites, sulfoxides, acid anhydrides, organic acids, inorganic acids and the like or a mixed solvent thereof and the like are preferable. While the reaction time varies depending on the reagent and solvent to be used, it is generally 10 min to 24 hr, preferably 30 min to 12 hr. The reaction temperature is −10° C. to 150° C., preferably 0° C. to 80° C.

Compound (XIII) can be produced by subjecting compound (XII) to an esterification reaction. The esterification reaction can be performed according to, for example, the method described in 4th Ed. Jikken Kagaku Koza (Courses in Experimental Chemistry), vol. 22, pages 43-54 (The Chemical Society of Japan Ed.), or a method analogous thereto.

Compound (XIV) can be produced by condensing compound (XIII) and compound (VI) in the presence of a metal catalyst. The condensation reaction can be performed by a method similar to the method of producing compound (VII) from compound (V).

Compound (X-b) can be produced by subjecting compound (XIV) to a reduction reaction. The reduction reaction can be performed by a method similar to the method of producing compound (VIII-a) from compound (VII).

Amino of compound (X-b) may be protected as desired by a group represented by $P^3$ or $P^4$ [wherein $P^3$ and $P^4$ are the same or different and each is i) a hydrogen atom, ii) formyl, or iii) $C_{1-6}$ alkyl-carbonyl (e.g., acetyl, propionyl and the like), benzoyl, $C_{1-6}$ alkoxy-carbonyl (e.g., methoxycarbonyl, ethoxycarbonyl, tert-butoxycarbonyl (Boc) and the like), allyloxycarbonyl (Aloc), phenoxycarbonyl, fluorenylmethyloxycarbonyl (Fmoc), $C_{7-10}$ aralkyl-carbonyl (e.g., benzylcarbonyl and the like), $C_{7-10}$ aralkyloxy-carbonyl (e.g., benzyloxycarbonyl (Z) and the like), $C_{7-10}$ aralkyl (e.g., benzyl and the like), trityl, phthaloyl or N,N-dimethylaminomethylene, each optionally having substituent(s), and the like. As the substituent, 1 to 3 substituents selected from phenyl, a halogen atom (e.g., fluorine, chlorine, bromine, iodine and the like), $C_{1-6}$ alkyl-carbonyl (e.g., methylcarbonyl, ethylcarbonyl, butylcarbonyl and the like), nitro and the like can be mentioned]. The group represented by $P^3$ or $P^4$ can be introduced by a method known per se, for example, the method described in Wiley-Interscience, 1999, "Protective Groups in Organic Synthesis, $3^{rd}$ Ed." (by Theodora W. Greene, Peter G. M. Wuts) and the like.

Compound (VIII-b) wherein Xa, Xc and Xd are carbon atoms, and Xb is a nitrogen atom can be produced by subjecting compound (X-b) to a cyclization reaction. For cyclization reaction, for example, a method by heating, a method using an acid, a method analogous thereto and the like are used. For ring closure by heating, the reaction is advantageously performed without solvent or in a solvent inert to the reaction. While the solvent is not particularly limited as long as the reaction proceeds, for example, solvents such as ethers, aromatic hydrocarbons, amides, halogenated hydrocarbons, organic acids, inorganic acids, water and the like or a mixed solvent thereof and the like are preferable. While the reaction time varies depending on the reagent and solvent to be used, it is generally 10 min to 100 hr, preferably 1 hr to 10 hr. The reaction temperature is 50° C. to 300° C., preferably 100° C. to 200° C.

When acid is used for ring closure, for example, inorganic acids, organic acids, boron fluoride ether complex and the like are used. The acid is used in an amount of about 0.05 to 100 mol, preferably about 0.1 to 10 mol, per 1 mol of compound (X-b). This reaction is advantageously performed without solvent or in a solvent inert to the reaction. While the solvent is not particularly limited as long as the reaction proceeds, for example, solvents such as ethers, aromatic hydrocarbons, saturated hydrocarbons, amides, halogenated hydrocarbons, sulfoxides, organic acids, inorganic acids, water and the like or a mixed solvent thereof and the like are preferable. While the reaction time varies depending on the reagent and solvent to be used, it is generally 10 min to 100 hr, preferably 30 min to 12 hr. The reaction temperature is 0° C. to 200° C., preferably 0° C. to 150° C.

Compound (XV) can be produced by reacting compound (X-c) with an amination reagent. Examples of the amination reagent include O-mesitylenesulfonylhydroxylamine, O-(2,4-dinitrophenyl)hydroxylamine, and a mixture thereof. These reagents can be produced according to the method described in, for example, J. Org. Chem., vol. 38, page 1239 (1973), J. Org. Chem., vol. 68, page 7119 (2003) and the like, or a method analogous thereto. The amination reagent is used in an amount of about 1.0 to 20 mol, preferably about 1.0 to 3.0 mol, per 1 mol of compound (X-c). This reaction is advantageously performed in a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons, nitrites, sulfoxides and the like or a mixed solvent thereof and the like are preferable. While the reaction time varies depending on the reagent and solvent to be used, it is generally 10 min to 170 hr, preferably 1 hr to 80 hr. The reaction temperature is 0° C. to 150° C., preferably 20° C. to 80° C.

Compound (VIII-c) wherein Xa, Xb and Xc are carbon atoms, and Xd is a nitrogen atom can be produced by condensing compound (XV) and compound (XVI) in the presence of a base. Examples of the base include inorganic bases, basic salts, organic bases, metal alkoxides and the like. The base used in an amount of about 1.0 to 20 mol, preferably about 1.0 to 5.0 mol, per 1 mol of compound (XV). Compound (XVI) is used in an amount of about 1.0 to 20 mol, preferably about 1.0 to 5.0 mol, per 1 mol of compound (XV). This reaction is advantageously performed in a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons, nitrites, sulfoxides and the like or a mixed solvent thereof and the like are preferable. While the reaction time varies depending on the reagent and solvent to be used, it is generally 10 min to 50 hr, preferably 1 hr to 25 hr. The reaction temperature is generally −20° C. to 150° C., preferably 0° C. to 80° C.

Compound (VIII-d) wherein Xa, Xb and Xc are carbon atoms, and Xd is a nitrogen atom can be produced by subjecting compound (VIII-c) to a decarboxylation reaction. The decarboxylation reaction can be performed according to a method known per se, or a method analogous thereto and, for example, a method using an acid, a method analogous thereto and the like can be mentioned. Examples of the acid include inorganic acids, organic acids and the like. The acid is used in an amount of about 0.0001 to 20 mol, preferably about 0.01 to 5.0 mol, per 1 mol of compound (VIII-c). This reaction is advantageously performed without solvent or in a solvent inert to the reaction. While the solvent is not particularly limited as long as the reaction proceeds, for example, alcohols, solvents such as ethers, aromatic hydrocarbons, saturated hydrocarbons, amides, halogenated hydrocarbons, sulfoxides, organic acids, inorganic acids, water and the like or a mixed solvent thereof and the like are preferable. While the reaction time varies depending on the reagent and solvent to be used, it is generally 10 min to 200 hr, preferably 30 min to 100 hr. The reaction temperature is generally 0° C. to 200° C., preferably 0° C. to 150° C.

Of compound (VIII-d), an ester form of a compound wherein one or both of $R^{5d}$ and $R^{5e}$ is/are hydrogen atom(s) can be produced by subjected the compound to esterification. The esterification reaction can be performed according to, for example, the method described in 4th Ed. Jikken Kagaku Koza (Courses in Experimental Chemistry), vol. 22, pages 43-54 (The Chemical Society of Japan Ed.), or a method analogous thereto.

Compound (VIII-e) wherein Xa and Xc are carbon atoms, and Xb and Xd are nitrogen atoms can be produced by condensing compound (XV) and compound (XVII) in the presence of a base. Examples of the base include inorganic bases, basic salts, organic bases, metal alkoxides and the like. The base used in an amount of about 1.0 to 20 mol, preferably about 1.0 to 5.0 mol, per 1 mol of compound (XV). Compound (XVII) is used in an amount of about 1.0 to 20 mol, preferably about 1.0 to 5.0 mol, per 1 mol of compound (XV). This reaction is advantageously performed in a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons, nitriles, sulfoxides and the like or a mixed solvent thereof and the like are preferable. While the reaction time varies depending on the reagent and solvent to be used, it is generally 10 min to 50 hr, preferably 1 hr to 25 hr. The reaction temperature is generally −20° C. to 150° C., preferably 0° C. to 80° C.

Compound (X-d) can be produced by reacting compound (X-c) with a formylating reagent or an acylating reagent in the presence of a base. Examples of the base include organic bases, metal alkoxides, alkali metal hydrides, metal amides, organic lithiums and the like. Examples of the formylating reagent include N,N-dimethylformamide, N-formylpiperidine, N-formylmorpholine, formic acid esters such as ethyl formate etc., and the like, and examples of the acylating reagent include amides such as N,N-dimethylbenzamide etc., and the like. The base is used in an amount of about 1.0 to 50 mol, preferably about 1.0 to 10 mol, per 1 mol of compound (X-c). The formylating reagent and acylating reagent are each used in an amount of about 1.0 to 50 mol, preferably about 1.0 to 10 mol, per 1 mol of compound (X-c). This reaction is advantageously performed in a solvent inert to the reaction. While the solvent is not particularly limited as long as the reaction proceeds, for example, solvents such as ethers, halogenated hydrocarbons, aromatic hydrocarbons, saturated hydrocarbons and the like or a mixed solvent thereof and the like are preferable. While the reaction time varies depending on the reagent and solvent to be used, it is generally 10 min to 24 hr, preferably 30 min to 10 hr. The reaction temperature is generally −78° C. to 50° C., preferably −78° C. to 25° C.

Compound (X-d) can also be produced according to a method known per se, for example, the method described in J. Chem. Soc. Perkin Trans. 1, page 3597 (1997), J. Org. Chem, vol. 56, page 2866 (1991) and the like, or a method analogous thereto.

Compound (X-e) can be produced by condensing compound (X-d) and hydroxylamine in the presence of an acid or a base. Examples of the hydroxylamine include aqueous hydroxylamine solution, hydroxylammonium chloride, hydroxylammonium oxalate, hydroxylammonium phosphate, hydroxylammonium sulfate and the like. Examples of the acid include inorganic acids, organic acids, boron trifluoride ether complex and the like. Examples of the base include inorganic bases, basic salts, organic bases, metal alkoxides, alkali metal hydrides, metal amides, organic lithiums and the like. Hydroxylamines are used in an amount of about 1.0 to 20 mol, preferably about 2.0 to 10 mol, per 1 mol of compound (X-d). The acid is used in an amount of about 0.1 to 200 mol, preferably about 0.1 to 100 mol, per 1 mol of compound (X-d). The base is used in an amount of about 0.1 to 200 mol, preferably about 0.1 to 100 mol, per 1 mol of compound (X-d). This reaction is advantageously performed in a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons, nitriles, sulfoxides, esters, ketones, aromatic organic bases, acid anhydrides, organic acids, inorganic acids, water and the like or a mixed solvent thereof and the like are preferable. While the reaction time varies depending on the reagent and solvent to be used, it is generally 10 min to 170 hr, preferably 1 hr to 80 hr. The reaction temperature is generally 0° C. to 250° C., preferably 0° C. to 200° C. In addition, microwave irradiation may be used to promote the reaction.

Compound (X-e) can also be produced according to a method known per se, for example, the method described in 4th Ed. Jikken Kagaku Koza (Courses in Experimental Chemistry), vol. 20, pages 353-354 (The Chemical Society of Japan Ed.) and the like, or a method analogous thereto.

Compound (XVIII) can be produced by reacting compound (X-e) with an amination reagent. The amination reaction can be performed by a method similar to the method of producing compound (XV) from compound (X-c).

Compound (VIII-f) wherein Xb and Xc are carbon atoms, and Xa and Xd are nitrogen atoms can be produced by subjecting compound (XVIII) to a cyclization reaction. For the cyclization reaction, for example, a method by heating, a method using an acid, a method using a dehydrating agent, a method analogous thereto and the like are used. The method by heating and the method using an acid can be performed by a method similar to the method of producing compound (VIII-b) from compound (X-b). When a dehydrating agent is used, examples of the dehydrating agent include diphosphorus pentoxide, phosphorus oxychloride, phosphorus pentachloride, triphenylphosphine, phosgene, N,N'-dicyclohexylcarbodiimide, alumina, sodium dioxide, thionyl chloride, methanesulfonyl chloride, p-toluenesulfonyl chloride, trifluoroacetic anhydride, acetic anhydride, acetyl chloride, polyphosphoric acid and the like. The dehydrating agent is used in an amount of about 1.0 to 100 mol, preferably about 5.0 to 30 mol, per 1 mol of compound (XVIII). This reaction is advantageously performed without solvent or in a solvent inert to the reaction. While the solvent is not particularly limited as long as the reaction proceeds, for example, solvents such as ethers, aromatic hydrocarbons, saturated hydrocarbons, halogenated hydrocarbons, ketones, acid anhydrides and the like or a mixed solvent thereof and the like are preferable. While the reaction time varies depending on the reagent and solvent to be used, it is generally 10 min to 100 hr, preferably 1 hr to 50 hr. The reaction temperature is generally 10° C. to 300° C., preferably 20° C. to 150° C.

Compound (XX) can be produced by reacting compound (XIX) with a halogenating agent. The halogenation can be performed by a method similar to the method of producing compound (III) from compound (II).

Amino of compound (XX) may be protected as desired by a group represented by $P^5$ or $P^6$ [wherein $P^5$ and $P^6$ are the same or different and each is i) a hydrogen atom, ii) formyl, or iii) $C_{1-6}$ alkyl-carbonyl (e.g., acetyl, propionyl and the like), benzoyl, $C_{1-6}$ alkoxy-carbonyl (e.g., methoxycarbonyl, ethoxycarbonyl, tert-butoxycarbonyl (Boc) and the like), allyloxycarbonyl (Aloc), phenoxycarbonyl, fluorenylmethyloxycarbonyl (Fmoc), $C_{7-10}$ aralkyl-carbonyl (e.g., benzylcarbonyl and the like), $C_{7-10}$ aralkyloxy-carbonyl (e.g., benzyloxycarbonyl (Z) and the like), $C_{7-10}$ aralkyl (e.g., benzyl and the like), trityl, phthaloyl or N,N-dimethylaminomethylene, each optionally having substituent(s), and the like. As the substituent, 1 to 3 substituents selected from phenyl, a halogen atom (e.g., fluorine, chlorine, bromine, iodine and the like), $C_{1-6}$ alkyl-carbonyl (e.g., methylcarbonyl, ethylcarbonyl, butylcarbonyl and the like), nitro and the like can be mentioned]. The group represented by $P^5$ or $P^6$ can be introduced by a method known per se, for example, the method described in Wiley-Interscience, 1999, "Protective Groups in Organic Synthesis, $3^{rd}$ Ed." (by Theodora W. Greene, Peter G. M. Wuts) and the like.

Compound (XXI) can be produced by condensing compound (XX) and compound (VI) in the presence of a metal catalyst. The condensation reaction can be performed by a method similar to the method of producing compound (VII) from compound (V).

Compound (X-f) can be produced by subjecting compound (XXI) to a reduction reaction. The reduction reaction can be performed by a method similar to the method of producing compound (VIII-a) from compound (VII).

Compound (X-g) can be produced by condensing compound (X-f) and compound (XXII) in the presence of an acid or a base. Examples of the acid include inorganic acids, organic acids, boron trifluoride ether complex and the like. Examples of the base include inorganic bases, basic salts, organic bases, metal alkoxides, alkali metal hydrides, metal amides, organic lithiums and the like. Compound (XXII) is used in an amount of about 1.0 to 20 mol, preferably about 2.0 to 10 mol, per 1 mol of compound (X-f). The acid is used in an amount of about 0.1 to 200 mol, preferably about 0.1 to 100 mol, per 1 mol of compound (X-f). The base is used in an amount of about 0.1 to 200 mol, preferably about 0.1 to 100 mol, per 1 mol of compound (X-f). This reaction is advantageously performed in a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons, nitriles, sulfoxides, esters, ketones, aromatic organic bases, acid anhydrides, organic acids, water and the like or a mixed solvent thereof and the like are preferable. While the reaction time varies depending on the reagent and solvent to be used, it is generally 10 min to 170 hr, preferably 1 hr to 80 hr. The reaction temperature is generally 0° C. to 250° C., preferably 0° C. to 200° C. In addition, microwave irradiation may be used to promote the reaction.

Compound (X-h) can be produced by condensing compound (X-g) and hydroxylamine in the presence of an acid or a base. The condensation reaction can be performed by a method similar to the method of producing compound (X-e) from compound (X-d).

Compound (VIII-g) wherein Xa and Xd are carbon atoms, and Xb and Xc are nitrogen atoms can be produced by subjecting compound (X-h) to a cyclization reaction in the presence of a dehydrating agent. Examples of the dehydrating agent include diphosphorus pentoxide, phosphorus oxychloride, phosphorus pentachloride, triphenylphosphine, phosgene, N,N'-dicyclohexylcarbodiimide, alumina, polyphosphoric acid, acetic anhydride, acetyl chloride, sodium dioxide, thionyl chloride, methanesulfonyl chloride, p-toluenesulfonyl chloride, trifluoroacetic anhydride and the like. The dehydrating agent is used in an amount of about 1.0 to 50 mol, preferably about 1.0 to 3.0 mol, per 1 mol of compound (X-h). This reaction is advantageously performed in a solvent inert to the reaction. While the solvent is not particularly limited as long as the reaction proceeds, for example, solvents such as ethers, halogenated hydrocarbons, esters, ketones and the like or a mixed solvent thereof and the like are preferable. While the reaction time varies depending on the reagent and solvent to be used, it is generally 10 min to 30 hr, preferably 1 hr to 10 hr. The reaction temperature is generally 0° C. to 150° C., preferably 0° C. to 100° C.

Compound (VIII-h) wherein Xa, Xb and Xd are carbon atoms, and Xc is a nitrogen atom can be produced by condensing compound (X-f) and compound (XXIII) in the presence of an acid or a base. Examples of the acid include inorganic acids, organic acids, boron trifluoride ether complex and the like. Examples of the base include inorganic bases, basic salts, organic bases, metal alkoxides, alkali metal hydrides, metal amides, organic lithiums and the like. Compound (XXIII) is used in an amount of about 1.0 to 20 mol, preferably about 2.0 to 10 mol, per 1 mol of compound (X-f). The acid is used in an amount of about 2.0 to 200 mol, preferably about 5.0 to 100 mol, per 1 mol of compound (X-f). The base is used in an amount of about 1.0 to 20 mol, preferably about 1.0 to 3.0 mol, per 1 mol of compound (X-f). This reaction is advantageously performed in a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons, nitriles, sulfoxides, esters, ketones, aromatic organic bases, acid anhydrides, organic acids, inorganic acids, water and the like or a mixed solvent thereof and the like are preferable. While the reaction time varies depending on the reagent and solvent to be used, it is generally 10 min to 170 hr, preferably 1 hr to 80 hr. The reaction temperature is generally 0° C. to 250° C., preferably 0° C. to 200° C. In addition, microwave irradiation may be used to promote the reaction.

Compound (X-i) can be produced by reacting compound (X-f) with a diazotizing reagent and a halogenating agent. Examples of the diazotizing reagent include nitrous acid, nitrite salts such as sodium nitrite, potassium nitrite etc., nitrous acid esters such as ethyl nitrite, amyl nitrite etc., and the like. Examples of the halogenating agent include phosphorus halide, succinimides, halogen, hydrogen halide, halide salt, thionyl chloride and a mixture thereof and the like. The diazotizing reagent is used in an amount of about 1.0 to 50 mol, preferably about 1.0 to 3.0 mol, per 1 mol of compound (X-f). The halogenating agent is used in an amount of about 2.0 to 200 mol, preferably about 5.0 to 100 mol, per 1 mol of compound (X-f). This reaction is advantageously performed in a solvent inert to the reaction. While the solvent is not particularly limited as long as the reaction proceeds, for example, solvents such as esters, ethers, halogenated hydrocarbons, ketones and the like or a mixed solvent thereof and the like are preferable. While the reaction time varies depending on the reagent and solvent to be used, it is generally 10 min to 30 hr, preferably 1 hr to 10 hr. The reaction temperature is generally 0° C. to 150° C., preferably 0° C. to 100° C.

Compound (X-j) can be produced by subjecting compound (X-i) to a substitution reaction with hydrazines. Examples of the hydrazines include aqueous hydrazine carbonate solution, hydrazine dihydrobromide dihydrate, hydrazine monohydrochloride, hydrazine dihydrochloride, hydrazine monohydrate, hydrazine monohydrobromide, hydrazine sulfate and the like. To promote the reaction, the reaction can also be performed in the presence of an acid or a base. Examples of the acid include inorganic acids, organic acids, boron trifluoride ether complex and the like. Examples of the base include inorganic bases, basic salts, organic bases, metal alkoxides, alkali metal hydrides, metal amides, organic lithiums and the like. Hydrazines are used in an amount of about 1.0 to 20 mol, preferably about 1.0 to 10 mol, per 1 mol of compound (X-i). The acid is used in an amount of about 0.1 to 200 mol, preferably about 1.0 to 100 mol, per 1 mol of compound (X-i). The base is used in an amount of about 0.1 to 200 mol, preferably about 1.0 to 100 mol, per 1 mol of compound (X-i). This reaction is advantageously performed in a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons, nitrites, sulfoxides, esters, ketones, aromatic organic bases, acid anhydrides, organic acids, inorganic acids, water and the like or a mixed solvent thereof and the like are preferable. While the reaction time varies depending on the reagent and solvent to be used, it is generally 10 min to 30 hr, preferably 1 hr to 10 hr. The reaction temperature is generally 0° C. to 150° C., preferably 0° C. to 100° C.

Compound (VIII-i) wherein Xb and Xd are carbon atoms, and Xa and Xc are nitrogen atoms can be produced by condensing compound (X-j) and compound (XXIV) in the presence of an acid or a base. Examples of the acid include inorganic acids, organic acids, boron trifluoride ether complex and the like. Examples of the base include inorganic bases, basic salts, organic bases, metal alkoxides, alkali metal hydrides, metal amides, organic lithiums and the like. Compound (XXIV) is used in an amount of about 1.0 to 20 mol, preferably about 2.0 to 10 mol, per 1 mol of compound (X-j). The acid is used in an amount of about 0.1 to 200 mol, preferably about 0.1 to 100 mol, per 1 mol of compound (X-j). The base is used in an amount of about 0.1 to 200 mol, preferably about 0.1 to 100 mol, per 1 mol of compound (X-j). This reaction is advantageously performed in a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons, nitrites, sulfoxides, esters, ketones, aromatic organic bases, acid anhydrides, organic acids, inorganic acids, water and the like or a mixed solvent thereof and the like are preferable. While the reaction time varies depending on the reagent and solvent to be used, it is generally 10 min to 170 hr, preferably 1 hr to 80 hr. The reaction temperature is generally 0° C. to 250° C., preferably 0° C. to 200° C. In addition, microwave irradiation may be used to promote the reaction.

Compound (XXV) can be produced by subjecting compound (VIII) to a cyclization reaction in the presence of a base. Examples of the base include metal alkoxides, alkali metal hydrides, metal amides and the like. The base is used in an amount of about 0.0001 to 20 mol, preferably about 0.01 to 5.0 mol, per 1 mol of compound (VIII). In addition, a metal alkoxide may be prepared by reacting metal hydrides with, for example, methanol, ethanol and the like in the reaction system and used. This reaction is advantageously performed using a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons, sulfoxides, aromatic organic bases and the like or a mixed solvent thereof and the like are preferable. While the reaction time varies depending on the reagent and solvent to be used, it is generally 10 min to 100 hr, preferably 30 min to 24 hr. The reaction temperature is generally −20° C. to 200° C., preferably 0° C. to 150° C.

Compound (XXVI-a) can be produced by subjecting compound (XXV) to a decarboxylation reaction. The decarboxylation reaction can be performed by a method known per se, or a method analogous thereto and, for example, a method using acid or a method analogous thereto and the like can be mentioned. Examples of the acid include inorganic acids, organic acids and the like. The acid is used in an amount of about 0.0001 to 20 mol, preferably about 0.01 to 5.0 mol, per 1 mol of compound (XXV). This reaction is advantageously performed without solvent or in a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons, sulfoxides, organic acids, inorganic acids, water and the like or a mixed solvent thereof and the like are preferable. While the reaction time varies depending on the reagent and solvent to be used, it is generally 10 min to 200 hr, preferably 30 min to 100 hr. The reaction temperature is generally 0° C. to 200° C., preferably 0° C. to 150° C.

Compound (XXVI-c) can be produced by subjecting compound (XXVI-a) to an aldol condensation with an aldehyde or ketone derivative to give compound (XXVI-b), followed by a reduction reaction. The aldol condensation is performed by condensation of compound (XXVI-a) and an aldehyde or ketone derivative represented by the formula $R^{4m}COR^{4n}$ in the presence of a base to give a single configuration isomer of E form or Z form or a mixture of E and Z isomers. The aldehyde or ketone derivative is used in an amount of about 1.0 to 50 mol, preferably about 1.0 to 5.0 mol, per 1 mol of compound (XXVI-a). Examples of the base include inorganic bases, basic salts, organic bases, metal alkoxides, alkali metal hydrides, metal amides and the like. The base is used in an amount of about 1.0 to 5.0 mol, preferably about 1.0 to 2.5 mol, per 1 mol of compound (XXVI-a). In addition, basic alumina and the like (e.g., ICN Alumina B, Akt. 1 manufactured by ICN and the like) can also be used as a base. In this case, alumina and the like are used in an amount of about 1 g to 500 g, preferably about 5 g to 100 g, per 1 g of compound (XXVI-a). This reaction is advantageously performed using a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons, nitrites, sulfoxides, aromatic organic bases and the like or a mixed solvent thereof and the like are preferable. While the reaction time varies depending on the reagent and solvent to be used, it is generally 30 min to 48 hr, preferably 30 min to 5 hr. The reaction temperature is generally −78° C. to 200° C., preferably −10° C. to 150° C. In addition, it can also be produced by dehydrating aldol type intermediate, which is obtained in the presence of a base such as lithium diisopropylamide and the like, in the presence of an acid catalyst such as p-toluenesulfonic acid and the like at room temperature to under heating.

The reduction reaction can be performed by a method similar to the production method of compound (VIII-a) from compound (VII).

As the aldehyde or ketone derivative represented by the formula $R^{4m}COR^{4n}$, a commercially available product may be used or it can be produced according to a method known per se or a method analogous thereto.

Compound (XXVIII-a) wherein m is 1 can be produced by subjecting nitrile to a base treatment to give carbanion, which is reacted with compound (XXVI) to give compound (XXVII), which is then subjected to a dehydrating reaction. Compound (XXVIII-a) can be obtained as a single isomer or a mixture of isomers. Examples of the nitrile include a compound represented by the formula $R^3$—$CH_2CN$. The nitrile is used in an amount of about 1.0 to 10 mol, preferably about 1.0 to 1.5 mol, per 1 mol of compound (XXVI). Examples of the base include metal alkoxides, alkali metal hydrides, metal amides and the like. The base is used in an amount of about 1.0 to 10 mol, preferably about 1.0 to 1.5 mol, per 1 mol of compound (XXVI). This reaction is advantageously performed using a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons and the like or a mixed solvent thereof and the like are preferable. While the reaction time varies depending on the reagent and solvent to be used, it is generally 30 min to 48 hr, preferably 30 min to 5 hr. The reaction temperature is generally −78° C. to 100° C., preferably −78° C. to 50° C. Examples of the catalyst to be used for the dehydrating reaction include acidic catalysts such as inorganic acids, organic acids, boron trifluoride ether complex and the like, basic catalysts such as inorganic bases, basic salts and the like, and the like. In addition, for example, a dehydrating agent such as diphosphorus pentoxide, phosphorus oxychloride, phosphorus pentachloride, triphenylphosphine, phosgene, N,N'-dicyclohexylcarbodiimide, alumina, sodium dioxide, thionyl chloride, methanesulfonyl chloride, trifluoroacetic anhydride and the like may be used. This reaction is advantageously performed without solvent or in a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons, sulfoxides and the like or a mixed solvent thereof and the like are preferable. While the reaction time varies depending on the reagent and solvent to be used, it is generally 30 min to 24 hr, preferably 30 min to 5 hr. The reaction temperature is generally 0° C. to 200° C., preferably 0° C. to 150° C.

As the nitrile derivative represented by the formula $R^3$—$CH_2CN$, a commercially available product may be used, or it can be produced according to a method known per se or a method analogous thereto.

Compound (XXVIII-a) wherein m is 1 can also be produced by reacting phosphonate carbanion, produced by a base treatment of alkylphosphonic acid diester, with compound (XXVI). Compound (XXVIII-a) can be obtained as a single isomer or a mixture of isomers. Examples of the alkylphosphonic acid diester include diethyl cyanomethylphosphonate, diethyl (1-cyanoethyl)phosphonate and the like. The alkylphosphonic acid diester is used in an amount of about 1.0 to 5.0 mol, preferably about 1.0 to 2.0 mol, per 1 mol of compound (XXVI). Examples of the base include metal alkoxides, alkali metal hydrides, metal amides and the like. The base is used in an amount of about 1.0 to 5.0 mol, preferably about 1.0 to 1.5 mol, per 1 mol of compound (XXVI). This reaction is advantageously performed using a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons and the like or a mixed solvent thereof and the like are preferable. While the reaction time varies depending on the reagent and solvent to be used, it is generally 30 min to 50 hr, preferably 1 hr to 10 hr. The reaction temperature is generally −78° C. to 200° C., preferably 0° C. to 150° C.

Compound (XXIX) can be produced by treating compound (XXVI) with trimethylsilyl cyanide in the presence of Lewis acid, and eliminating the resulting trimethylsilyloxy group with an acid. Examples of the Lewis acid include zinc iodide, anhydrous aluminum chloride, anhydrous zinc chloride, anhydrous iron chloride, boron trifluoride ether complex and the like. Lewis acid is used in an amount of about 0.01 to 10 mol, preferably about 0.01 to 1.0 mol, per 1 mol of compound (XXVI). This reaction is advantageously performed without solvent or in a solvent inert to the reaction. While the solvent is not particularly limited as long as the reaction proceeds, for example, solvents such as ethers, aromatic hydrocarbons, saturated hydrocarbons, amides, halogenated hydrocarbons and the like or a mixed solvent thereof and the like are preferable. While the reaction time varies depending on the reagent and solvent to be used, it is generally 10 min to 12 hr, preferably 30 min to 3 hr. The reaction temperature is generally −10° C. to 200° C., preferably −10° C. to 100° C.

Examples of the acid to be used for eliminating a trimethylsilyloxy group include inorganic acids, organic acids, boron trifluoride ether complex and the like. The acid is used in an amount of about 1 to 100 mol, preferably about 1 to 10 mol, per 1 mol of compound (XXVI). This reaction is advantageously performed without solvent or in a solvent inert to the reaction. While the solvent is not particularly limited as long as the reaction proceeds, for example, solvents such as ethers, aromatic hydrocarbons, saturated hydrocarbons, amides, halogenated hydrocarbons, sulfoxides and the like or a mixed solvent thereof and the like are preferable. While the reaction time varies depending on the reagent and solvent to be used, it is generally 30 min to 12 hr, preferably 30 min to 5 hr. The reaction temperature is generally 0° C. to 200° C., preferably 20° C. to 150° C.

Compound (XXVIII-b) wherein m is 2 can be produced from compound (XXVIII-a) according to a known carbon chain extension reaction. For example, a cyano form may be hydrolyzed under alkaline or acidic conditions to give a carboxy form, which is led to an ester form, subjected to a reduction reaction to give an alcohol form, then a reaction via halogenation and cyanation and the like.

Compound (XXX) can be produced as a single isomer or a mixture of isomers by subjecting compound (XXIX) or compound (XXVIII-a) or (XXVIII-b) to a reduction reaction. Examples of the reducing agent include metal hydrides and metal hydride complex compounds. Examples of the hydrogenation catalyst include catalysts such as Raney nickel, Raney cobalt and the like, and the like. The reducing agent, when it is, for example, metal hydride, is used in an amount of about 1.0 to 10 mol, preferably about 1.0 to 3.0 mol, per 1 mol of compound (XXIX) or compound (XXVIII-a) or (XXVIII-b). When the reducing agent is a metal hydride complex compound, it is used in an amount of about 1.0 to 10 mol, preferably about 1.0 to 3.0 mol, per 1 mol of compound (XXIX) or compound (XXVIII-a) or (XXVIII-b). In the case of hydrogenation, a catalyst such as Raney nickel, Raney cobalt and the like is used in an amount of about 10 to 5000 wt %, preferably about 100 to 2000 wt %, relative to compound (XXIX) or compound (XXVIII-a) or (XXVIII-b). This reaction is advantageously performed using a solvent inert to the reaction. While the solvent is not particularly limited as long as the reaction proceeds, for example, solvents such as alcohols, ethers, aromatic hydrocarbons, saturated hydrocarbons, amides, esters, organic acids, water and the like or a mixed solvent thereof and the like are preferable. When a catalyst such as Raney nickel and Raney cobalt is used, amines such as ammonia and the like may be further added to suppress the side reaction. While the reaction time varies depending on the kind and amount of the reducing agent or the activity and amount of the catalyst to be used, it is generally 30 min to 200 hr, preferably 1 hr to 50 hr. The reaction temperature is generally 0° C. to 120° C., preferably 20° C. to 80° C. When a catalyst such as Raney nickel, Raney cobalt and the like is used, the hydrogen pressure is generally 1 to 100 atm.

Compound (I) can be produced by reacting compound (XXX) with carboxylic acid, a salt thereof or a reactive derivative thereof or isocyanate. Examples of the carboxylic acid include a compound represented by the formula $R^1$—COOH. Examples of the reactive derivative of carboxylic acid include acid halides such as acid chloride, acid bromide and the like, acid amides with pyrazole, imidazole, benzotriazole and the like, acid anhydrides such as acetic anhydride, propionic anhydride, butyric anhydride and the like, acid azides, active esters such as diethoxyphosphoric acid ester, diphenoxyphosphoric acid ester, p-nitrophenyl ester, 2,4-dinitrophenyl ester, cyanomethyl ester, pentachlorophenyl ester, ester with N-hydroxysuccinimide, ester with N-hydroxyphthalimide, ester with 1-hydroxybenzotriazole, ester with 6-chloro-1-hydroxybenzotriazole, ester with 1-hydroxy-1H-2-pyridone and the like, active thioesters such as 2-pyridyl thioester, 2-benzothiazolyl thioester and the like, and the like. Instead of using the reactive derivatives, carboxylic acid or a salt thereof may be directly reacted with compound (XXX) in the presence of a suitable condensation agent. Examples of the condensation agent include N,N'-disubstituted carbodiimides such as N,N'-dicyclohexylcarbodiimide, 1-ethyl-3-(3-dimethylaminopropyl)carbodiimide (WSC) hydrochloride and the like, azolides such as N,N'-carbonyldiimidazole and the like, dehydrating agents such as N-ethoxycarbonyl-2-ethoxy-1,2-dihydroquinoline, phosphorus oxychloride, alkoxyacetylene and the like, 2-halogenopyridinium salts such as 2-chloromethylpyridinium iodide, 2-fluoro-1-methylpyridinium iodide and the like, and the like. When these condensation agents are used, the reaction is considered to proceed via a reactive derivative of carboxylic acid. As the isocyanate, for example, a compound represented by the formula $R^1$—NCO can be mentioned. The carboxylic acid, a salt thereof or a reactive derivative thereof, or the isocyanate is used in an amount of generally about 1.0 to 5.0 mol, preferably about 1.0 to 2.0 mol, per 1 mol of compound (XXX). This reaction is advantageously performed using a solvent inert to the reaction. While the solvent is not particularly limited as long as the reaction proceeds, for example, solvents such as ethers, aromatic hydrocarbons, saturated hydrocarbons, amides, halogenated hydrocarbons, nitriles, sulfoxides, aromatic organic bases and the like or a mixed solvent thereof and the like are preferable. When an acidic substance is released by the reaction, the reaction can be performed in the presence of a deacidifying agent to remove the acidic substance from the reaction system. Examples of the deacidifying agent include basic salts, organic bases and the like. While the reaction time varies depending on the reagent and solvent to be used, it is generally 10 min to 24 hr, preferably 30 min to 4 hr. The reaction temperature is generally 0° C. to 100° C., preferably 0° C. to 70° C.

Compound (I) can be produced by reacting compound (XXX) with a carbonating agent. The carbonation reaction can be performed according to, for example, the method described in Shin Jikken Kagaku Koza (New Experimental Chemistry Course), vols. 14 and 15, pages 230-239 (The Chemical Society of Japan Ed.) and the like, or a method analogous thereto.

A carboxylic acid represented by the formula $R^1$—COOH, a salt thereof or a reactive derivative thereof, or an isocyanate represented by the formula $R^1$—NCO may be a commercially available product, or can also be produced by a method known per se, or a method analogous thereto.

A single isomer of compound (I) or a mixture of isomers of compound (I) can be converted to a different single isomer or a mixture of isomers at different ratio by a heat treatment, a treatment with an acid or a treatment with a base. Examples of the acid include inorganic acids, organic acids, boron trifluoride ether complex and the like. Examples of the base include inorganic bases, basic salts, organic bases, metal alkoxides, alkali metal hydrides, metal amides, organic lithiums and the like. The acid or base is used in an amount of about 0.01 to 100 mol, preferably about 0.01 to 5.0 mol, per 1 mol of compound (I). This reaction is advantageously performed without solvent or in a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons, water and the like or a mixed solvent thereof and the like are preferable. While the reaction time varies depending on the reagent and solvent to be used, it is generally 10 min to 100 hr, preferably 30 min to 24 hr. The reaction temperature is generally −10° C. to 200° C., preferably −10° C. to 150° C.

When a compound (I) wherein the double bond moiety is reduced is to be produced, the compound can be produced by subjecting the double bond moiety of compound (I) to a reduction reaction. The reduction reaction is generally carried out using a reducing agent according to a conventional method. Examples of the reducing agent include metal hydride, metal hydride complex compound, borane complex, alkylboranes, diborane, metals, alkali metal (e.g., sodium, lithium and the like)/liquid ammonia (Birch reduction) and the like. The amount of the reducing agent to be used is appropriately determined according to the kind of the reducing agent. For example, metal hydride, metal hydride complex compound, borane complex, alkylboranes or diborane is used in an amount of about 0.25 to 10 mol, preferably about 0.5 to 5 mol, per 1 mol of compound (I), and metal (including alkali metal to be used for Birch reduction) is used in an amount of about 1.0 to 20 mol, preferably about 1.0 to 5.0 mol, per 1 mol of compound (1). This reaction is advantageously performed using a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons, organic acids, water and the like, or a mixed solvent thereof and the like are preferable. While the reaction time varies depending on the reagent and solvent to be used, it is generally 10 min to 100 hr, preferably 30 min to 50 hr. The reaction temperature is generally −20° C. to 100° C., preferably 0° C. to 80° C. In addition, a hydrogenation reaction enables reduction reaction. In this case, for example, a catalyst such as palladium carbon, platinum(IV) oxide, Raney nickel, Raney cobalt etc., or the like is used. The catalyst is used in an amount of about 1.0 to 300 wt %, preferably about 10 to 20 wt % relative to compound (I). Various hydrogen sources can also be used instead of gaseous hydrogen. As the hydrogen source, for example, formic acid, ammonium formate, triethylammonium formate, sodium phosphinate, hydrazine and the like are used. The hydrogen source is used in an amount of about 1.0 to 10 mol, preferably about 1.0 to 5.0 mol, per 1 mol of compound (1). This reaction is advantageously performed using a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons, esters, organic acids and the like or a mixed solvent thereof and the like are preferable. While the reaction time varies depending on the kind and amount of the reducing agent and the activity and amount of the catalyst to be used, it is generally 30 min to 100 hr, preferably 1 hr to 50 hr. The reaction temperature is generally −20° C. to 120° C., preferably 0° C. to 80° C. When hydrogenation catalyst is used, the pressure of hydrogen is generally 1 to 100 atm.

Compound (I) wherein $R^2$ is a hydrocarbon group optionally having substituent(s) can be produced by an alkylation reaction of compound (I) wherein $R^2$ is a hydrogen atom using a corresponding alkylating agent (e.g., alkyl halide, sulfonic acid ester of alcohol and the like) in the presence of a base. Examples of the base include inorganic bases, basic salts, organic bases, metal alkoxides, alkali metal hydrides, metal amides and the like. The base is used in an amount of about 1.0 to 5.0 mol, preferably about 1.0 to 2.0 mol, per 1 mol of compound (I). This reaction is advantageously performed using a solvent inert to the reaction. While the solvent is not particularly limited as long as the reaction proceeds, for example, solvents such as ethers, aromatic hydrocarbons, saturated hydrocarbons, amides, halogenated hydrocarbons, nitriles, sulfoxides and the like or a mixed solvent thereof and the like are preferable. While the reaction time varies depending on the reagent and solvent to be used, it is generally 30 min to 48 hr, preferably 30 min to 6 hr. The reaction temperature is generally −20° C. to 200° C., preferably −10° C. to 150° C.

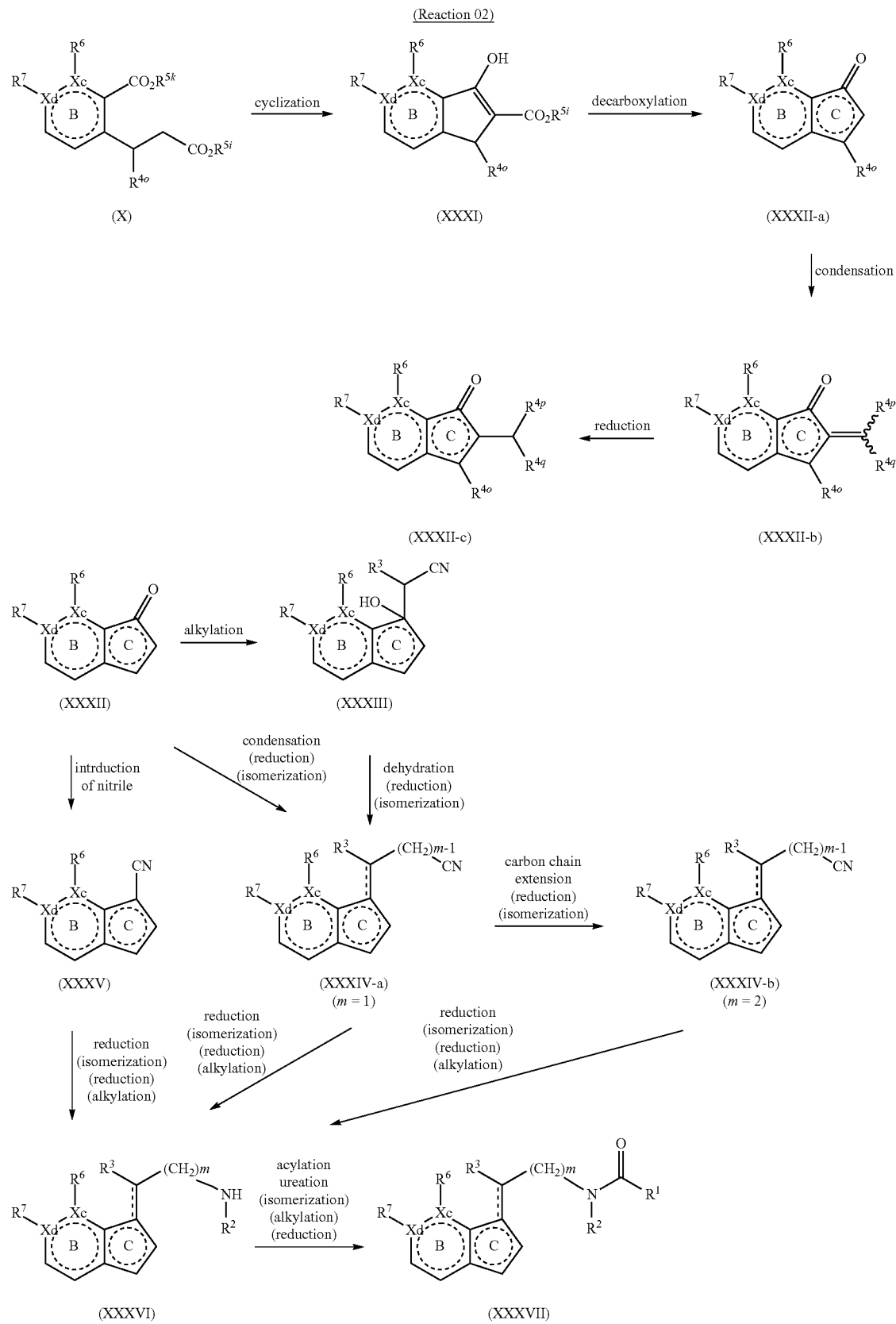

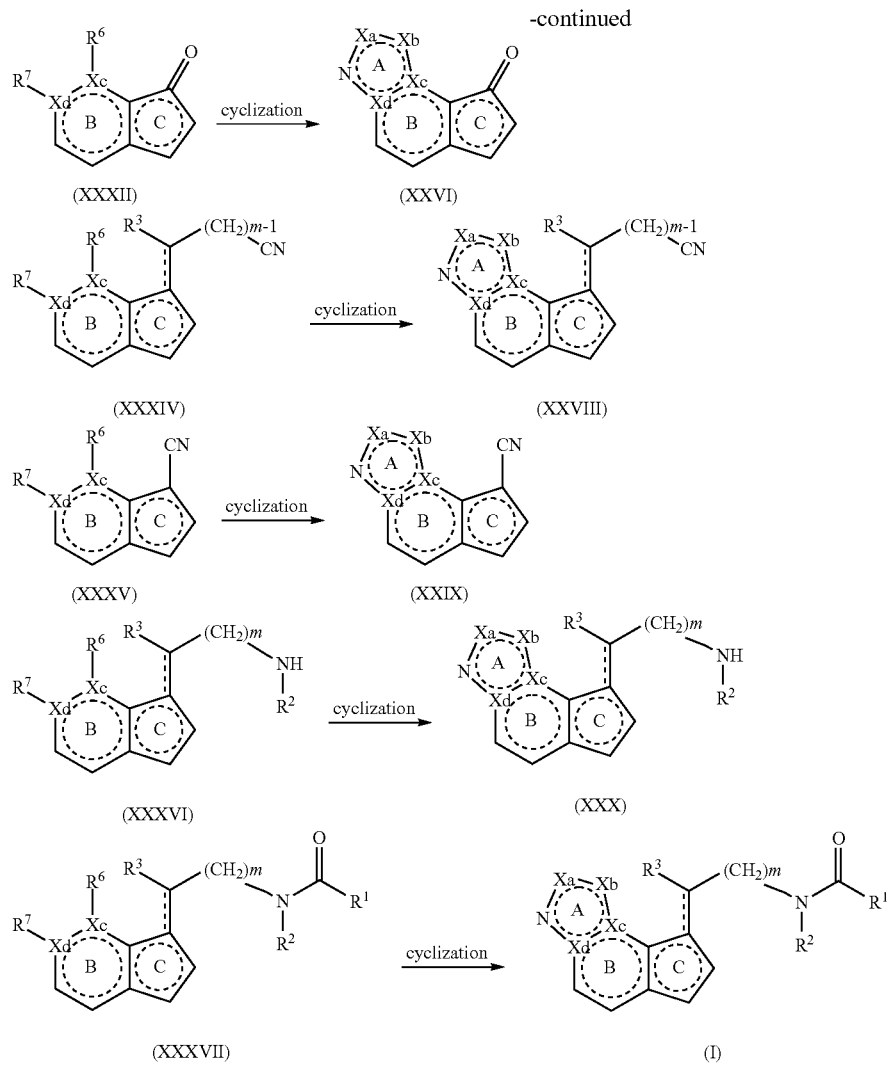

Compound (XXXI) can be produced by subjecting compound (X) to a cyclization reaction. Compound (X) is a formula collectively showing compound (X-a) [Xc:C, Xd:C, $R^6$:—$CH_2$—$R^{4a}$, $R^7$:—$NP^1P^2$], compound (X-b) [Xc:C, Xd:C, $R^6$:—$NP^3P^4$, $R^7$:—NH—CO—$R^{4d}$], compound (X-c) [Xc:C, Xd:N, $R^6$:H, $R^7$:H], compound (X-d) [Xc:C, Xd:N, $R^6$:—CO—$R^{4h}$, $R^7$:H], compound (X-e) [Xc:C, Xd:N, $R^6$:—$C(R^{4h})$=N—OH, $R^7$:H], compound (X-f) [Xc:N, Xd:C, $R^6$:H, $R^7$:—$NP^5P^6$], compound (X-g) [Xc:N, Xd:C, $R^6$:H, $R^7$:—N=$C(R^{4i})N(CH_3)_2$], compound (X-h) [Xc:N, Xd:C, $R^6$:H, $R^7$:—NH—$C(R^{4i})$=N—OH], compound (X-i) [Xc:N, Xd:C, $R^6$:H, $R^7$:Y] and compound (X-j) [Xc:N, Xd:C, $R^6$:H, $R^7$:—NH—$NH_2$], wherein each symbol is as defined above. The cyclization reaction can be performed by a method similar to the method of producing compound (XXV) from compound (VIII).

Compound (XXXII-a) can be produced by subjecting compound (XXXI) to a decarboxylation reaction. The decarboxylation reaction can be performed by a method similar to the method of producing compound (XXVI-a) from compound (XXV).

Compound (XXXII-c) can be produced by performing an aldol condensation of compound (XXXII-a) and an aldehyde or ketone derivative represented by the formula RPCOR to give compound (XXXII-b), and subjecting the compound to a reduction reaction. The condensation reaction and reduction reaction can be performed by a method similar to the method of producing compound (XXVI-c) from compound (XXVI-a).

The aldehyde or ketone derivative represented by the formula $R^{4p}COR^{4q}$ may be a commercially available product, or can also be produced according to a method known per se or a method analogous thereto.

Compound (XXXIV-a) wherein m is 1 can be produced by reacting carbanion, obtained by treating nitrile with a base, with compound (XXXII) to give compound (XXXIII), and subjecting the compound to a dehydrating reaction. Compound (XXXIV-a) is obtained as a single isomer or a mixture of isomers. The alkylation reaction and dehydrating reaction can be performed by a method similar to the method of producing compound (XXVIII-a) from compound (XXVI).

Compound (XXXIV-a) can also be produced by condensing phosphonate carbanion, obtained by a base treatment of alkylphosphonic acid diester, with compound (XXXII). The condensation reaction can be performed by a method similar to the method of producing compound (XXVIII-a) from compound (XXVI).

Compound (XXXV) can be produced by treating compound (XXXII) with trimethylsilyl cyanide in the presence of Lewis acid, and eliminating the resulting trimethylsilyloxy group with an acid. The introduction of nitrile can be performed by a method similar to the method of producing compound (XXIX) from compound (XXVI).

Compound (XXXIV-b) wherein m is 2 can be produced from compound (XXXIV-a) according to a known carbon chain extension reaction. The carbon chain extension reaction can be performed by a method similar to the method of producing compound (XXVIII-b) from compound (XXVIII-a).

Compound (XXXVI) can be produced as a single isomer or a mixture of isomers by subjecting compound (XXXV), compound (XXXIV-a) or compound (XXXIV-b) to a reduction reaction. The reduction reaction can be performed by a method similar to the method of producing compound (XXX) from compound (XXIX), compound (XXVIII-a) or compound (XXVIII-b).

Compound (XXXVII) can be produced by reacting compound (XXXVI) with a carboxylic acid, a salt thereof or a reactive derivative thereof, isocyanate, or a carbonating agent. The acylation reaction, ureation reaction and carbonation reaction can be performed by a method similar to the method of producing compound (I) from compound (XXX).

Compounds (XXVIII-a), (XXVIII-b), (XXX), (XXXIV-a), (XXXIV-b), (XXXVI) and (XXXVII) can be produced as a different single isomer or a mixture of isomers at different ratio by a method similar to the method of isomerizing compound (I).

Of compounds (XXVIII-a), (XXVIII-b), (XXX), (XXXIV-a), (XXXIV-b), (XXXVI) and (XXXVII), a compound wherein the double bond moiety is reduced can be produced by a method similar to the method of reducing the double bond moiety of compound (I).

Of compound (XXXVII), a compound wherein $R^2$ is a hydrocarbon group optionally having substituent(s) can be produced by an alkylation reaction of compound (XXXVII) wherein $R^2$ is a hydrogen atom. The alkylation reaction can be performed by a method similar to the method of producing compound (I) wherein $R^2$ is a hydrocarbon group optionally having substituent(s) from compound (I) wherein $R^2$ is a hydrogen atom.

Compound (XXVI) can be produced by subjecting compound (XXXII) to a series of reaction steps including a cyclization reaction. Examples of the series of reaction steps including a cyclization reaction include a method of producing compound (IV) or (V) from compound (III), a method of producing compound (VIII-b) from compound (X-b), a method of producing compound (VIII-c) or (VIII-d) from compound (X-c), a method of producing compound (VIII-e) from compound (X-c), a method of producing compound (VIII-f) from compound (X-e), a method of producing compound (VIII-g) from compound (X-h), a method of producing compound (VIII-h) from compound (X-f), a method of producing compound (VIII-i) from compound (X-j) and the like, and the reaction can be performed by a method similar to the methods of producing them.

Compound (XXVIII) can be produced by subjecting compound (XXXIV) to a series of reaction steps including a cyclization reaction. These reactions can be performed by a method similar to the method of producing compound (XXVI) from compound (XXXII).

Compound (XXIX) can be produced by subjecting compound (XXXV) to a series of reaction steps including a cyclization reaction. These reactions can be performed by a method similar to the method of producing compound (XXVI) from compound (XXXII).

Compound (XXX) can be produced by subjecting compound (XXXVI) to a series of reaction steps including a cyclization reaction. These reactions can be performed by a method similar to the method of producing compound (XXVI) from compound (XXXII).

Compound (I) can be produced by subjecting compound (XXXVII) to a series of reaction steps including a cyclization reaction. These reactions can be performed by a method similar to the method of producing compound (XXVI) from compound (XXXII).

(Reaction 03)

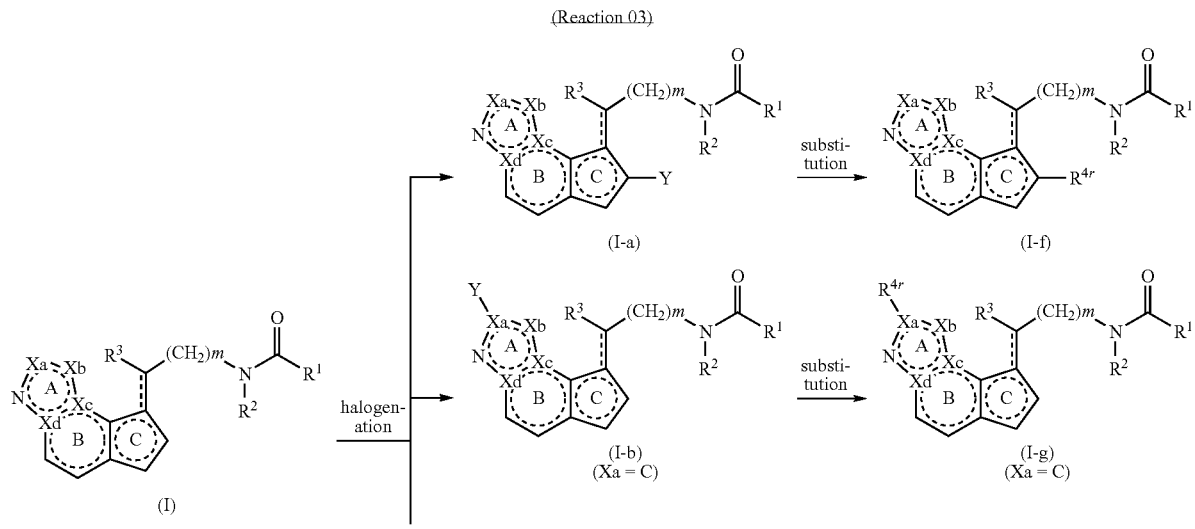

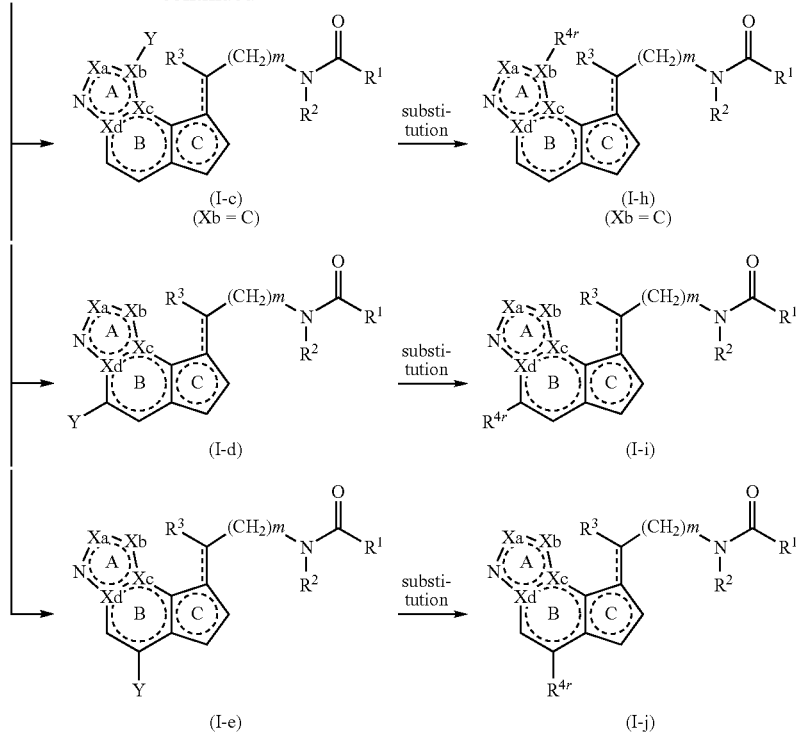

Compound (I-f) can be produced by reacting compound (I) with a halogenating agent to give compound (I-a), then subjecting the compound to a condensation reaction using organic boronic acid or organic boronic acid ester and a metal catalyst. Examples of the halogenating agent include phosphorus halide, succinimides, halogen, thionyl chloride, and mixtures thereof and the like. The halogenating agent is used in an amount of about 1.0 to 100 mol, preferably about 1.0 to 10 mol, per 1 mol of compound (I). To promote the reaction, the reaction can be performed in the presence of a base. Examples of the base include inorganic bases, basic salts and the like. This reaction is advantageously performed without solvent or in a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons, nitrites, sulfoxides, acid anhydrides, organic acids, inorganic acids, water and the like or a mixed solvent thereof and the like are preferable. While the reaction time varies depending on the reagent and solvent to be used, it is generally 10 min to 50 hr, preferably 30 min to 12 hr. The reaction temperature is generally 0° C. to 200° C., preferably 10° C. to 100° C. The condensation reaction is performed by reacting compound (I-a) with organic boronic acid or organic boronic acid ester in the presence of a metal catalyst. Examples of the organic boronic acid and organic boronic acid ester include a compound represented by the formula $R^{4r}$-M wherein M is the boron atom part of the organic boronic acid or organic boronic acid ester. Examples of the M include dihydroxyboranyl, 4,4,5,5-tetramethyl-1,3,2-dioxaborolan-2-yl and the like are preferable. As the metal catalyst, palladium compound is preferable. The reaction is generally performed in the presence of a base. Examples of the base include inorganic bases, basic salts and the like. The organic boronic acid or organic boronic acid ester is used in an amount of about 0.1 to 10 mol, preferably about 0.8 to 2.0 mol, per 1 mol of compound (I-a). The metal catalyst is used in an amount of about 0.000001 to 5.0 mol, preferably about 0.0001 to 1.0 mol, per 1 mol of compound (I-a). The base is used in an amount of about 1.0 to 20 mol, preferably about 1.0 to 5.0 mol, per 1 mol of compound (I-a). When a metal catalyst unstable to oxygen is used for these reactions, the reaction is preferably performed, for example, in an inert gas stream such as argon gas, nitrogen gas and the like. This reaction is advantageously performed using a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons, nitrites, esters, water and the like or a mixed solvent thereof and the like are preferable. While the reaction time varies depending on the reagent and solvent to be used, it is generally 1 min to 200 hr, preferably 5 min to 100 hr. The reaction temperature is −10° C. to 250° C., preferably 0° C. to 150° C.

An organic boronic acid or an organic boronic acid ester represented by the formula $R^{4r}$-M may be a commercially available one, or can also be produced by a method known per se, or a method analogous thereto.

Compound (I-f) can also be produced by subjecting compound (I-a) to a desired substituent exchange reaction known per se. The reaction can be carried out, for example, by the method described in Shin Jikken Kagaku Koza (New Experimental Chemistry Course), vols. 14 and 15 (edited by the Chemical Society of Japan) and the like, or a method analogous thereto.

Compounds (I-g), (I-h), (I-i) and (I-j) can be produced by a method similar to the method for producing compound (I-f) from compound (I).

A compound represented by the formula

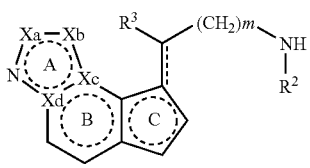

wherein each symbol is as defined above (hereinafter sometimes to be abbreviated as compound (A)), or a salt thereof, which is obtained in the reaction step to give the aforementioned compound (I), is a novel compound, and can be used as a starting material of the compound of the present invention.

In compound (A), $R^2$ is preferably a hydrogen atom.
As $R^3$, a hydrogen atom is preferable.
As Xa, $N(C_{1-6}$ alkyl), CH or $C(C_{1-6}$ alkyl) is preferable.
As Xb, CH, $C(C_{1-6}$ alkyl) or $C(C_{1-6}$ alkoxy-carbonyl) is preferable.
As Xc, C is preferable.
As Xd, C or N is preferable.
As m, 1 is preferable.

As tricycle consisting of ring A, ring B and ring C, a tricycle represented by the following formula is preferable.

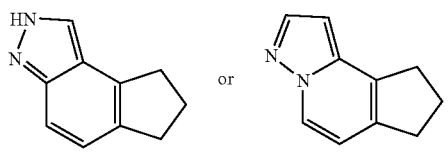

It may have, on ring A, one or two substituents selected from $C_{1-6}$ alkyl and $C_{1-6}$ alkoxy-carbonyl. Of these, preferable compounds are
2-(2-methyl-6,7-dihydrocyclopenta[e]indazol-8(2H)-ylidene)ethanamine (Reference Example 27),
2-(1,2-dimethyl-6,7-dihydrocyclopenta[e]indazol-8(2H)-ylidene)ethanamine (Reference Example 28),
ethyl 9-(2-aminoethyl)-8,9-dihydro-7H-cyclopenta[c]pyrazolo[1,5-a]pyridine-1-carboxylate (Reference Example 40),
2-(8,9-dihydro-7H-cyclopenta[c]pyrazolo[1,5-a]pyridin-9-yl)ethanamine hydrochloride (Reference Example 41),
ethyl 9-(2-aminoethyl)-2-methyl-8,9-dihydro-7H-cyclopenta[c]pyrazolo[1,5-a]pyridine-1-carboxylate (Reference Example 42),
2-(2-methyl-8,9-dihydro-7H-cyclopenta[c]pyrazolo[1,5-a]pyridin-9-yl)ethanamine hydrochloride (Reference Example 43),
ethyl 9-(2-aminoethyl)-2-ethyl-8,9-dihydro-7H-cyclopenta[c]pyrazolo[1,5-a]pyridine-1-carboxylate (Reference Example 44), optically active forms thereof, salts thereof and the like.

In the aforementioned respective reactions, when the starting compound has amino, carboxy, hydroxy or a heterocyclic group, these groups may be protected by a protecting group generally used in the peptide chemistry and the like. In this case, the object compound can be obtained by removing the protecting group as necessary after the reaction. Introduction and removal of these protecting groups can be performed by a method known per se, for example, the method described in "Protective Groups in Organic Synthesis, $3^{rd}$ Ed." (Theodora W. Greene, Peter G. M. Wuts, Wiley-Interscience, 1999) and the like.

The configuration isomers of the aforementioned compounds (II)-(XXXVII) can be isolated and purified by, for example, a conventional separation means such as extraction, recrystallization, distillation, chromatography and the like, when isomerization occurs, whereby a pure compound can be produced. In addition, isomerization of double bond may be promoted by heating, acid catalyst, transition metal complex, metal catalyst, radical species catalyst, photoirradiation or strong basic catalyst and the like according to the method described in Shin Jikken Kagaku Koza (New Experimental Chemistry Course), vol. 14, pp. 251-253 (edited by the Chemical Society of Japan), Jikken Kagaku Koza (Courses in Experimental Chemistry), 4th Ed., vol. 19, pp. 273-274 (edited by the Chemical Society of Japan) and the like or a method analogous thereto, whereby a corresponding pure isomer can be obtained. While compound (I) has a stereoisomer depending on the kind of the substituent, not only the isomer itself but also a mixture thereof are encompassed in the present invention. In the above-mentioned reaction steps, where desired, compound (I) can be produced by a known hydrolysis, deprotection, acylation reaction, alkylation reaction, hydrogenation reaction, oxidation reaction, reduction reaction, carbon chain extension reaction or substituent exchange reaction, conducted individually or by a combination of two or more thereof. These reactions can be carried out, for example, according to the method described in Shin Jikken Kagaku Koza (New Experimental Chemistry Course), vols. 14 and 15 (edited by the Chemical Society of Japan) and the like.

Compound (I) can be isolated and purified by a known means, for example, phase transfer, concentration, solvent extraction, fractional distillation, liquid conversion, crystallization, recrystallization, chromatography and the like.

When compound (I) is obtained as a free compound, it can be converted into a desired salt by a method known per se or a modification thereof; conversely, when compound (I) is obtained as a salt, it can be converted into a free form or another desired salt by a method known per se or a modification thereof.

Compound (I) may be used as a prodrug. A prodrug of compound (I) means a compound which is converted to compound (I) with a reaction due to an enzyme, gastric acid, etc. under the physiological condition in the living body, that is, a compound which is converted to compound (I) by oxidation, reduction, hydrolysis, etc. according to an enzyme; a compound which is converted to compound (I) by hydrolysis etc. due to gastric acid, etc.

A prodrug of compound (I) may be a compound obtained by subjecting amino in compound (I) to an acylation, alkylation or phosphorylation (e.g., a compound obtained by subjecting amino in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation, etc.); a compound obtained by subjecting hydroxy in compound (I) to an acylation, alkylation, phosphorylation or boration (e.g., a compound obtained by subjecting hydroxy in compound (I) to an acetylation, palmitoylation, propanoylation, pivaloylation, succinylation, fumarylation, alanylation, dimethylaminomethylcarbonylation, etc.); a compound obtained by subjecting carboxy in compound (I) to an esterification or amidation (e.g., a compound obtained by subjecting carboxy in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification and methylamidation, etc.) and the like. Any of these compounds can be produced from compound (I) by a method known per se.

A prodrug for compound (I) may also be one which is converted into compound (I) under a physiological condition, such as those described in IYAKUHIN no KAIHATSU (Development of Pharmaceuticals), Vol. 7 (Design of Molecules), p. 163-198 (HIROKAWA SHOTEN).

When compound (I) has isomers such as optical isomer, stereoisomer, positional isomer, rotational isomer and the like, any isomers and mixtures are encompassed in compound (I). For example, when compound (I) has an optical isomer, an optical isomer separated from a racemate is also encompassed in compound (I). These isomers can be obtained as independent products by a synthesis means or a separation means (e.g., concentration, solvent extraction, column chromatography, recrystallization and the like), optical resolution methods (e.g., fractional recrystallization, chiral column method, diastereomer method and the like) and the like known per se.

Compound (I) may be a crystal, and both a single crystal and crystal mixtures are encompassed in compound (I) of the present invention. Crystals can be produced by crystallization according to crystallization methods known per se.

Compound (I) may be a solvate (e.g., hydrate etc.) or a non-solvate (e.g., non-hydrate etc.), both of which are encompassed in compound (I) of the present invention.

A compound labeled with an isotope (e.g., $^2$H, $^3$H, $^{14}$C, $^{35}$S, $^{125}$I and the like) is also encompassed in compound (I) of the present invention.

Compound (I) of the present invention show high affinity for melatonin receptors ($MT_1$ receptor, $MT_2$ receptor). Since compound (I) acts as a melatonin agonist, has physiological activities such as melatonin receptor affinity and the like, shows low toxicity (e.g., acute toxicity, chronic toxicity, genetic toxicity, reproductive toxicity, cardiotoxicity, drug interaction, carcinogenicity and the like), and is superior in the stability and in vivo kinetics (absorption, distribution, metabolism, excretion and the like), it is useful as a pharmaceutical product. Compound (I) acts as a melatonin agonist in mammals (e.g., mouse, rat, hamster, rabbit, cat, dog, bovine, sheep, monkey, human and the like), is useful as a composition with a binding affinity for melatonin receptor, particularly, a melatonin receptor agonist, and can be used as a prophylactic or therapeutic drug for a disease possibly influenced by melatonin. As the "disease possibly influenced by melatonin", for example, sleep disorders [e.g., intrinsic sleep disorders (e.g., psychophysiological insomnia and the like), extrinsic sleep disorders, circadian rhythm disorders (e.g., time-zone change syndrome (jet lag), shift work sleep disorder, irregular sleep-wake pattern, delayed sleep phase syndrome, advanced sleep phase syndrome, non-24 hour sleep-wake syndrome and the like), parasomnias, sleep disorder associated with internal or psychic disorders (e.g., chronic obstructive pulmonary disease, Alzheimer's disease, Parkinson's disease, cerebrovascular dementia, schizophrenia, depression, anxiety neurosis), insomnia and the like], neurodegenerative diseases (e.g., senile dementia, Alzheimer's disease, Parkinson's disease, Creutzfeldt-Jakob disease, amyotrophic lateral sclerosis (ALS), Huntington's disease, spinocerebellar degeneration, multiple sclerosis (MS) and the like), psychoneurotic diseases (e.g., depression, anxiety, bipolar disorder, posttraumatic stress disorder (PTSD), seasonal melancholia, schizophrenia and the like), memory disorders (e.g., senile dementia, mild cognitive impairment (MCI), amnesia and the like), ischemic central nerve disorders (e.g., cerebral infarction, cerebral hemorrhage, brain edema and the like), central nervous system injury (e.g., head trauma, spinal cord injury, whiplash injury and the like), vascular dementia (e.g., multi-infarct dementia, Binswanger's disease and the like), cancer (e.g., brain tumor, pituitary adenoma, glioma, acoustic schwannoma, retinoblastoma, thyroid cancer, pharyngeal cancer, laryngeal cancer, cancer of the tongue, thymoma, mesothelial tumor, breast cancer, lung cancer, non-small cell lung cancer, small cell lung cancer, gastric cancer, esophageal cancer, duodenal cancer, colorectal cancer, colon cancer, rectal cancer, liver cancer, hepatocellular carcinoma, pancreatic cancer, pancreatic endocrine tumor, biliary tract cancer, gallurinary bladder cancer, penile cancer, kidney cancer, renal pelvic cancer, ureteral cancer, renal cell cancer, testis tumor, prostate cancer, urinary bladder cancer, vulvar cancer, uterus cancer, cancer of uterine cervix, cancer of uterine body, uterine sarcoma, chorionic disease, vaginal cancer, ovary cancer, ovarian germ cell tumor, skin cancer, malignant melanoma, mycosis fungoides, basal cell tumor, soft tissue sarcoma, malignant lymphoma, Hodgkin's disease, osteomyelodysplasia syndrome, multiple myeloma, leukemia, acute myelocytic leukemia, chronic myelocytic leukemia, acute lymphatic leukemia, chronic lymphatic leukemia, adult T cell leukemia, chronic myeloproliferative disease, pancreatic endocrine tumor, fibrous histiocytoma, leiomyosarcoma, rhabdomyosarcoma, unknown primary cancer and the like), hyperinsulinemia, metabolic syndrome, obesity (obesity), diabetes, diabetic complications (e.g., diabetic retinopathy, diabetic neuropathy, diabetic nephropathy and the like), hypertriglyceridemia (hyperlipidemia), hypertension, circulatory disease [e.g., ischemic cardiac diseases (e.g., myocardial infarction, angina pectoris and the like), cerebral apoplexy, arteriosclerosis, arterial restenosis after PTCA and the like], lower urinary tract disease or disorder (e.g., dysuria, incontinence and the like), osteoporosis, reproductive and neuroendocrine diseases, convulsion, glaucoma, headache, irritable bowel syndrome and the like can be mentioned. In addition, it is effective for immunoregulation, cognitive enhancement, tranquilization, stress or regulation of ovulation (e.g., contraception and the like).

Compound (I) [sometimes to be abbreviated as "the compound of the present invention"] can be safely administered orally or parenterally (e.g., subcutaneous, topical, rectal, intravenous administrations etc.) by itself, or in the form of a pharmaceutical composition containing a pharmacologically acceptable carrier according to a conventional method (e.g., the method described in the Japanese Pharmacopoeia etc.), such as tablet (including sugar-coated tablet, film-coated tablet and the like), powder, granule, capsule, liquid, emulsion, suspension, injection, suppository, sustained-release preparation (e.g., sublingual tablet, microcapsule etc.), plaster, orally disintegrating tablet, orally disintegrating film and the like.

As pharmacologically acceptable carriers, various organic or inorganic carrier substances conventionally used as preparation materials can be mentioned. For example, suitable amounts of additives such as excipient, lubricant, binder and disintegrant for solid preparations, or solvent, solubilizing agent, suspending agent, isotonicity agent, buffer and soothing agent for liquid preparations, and where necessary, conventional preservative, antioxidizing agent, colorant, sweetening agent, adsorbent, wetting agent and the like can be used appropriately.

As the excipient, for example, lactose, sucrose, D-mannitol, starch, cornstarch, crystalline cellulose, light anhydrous silicic acid and the like can be mentioned. As the lubricant, for example, magnesium stearate, calcium stearate, talc, colloidal silica and the like can be mentioned. As the binder, for example, crystalline cellulose, sucrose, D-mannitol, dextrin, hydroxypropylcellulose, hydroxypropylmethylcellulose, polyvinylpyrrolidone, starch, sucrose, gelatin, methylcellulose, sodium carboxymethylcellulose and the like can be mentioned. As the disintegrant, for example, starch, carboxymethylcellulose, calcium carboxymethylcellulose, croscarmellose sodium, sodium carboxymethyl starch, L-hydroxypropylcellulose and the like can be mentioned. As the solvent, for example, water for injection, alcohol, propylene glycol, macrogol, sesame oil, corn oil, olive oil and the like can be mentioned. As the solubilizing agents, for example, polyethylene glycol, propylene glycol, D-mannitol, benzyl benzoate, ethanol, trisaminomethane, cholesterol, triethanolamine, sodium carbonate, sodium citrate and the like can be mentioned. As the suspending agent, for example, surfactants such as stearyltriethanolamine, sodium lauryl sulfate, lauryl aminopropionate, lecithin, benzalkonium chloride, benzethonium chloride, glyceryl monostearate, and the like; for example, hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose etc., and the like can be mentioned. As the isotonicity agent, for example, glucose, D-sorbitol, sodium chloride, glycerol, D-mannitol and the like can be mentioned. As the buffer, for example, buffer such as phosphate, acetate, carbonate, citrate etc., and the like can be mentioned. As the soothing agent, for example, benzyl alcohol and the like can be mentioned. As the preservative, for example, p-hydroxybenzoates, chlorobutanol, benzyl alcohol, phenethyl alcohol, dehydroacetic acid, sorbic acid and the like can be mentioned. As the antioxidizing agent, for example, sulfite, ascorbic acid, α-tocopherol and the like can be mentioned.

While the dose of the compound of the present invention varies depending on the subject of administration, administration route and symptom and is not particularly limited, for example, for oral administration to adult patients for the treatment of insomnia, it is about 0.001 to about 3 mg/kg body weight, preferably about 0.005 to about 2 mg/kg body weight, more preferably about 0.01 to about 1 mg/kg body weight, as the compound of the present invention, which is the active ingredient. The dose is desirably administered about 1 to 3 times a day according to the symptom.

The content of the compound of the present invention in the above-mentioned "agent (pharmaceutical composition)" is about 0.01 to 100 wt % of the whole composition.

When the compound of the present invention is applied to each of the above-mentioned diseases, it can be used in appropriate combination with a pharmaceutical agent or a treatment method generally employed for the disease.

In the following, a combined use of the compound of the present invention with a concomitant drug is referred to as "the combination agent of the present invention".

As such concomitant drug, for example, sleep inducing agents (e.g., GABA system sleep inducing agent such as brotizolam, estazolam, flurazepam, nitrazepam, triazolam, flunitrazepam, lormetazepam, rilmazafone, quazepam, zopiclone, eszopiclone, zolpidem, zaleplon, indiplon, gabaxadol etc.; non-GABA system sleep inducing agent such as eplivaserin, pruvanserin, diphenhydramine, trazodone, doxepin etc., and the like), antidepressants (e.g., fluoxetine, sertraline, paroxetine, venlafaxine, nefazodone, reboxetine, mirtazapine, imipramine hydrochloride, duloxetine, escitalopram, mifepristone, doxepin, etc.), antianxiety agents (e.g., alprazolam, bromazepam, chlordiazepoxide, diazepam, etizolam, flutoprazepam, lorazepam, etc.), therapeutic agents for Alzheimer's disease (e.g., cholinesterase inhibitors such as donepezil, rivastigmine, galanthamine, zanapezil etc.; cerebral function activators such as idebenone, memantine, vinpocetine etc.; agents for suppressing progression such as Alzhemed etc., and the like), antiparkinson agents (e.g., L-DOPA, deprenyl, carbidopa+levodopa, pergolide, ropinirole, cabergoline, pramipexole, entacaprone, lazabemide etc.), therapeutic agents for amyotrophic lateral sclerosis (e.g., riluzole, mecasermin, gabapentin, etc.), neurotrophic factors, therapeutic agents for schizophrenia (e.g., olanzapine, risperidone, quetiapine, iloperidone, etc.), hypolipidemic agents (e.g., simvastatin, fluvastatin, pravastatin, atorvastatin, etc.), antihypertensive agents (e.g., captopril, delapril, enalapril, nifedipine, nicardipine, amlodipine, alprenolol, propranolol, metoprolol, losartan, valsartan, candesartan, etc.), therapeutic agents for diabetes (e.g., pioglitazone, rosiglitazone, metformin, glibenclamide, nateglinide, voglibose, etc.), antiplatelet agents (e.g., ticlopidine, heparin, urokinase, alteplase, tisokinase, nasaruplase, cilostazol, etc.), antioxidizing agents (e.g., linolenic acid, ascorbic acid, icosapentaenoic acid, docosahexaenoic acid, tocopherol, etc.), vitamins (e.g., tocopherol, ascorbic acid, etc.), sex hormones (e.g., estrogen, estrone, estradiol, etc.), antiinflammatory agents (e.g., prednisolone, betamethasone, dexamethasone, etc.), nonsteroidal antiinflammatory agents (e.g., indomethacin, ibuprofen, acetylsalicylic acid, diclofenac, naproxen, piroxicam, etc.), COX-2 inhibitors (e.g., celecoxib, rofecoxib, etc.), cerebral circulation metabolism improving agents (e.g., nicergoline, ibudilast, ifenprodil, etc.), anticonvulsants (e.g., carbamazepine, valproic acid, clonazepam, vigabatrin, lamotrigine, gabapentin, etc.) and pharmacologically acceptable salts thereof and the like can be mentioned.

By combining the compound of the present invention and a concomitant drug, a superior effect such as (1) the dose can be reduced as compared to single administration of the compound of the present invention or a concomitant drug, (2) the concomitant drug can be selected according to the condition of patients (mild case, severe case and the like), (3) the period of treatment can be set longer by selecting a concomitant drug having different action and mechanism from the compound of the present invention, (4) a sustained treatment effect can be designed by selecting a concomitant drug having different action and mechanism from the compound of the present invention, (5) a synergistic effect can be afforded by a combined use of the compound of the present invention and a concomitant drug, and the like, can be achieved.

A combination agent of the present invention has low toxicity, and for example, the compound of the present invention and/or the above-mentioned concomitant drug can be mixed, according to a method known per se, with a pharmacologically acceptable carrier to give pharmaceutical compositions, such as tablets (including sugar-coated tablet, film-coated tablet), powders, granules, capsules, solutions, emulsions, suspensions, injections, suppositories, sustained release preparations (e.g., sublingual tablet, microcapsule etc.), plasters, orally disintegrating tablets, orally disintegrating films and the like, which can be safely administered orally or parenterally (e.g., subcutaneous, topical, rectal, intravenous administrations etc.).

As pharmacologically acceptable carriers usable for the production of the combination agent of the present invention, various organic or inorganic carrier substances conventionally used as preparation materials can be mentioned. For example, suitable amounts of additives such as excipient, lubricant, binder and disintegrant for solid preparations, or solvent, solubilizing agent, suspending agent, isotonicity agent, buffer and soothing agent for liquid preparations, and where necessary, conventional preservative, antioxidizing agent, colorant, sweetening agent, adsorbent, wetting agent and the like can be used appropriately.

When using the combination agent of the present invention, the administration time of the compound of the present invention and the concomitant drug is not restricted, and the compound of the present invention or a pharmaceutical composition thereof and the concomitant drug or a pharmaceutical composition thereof can be administered to an administration subject simultaneously, or may be administered at different times. The dosage of the concomitant drug may be determined according to the dose clinically used, and can be appropriately selected depending on an administration subject, administration route, disease, combination and the like.

The administration mode of the compound of the present invention and the concomitant drug is not particularly restricted, and it is sufficient that the compound of the present invention and the concomitant drug are combined in administration. Examples of such administration mode include the following:
(1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The compounding ratio of the compound of the present invention to the concomitant drug in the combination agent of the present invention can be appropriately selected depending on an administration subject, administration route, diseases and the like.

For example, the content of the compound of the present invention in the combination agent of the present invention varies depending on the form of a preparation, and usually from about 0.01 to 100 wt %, preferably from about 0.1 to 50 wt %, further preferably from about 0.5 to 20 wt %, based on the whole preparation.

While the content of the concomitant drug in the combination agent of the present invention varies depending on the form of a preparation, it is usually from about 0.01 to 100 wt %, preferably from about 0.1 to 50 wt %, further preferably from about 0.5 to 20 wt %, based on the whole preparation.

While the content of the additives such as carrier and the like in the combination agent of the present invention varies depending on the form of a preparation, it is generally about 1 to 99.99 wt %, preferably about 10 to 90 wt %, based on the whole preparation.

Similar contents can be employed for individual preparations of the compound of the present invention and the concomitant drug.

The SEQ ID NOs in the sequence listing in the present specification shows the following sequences.

SEQ ID NO: 1 shows the base sequence of cDNA fragment encoding the full-length human melatonin 1 receptor (human $MT_1$ receptor). (see Gen Bank ACCESSION No. NM_005958)

SEQ ID NO: 2 shows the base sequence of cDNA fragment encoding the full-length human melatonin 2 receptor (human $MT_2$ receptors. (see Gen Bank ACCESSION No. NM_005959)

EXAMPLES

The present invention is explained in detail in the following by referring to Reference Examples, Examples, Formulation Examples and Experimental Examples. However, the examples are mere exemplifications and do not limit the present invention. The present invention may be modified without departing from the scope of the invention. In the following Reference Examples and Examples, the "room temperature" means generally about 10° C. to about 35° C., % means mol/mol % for the yield, % by volume for the solvent used for chromatography, and wt % for others. M means mol/L.

Other abbreviations used in the text mean the following.
s: singlet
d: doublet
t: triplet
q: quartet
m: multiplet
br: broad
J: coupling constant
Hz: Hertz
$CDCl_3$: deuteriochloroform
$DMSO-d_6$: deuteriodimethyl sulfoxide
$METHANOL-d_4$: deuteriomethanol
$^1H$-NMR: proton nuclear magnetic resonance
ee: enantiomer excess The elution for the column chromatography in the Examples was performed under observation by TLC (Thin Layer Chromatography). In the TLC observation, 60F254 manufactured by Merck or NH (DM1020) manufactured by Fuji Silysia Chemical Ltd. was used as a TLC plate.

Unless otherwise specified, the silica gel packed in the column was silica gel 60 (70-230 mesh) (manufactured by Merck) or PURIF-pack (SI 60 μm) (manufactured by Moritex Corporation). When described as silica gel chromatography (NH), CHROMATOREX-NH DM1020 (100-200 mesh) (manufactured by Fuji Silysia Chemical Ltd.) or PURIF-pack (NH 60 μm) (manufactured by Moritex Corporation) was used. Unless otherwise specified, moreover, the elution solvent for silica gel column chromatography is in volume ratio.

As Raney cobalt, Raney cobalt catalyst ODHT-60 (manufactured by Kawaken Fine Chemicals Co., Ltd.) was used after washing with water and ethanol.

Unless otherwise specified, as the palladium-carbon powder, a 10% palladium-carbon powder (50% water-containing product NX type, manufactured by N.E. Chemcat Corporation) was used.

In Reference Examples and Examples, $^1H$-NMR spectrum was measured using tetramethylsilane as the internal standard and the chemical shift is expressed in δ value and the coupling constant is expressed in Hz.

In the following Reference Examples and Examples, melting point, mass spectrum (MS) and nuclear magnetic resonance spectrum (NMR) were measured under the following conditions.

Melting point apparatus: Yanagimoto micromelting point apparatus, or Buchi B-545 melting point apparatus
MS measurement instrument: Waters ZMD, or Waters ZQ, ionization method: Electron Spray Ionization (ESI)
NMR measurement instrument: Varian, Inc., Varian Mercury 300 (300 MHz), Bruker BioSpin AVANCE 300 (300 MHz)

Reference Example 1 methyl 3-amino-6-bromo-2-methylbenzoate

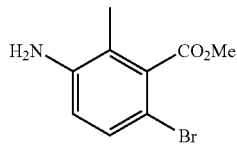

To a mixed solution of methyl 3-amino-2-methylbenzoate (5.00 mL, 34.7 mmol) in acetic acid (100 mL) and methanol (200 mL) was added bromine (5.55 g, 34.7 mmol) under ice-cooling and the mixture was stirred for 5 min. The reaction solution was diluted with saturated aqueous sodium thiosulfate solution, and the organic solvent was evaporated under reduced pressure. The residual aqueous solution was diluted with saturated aqueous sodium hydrogen carbonate solution, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane=5/95→20/80) to give the title compound (4.66 g, yield 55%).
$^1$H-NMR (CDCl$_3$) δ: 2.08 (3H, s), 3.70 (2H, brs), 3.94 (3H, s), 6.58 (1H, d, J=8.5 Hz), 7.18 (1H, d, J=8.5 Hz).

Reference Example 2 methyl 5-bromo-1H-indazole-4-carboxylate

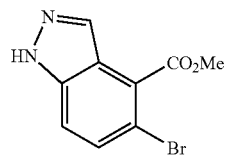

To a solution of methyl 3-amino-6-bromo-2-methylbenzoate (5.44 g, 22.3 mmol) in acetic acid (110 mL) was added a solution of sodium nitrite (1.69 g, 24.5 mmol) in water (11 mL) at room temperature and, after stirring for 20 hr, the organic solvent was evaporated under reduced pressure. The residual aqueous solution was diluted with saturated aqueous sodium hydrogen carbonate solution, and the mixture was extracted with ethyl acetate. The extract was washed with saturated brine, and dried over anhydrous sodium sulfate. The solvent was evaporated under reduced pressure, and the residue was purified by silica gel column chromatography (NH, ethyl acetate/hexane=10/90→30/70) to give the title compound (4.86 g, yield 86%).
$^1$H-NMR (CDCl$_3$) δ: 4.06 (3H, s), 7.48 (1H, dd, J=8.8, 1.1 Hz), 7.63 (1H, d, J=8.8 Hz), 8.26 (1H, d, J=1.1 Hz), 10.59 (1H, brs),
melting point: 164-165° C. (recrystallized from ethyl acetate),
elemental analysis: for C$_9$H$_7$N$_2$O$_2$Br.0.1H$_2$O
Calculated (%): C, 42.08; H, 2.83; N, 10.91.
Found (%): C, 41.97; H, 2.93; N, 10.97.

Reference Example 3 methyl 5-bromo-2-methyl-2H-indazole-4-carboxylate

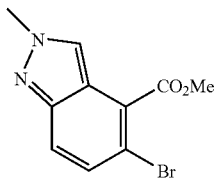

To a solution of methyl 5-bromo-1H-indazole-4-carboxylate (4.50 g, 17.6 mmol) in ethyl acetate (176 mL) was added trimethyloxonium tetrafluoroborate (3.38 g, 22.9 mmol) at room temperature, and the mixture was stirred for 2.5 hr. The reaction solution was diluted with saturated aqueous sodium hydrogen carbonate solution, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane=5/95→30/70) to give the title compound (3.42 g, yield 73%).
$^1$H-NMR (CDCl$_3$) δ: 4.01 (3H, s), 4.22 (3H, s), 7.49 (1H, d, J=9.1 Hz), 7.66 (1H, dd, J=9.1, 0.8 Hz), 8.15 (1H, s),
melting point: 103-104° C. (recrystallized from ethyl acetate/hexane),
elemental analysis: for C$_{10}$H$_9$N$_2$O$_2$Br
Calculated (%): C, 44.63; H, 3.37; N, 10.41
Found (%): C, 44.69; H, 3.30; N, 10.50.

Reference Example 4 methyl 5-bromo-2,3-dimethyl-2H-indazole-4-carboxylate

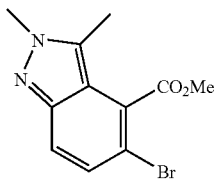

To a solution of diisopropylamine (1.38 mL, 9.73 mmol) in tetrahydrofuran (25 mL) was added 1.6M butyllithium/hexane solution (5.62 mL, 8.99 mmol) at −78° C., and the mixture was stirred for 30 min. A solution of methyl 5-bromo-2-methyl-2H-indazole-4-carboxylate (2.00 g, 7.49 mmol) in tetrahydrofuran (50 mL) was added and, after stirring for 30 min, iodomethane (933 μL, 15.0 mmol) was added. After stirring for 30 min, the reaction solution was diluted with saturated aqueous ammonium chloride solution. The solvent was evaporated under reduced pressure. The residue was diluted with ethyl acetate, washed with water and saturated brine, and dried over anhydrous sodium sulfate. The solvent was evaporated under reduced pressure, and the residue was purified by silica gel column chromatography (ethyl acetate/hexane=20/80→50/50) to give the title compound (1.10 g, yield 52%).

$^1$H-NMR (CDCl$_3$) δ: 2.48 (3H, s), 4.02 (3H, s), 4.09 (3H, s), 7.34 (1H, d, J=9.1 Hz), 7.54 (1H, d, J=9.1 Hz), melting point: 109-111° C. (recrystallized from ethyl acetate/hexane),

MS (ESI+): 283 (M+H), elemental analysis: for C$_{11}$H$_{11}$N$_2$O$_2$Br

Calculated (%): C, 46.66; H, 3.92; N, 9.89

Found (%): C, 46.67; H, 3.76; N, 9.95.

Reference Example 5 methyl 5-[(1E)-3-methoxy-3-oxoprop-1-en-1-yl]-2-methyl-2H-indazole-4-carboxylate

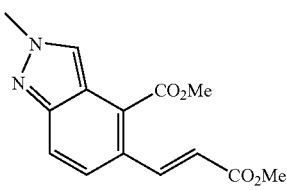

A suspension of methyl 5-bromo-2-methyl-2H-indazole-4-carboxylate (1.65 g, 6.18 mmol), palladium acetate (139 mg, 0.62 mmol), triphenylphosphine (325 mg, 1.24 mmol), potassium carbonate (1.28 g, 9.27 mmol) and methyl acrylate (834 µL, 9.27 mmol) in N,N-dimethylformamide (60 mL) was stirred with heating at 100° C. for 50 min. The reaction solution was diluted with water, extracted with ethyl acetate, washed with water and saturated brine, and dried over anhydrous magnesium sulfate. The solvent was evaporated under reduced pressure, and the residue was purified by silica gel column chromatography (ethyl acetate/hexane=30/70→70/30) to give the title compound (1.33 g, yield 78%).

$^1$H-NMR (CDCl$_3$) δ: 3.83 (3H, s), 4.03 (3H, s), 4.25 (3H, s), 6.39 (1H, d, J=15.9 Hz), 7.54 (1H, d, J=9.1 Hz), 7.85 (1H, d, J=9.1 Hz), 8.28 (1H, s), 8.61 (1H, d, J=15.9 Hz), melting point: 232-234° C. (recrystallized from ethyl acetate),

MS (ESI+): 275 (M+H), elemental analysis: for C$_{14}$H$_{14}$N$_2$O$_4$

Calculated (%): C, 61.31; H, 5.14; N, 10.21

Found (%): C, 61.02; H, 5.13; N, 10.26.

Reference Example 6 methyl 5-[(1E)-3-methoxy-3-oxoprop-1-en-1-yl]-2,3-dimethyl-2H-indazole-4-carboxylate

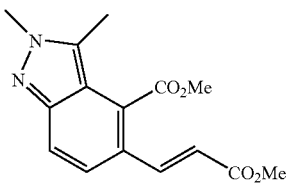

A suspension of methyl 5-bromo-2,3-dimethyl-2H-indazole-4-carboxylate (1.10 g, 3.89 mmol), palladium acetate (87.3 mg, 0.389 mmol), triphenylphosphine (204 mg, 0.778 mmol), potassium carbonate (591 mg, 4.28 mmol) and methyl acrylate (523 µL, 5.83 mmol) in N,N-dimethylformamide (39 mL) was stirred with heating at 100° C. for 4 hr. The solvent was evaporated under reduced pressure, and the residue was diluted with ethyl acetate, washed with water and saturated brine, and dried over anhydrous sodium sulfate. The solvent was evaporated under reduced pressure, and the residue was purified by silica gel column chromatography (ethyl acetate/hexane=20/80→60/40) to give the title compound (606 mg, yield 54%).

$^1$H-NMR (CDCl$_3$) δ: 2.53 (3H, s), 3.81 (3H, s), 4.05 (3H, s), 4.11 (3H, s), 6.42 (1H, d, J=15.9 Hz), 7.51 (1H, d, J=9.3 Hz), 7.68 (1H, d, J=9.3 Hz), 7.87 (1H, d, J=15.9 Hz), melting point: 133-135° C. (recrystallized from ethyl acetate/hexane),

MS (ESI+): 289 (M+H), elemental analysis: for C$_{15}$H$_{16}$N$_2$O$_4$

Calculated (%): C, 62.49; H, 5.59; N, 9.72

Found (%): C, 62.48; H, 5.60; N, 9.79.

Reference Example 7 methyl 5-(3-methoxy-3-oxopropyl)-2-methyl-2H-indazole-4-carboxylate

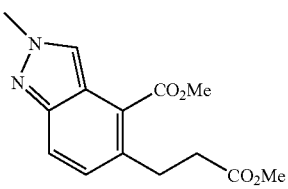

To a solution of methyl 5-[(1E)-3-methoxy-3-oxoprop-1-en-1-yl]-2-methyl-2H-indazole-4-carboxylate (1.02 g, 3.72 mmol) in methanol (40 mL) was added palladium-carbon powder (100 mg), and the mixture was stirred under a hydrogen atmosphere at room temperature for 12 hr. The catalyst was filtered off, and the filtrate was concentrated under reduced pressure. The residue was purified by silica gel column chromatography (ethyl acetate) to give the title compound (813 mg, yield 79%).

$^1$H-NMR (CDCl$_3$) δ: 2.61-2.74 (2H, m), 3.30-3.42 (2H, m), 3.67 (3H, s), 3.99 (3H, s), 4.23 (3H, s), 7.21 (1H, d, J=8.0 Hz), 7.79 (1H, d, J=8.0 Hz), 8.20 (1H, s),

MS (ESI+): 277 (M+H).

Reference Example 8 methyl 5-(3-methoxy-3-oxopropyl)-2,3-dimethyl-2H-indazole-4-carboxylate

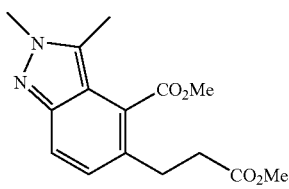

To a solution of methyl 5-[(1E)-3-methoxy-3-oxoprop-1-en-1-yl]-2,3-dimethyl-2H-indazole-4-carboxylate (726 mg, 2.52 mmol) in methanol (25 mL) was added palladium-carbon powder (145 mg), and the mixture was stirred under a hydrogen atmosphere at room temperature for 18 hr. The catalyst was filtered off, and the filtrate was concentrated under reduced pressure to give the title compound (666 mg, yield 91%).

$^1$H-NMR (CDCl$_3$) δ: 2.50 (3H, s), 2.59-2.72 (2H, m), 2.92-3.07 (2H, m), 3.67 (3H, s), 3.99 (3H, s), 4.09 (3H, s), 7.11 (1H, d, J=9.1 Hz), 7.64 (1H, d, J=9.1 Hz),
MS (ESI+): 291 (M+H).

Reference Example 9

3-(acetylamino)-6-bromo-2-nitrobenzoic acid

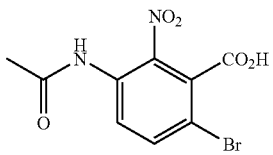

5-(Acetylamino)-2-bromobenzoic acid (5.00 g, 19.4 mmol) was gradually added to fuming nitric acid (10 mL) at 0° C., and the mixture was stirred at room temperature for 4 hr. Water was added to the reaction solution, and the precipitated crystals were collected by filtration to give the title compound (2.19 g, yield 37%).

$^1$H-NMR (CDCl$_3$) δ: (3H, s), 7.49 (1H, d, J=8.7 Hz), 7.96 (1H, d, J=8.7 Hz), 10.38 (1H, s), hidden (1H).

Reference Example 10 methyl 3-(acetylamino)-6-bromo-2-nitrobenzoate

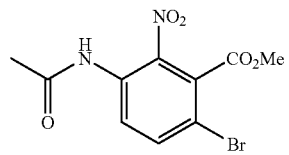

To a mixed solution of 3-(acetylamino)-6-bromo-2-nitrobenzoic acid (2.00 g, 6.60 mmol) in methanol (20 mL) and tetrahydrofuran (5 mL) was added 2M trimethylsilyldiazomethane/diethyl ether solution (10.6 mL, 21.1 mmol) under ice-cooling, and the mixture was stirred at room temperature for 5 days. The reaction solution was concentrated under reduced pressure, and the residue was purified by silica gel column chromatography (ethyl acetate/hexane=25/75→60/40) to give the title compound (1.39 g, yield 66%).

$^1$H-NMR (CDCl$_3$) δ: 2.27 (3H, s), 3.98 (3H, s), 7.79 (1H, d, J=9.2 Hz), 8.60 (1H, d, J=9.2 Hz), 9.55 (1H, s).

Reference Example 11 methyl 3-(acetylamino)-6-[(1E)-3-methoxy-3-oxo-prop-1-en-1-yl]-2-nitrobenzoate

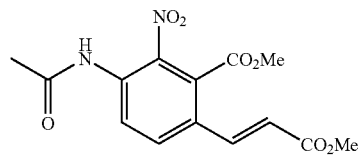

A suspension of methyl 3-(acetylamino)-6-bromo-2-nitrobenzoate (500 mg, 1.58 mmol), palladium acetate (36.0 mg, 0.16 mmol), triphenylphosphine (84.0 mg, 0.32 mmol), potassium carbonate (328 mg, 2.37 mmol) and methyl acrylate (213 μL, 2.37 mmol) in N,N-dimethylformamide (15 mL) was stirred under a nitrogen atmosphere at 110° C. for 30 min with heating. The reaction solution was diluted with water, extracted with ethyl acetate, washed with water and saturated brine, and dried over anhydrous magnesium sulfate. The solvent was evaporated under reduced pressure, and the residue was purified by silica gel column chromatography (ethyl acetate/hexane=25/75→55/45) to give the title compound (303 mg, yield 60%).

$^1$H-NMR (CDCl$_3$) δ: 2.28 (3H, s), 3.81 (3H, s), 3.97 (3H, s), 6.43 (1H, d, J=15.8 Hz), 7.66 (1H, d, J=15.8 Hz), 7.85 (1H, d, J=8.9 Hz), 8.70 (1H, d, J=8.9 Hz), 9.46 (1H, s).

Reference Example 12 methyl 3-(acetylamino)-2-amino-6-(3-methoxy-3-oxopropyl)benzoate

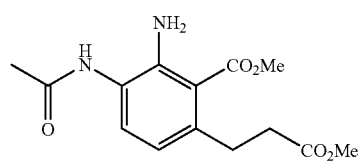

To a solution of methyl 3-(acetylamino)-6-[(1E)-3-methoxy-3-oxoprop-1-en-1-yl]-2-nitrobenzoate (686 mg, 2.13 mmol) in methanol (20 mL) was added palladium-carbon powder (20 mg), and the mixture was stirred under a hydrogen atmosphere at room temperature for 5 hr. The catalyst was filtered off, and the filtrate was concentrated under reduced pressure to give the title compound (516 mg, yield 82%).

¹H-NMR (CDCl₃) δ: 1.80-2.25 (3H, m), 2.51-2.67 (2H, m), 2.95-3.13 (2H, m), 3.68 (3H, s), 3.84-3.98 (3H, m), 5.40 (2H, brs), 6.47-6.65 (1H, m), 7.01-7.13 (1H, m), 7.21 (1H, d, J=8.1 Hz).

MS (ESI+): 295 (M+H).

Reference Example 13 methyl 6-(3-methoxy-3-oxopropyl)-2-methyl-1H-benzimidazole-7-carboxylate

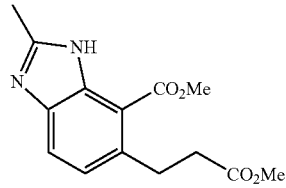

A solution of methyl 3-(acetylamino)-2-amino-6-(3-methoxy-3-oxopropyl)benzoate (490 mg, 1.66 mmol) in acetic acid (15 mL) was stirred with heating at 80° C. for 1 hr. The reaction solution was concentrated under reduced pressure, and the residue was purified by silica gel column chromatography (methanol/ethyl acetate=0/100→15/85) to give the title compound (434 mg, yield 95%).

¹H-NMR (METHANOL-d₄) δ: 2.55-2.74 (5H, m), 3.23-3.33 (3H, m), 3.41 (2H, t, J=7.7 Hz), 3.63 (3H, s), 7.20 (1H, d, J=8.3 Hz), 7.60 (1H, d, J=8.3 Hz), hidden (1H).

Reference Example 14 methyl 1-benzyl-5-(3-methoxy-3-oxopropyl)-2-methyl-1H-benzimidazole-4-carboxylate

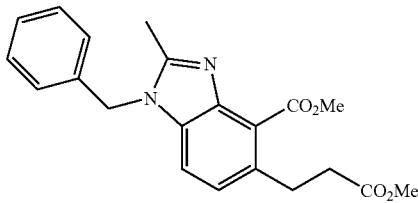

To a solution of methyl 6-(3-methoxy-3-oxopropyl)-2-methyl-1H-benzimidazole-7-carboxylate (417 mg, 1.51 mmol) in acetonitrile (15 mL) were added potassium carbonate (62.6 mg, 0.453 mmol) and benzyl bromide (269 μL, 2.26 mmol), and the mixture was stirred at 80° C. for 3 hr. The reaction solution was diluted with saturated aqueous sodium hydrogen carbonate solution, extracted with ethyl acetate, washed with water and saturated brine, and dried over anhydrous magnesium sulfate. The solvent was evaporated under reduced pressure, and the residue was purified by silica gel column chromatography (methanol/ethyl acetate=0/100→5/95) to give the title compound (164 mg, yield 30%).

¹H-NMR (CDCl₃) δ: 2.59 (3H, s), 2.63-2.72 (2H, m), 3.09-3.21 (2H, m), 3.66 (3H, s), 4.06 (3H, s), 5.30 (2H, s), 6.98-7.05 (2H, m), 7.09 (1H, d, J=8.2 Hz), 7.21 (1H, d, J=8.2 Hz), 7.24-7.33 (3H, m),

MS (ESI+): 367 (M+H).

Reference Example 15 methyl 4-(3-ethoxy-3-oxopropyl)nicotinate

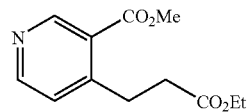

Under an argon gas atmosphere, a mixture of zinc (21.0 g, 321 mmol) and 1,2-dibromoethane (1.40 mL, 16.2 mmol) in tetrahydrofuran (105 mL) was stirred at 80° C. for 20 min. After cooling to room temperature, chlorotrimethylsilane (400 μL, 3.13 mmol) was added at room temperature, and the mixture was stirred for 30 min. A solution of ethyl 3-iodopropanoate (60.0 g, 263 mmol) in tetrahydrofuran (53 mL) was added dropwise to the mixture at room temperature, and the mixture was stirred at 40° C. for 3 hr. A solution of copper(I) cyanide (19.2 g, 214 mmol) and lithium chloride (18.3 g, 432 mmol) in tetrahydrofuran (50 mL) was added dropwise to the mixture at 0° C., and the mixture was stirred for 30 min. This mixture was added dropwise at −78° C. under an argon gas atmosphere to a mixture obtained by stirring a solution of ethyl chlorocarbonate (19.4 mL, 203 mmol) and methyl nicotinate (27.8 g, 203 mmol) in tetrahydrofuran (105 mL) at 0° C. for 30 min, and the mixture was stirred for 12 hr while heating to room temperature. The reaction solution was diluted with saturated aqueous sodium hydrogen carbonate solution, and the mixture was filtered. The filtrate was concentrated under reduced pressure, and the insoluble material was filtered off. The filtrate was extracted with ethyl acetate, and the extract was dried over anhydrous sodium sulfate. The solvent was evaporated under reduced pressure. Xylene (105 mL) and sulfur (20.0 g, 624 mmol) were added to the residue, and the mixture was stirred at 140° C. for 12 hr. After cooling to room temperature, the insoluble material was filtered off, and the filtrate was concentrated under reduced pressure. The residue was purified by silica gel column chromatography (ethyl acetate/hexane=10/90→30/70) to give the title compound (20.5 g, yield 43%).

¹H-NMR (CDCl₃) δ: 1.23 (3H, t, J=7.1 Hz), 2.67 (2H, t, J=7.6 Hz), 3.30 (2H, t, J=7.6 Hz), 3.94 (3H, s), 4.12 (2H, q, J=7.1 Hz), 7.24 (1H, d, J=5.2 Hz), 8.60 (1H, d, J=5.2 Hz), 9.09 (1H, s).

Reference Example 16 methyl 6-aminopyridine-2-carboxylate

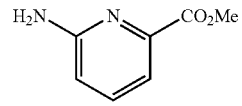

A solution of 6-methylpyridin-2-amine (25 g, 231 mmol) and acetic anhydride (44 mL, 465 mmol) in tetrahydrofuran (188 mL) was heated under reflux for 12 hr. The solvent was evaporated under reduced pressure, and the residue was diluted with ethyl acetate, and washed with saturated aqueous sodium hydrogen carbonate solution and saturated brine. This was dried over anhydrous sodium sulfate and the solvent was evaporated under reduced pressure. Water (350 mL) was added to the obtained crystals, and the mixture was heated to 75° C., and potassium permanganate (87.1 g, 551 mmol) was gradually added over 45 min. The mixture was stirred for 3 hr, and filtered through celite, and the filtrate was concentrated. Hydrochloric acid/methanol solution (Tokyo Chemical Industry Co., Ltd., 350 mL) was added, and the mixture was heated under reflux for 24 hr. The reaction solution was concentrated, diluted with ethyl acetate, and washed with saturated aqueous sodium hydrogen carbonate solution. The aqueous layer was extracted with ethyl acetate. The obtained organic layers were mixed, washed with saturated brine, and dried over anhydrous sodium sulfate. The solvent was evaporated under reduced pressure, and the residue was purified by silica gel column chromatography to give the title compound (6.28 g, yield 18%).

$^1$H-NMR (CDCl$_3$) δ: 3.96 (3H, s), 4.72 (2H, brs), 6.67 (1H, dd, J=8.0, 1.1 Hz), 7.47-7.59 (2H, m).

Reference Example 17 methyl 6-amino-3-bromopyridine-2-carboxylate

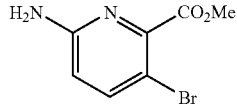

To a suspension of methyl 6-aminopyridine-2-carboxylate (5.98 g, 39.5 mmol) and sodium carbonate (2.64 g, 24.9 mmol) in acetic acid (150 mL) was added bromine (7.89 g, 49.4 mmol), and the mixture was stirred at room temperature for 7 hr. The solvent was evaporated under reduced pressure, and the residue was diluted with ethyl acetate, and washed with saturated aqueous sodium hydrogen carbonate solution and saturated brine. This was dried over anhydrous sodium sulfate and the solvent was evaporated under reduced pressure. The residue was purified by silica gel column chromatography (ethyl acetate/hexane=30/70→80/20) to give the title compound (2.67 g, yield 29%).

$^1$H-NMR (CDCl$_3$) δ: 3.95 (3H, s), 4.74 (2H, brs), 6.49 (1H, d, J=8.8 Hz), 7.62 (1H, d, J=8.8 Hz),
MS (ESI+): 231 (M+H).

Reference Example 18 methyl 3-bromo-6-(dibenzylamino)pyridine-2-carboxylate

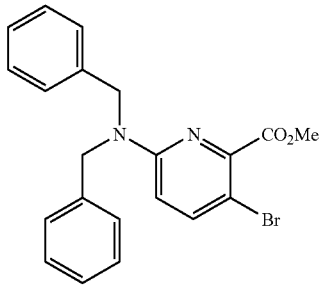

To a suspension of 60% sodium hydride (880 mg, 22.0 mmol) and benzyl bromide (6.24 mL, 52.5 mmol) in N,N-dimethylformamide (80 mL) was added a solution of methyl 6-amino-3-bromopyridine-2-carboxylate (2.42 g, 10.5 mmol) in N,N-dimethylformamide (25 mL) under ice-cooling and the mixture was stirred for 30 min. The reaction solution was diluted with diethyl ether, washed with water and saturated brine, and dried over anhydrous sodium sulfate. The solvent was evaporated under reduced pressure, and the residue was purified by silica gel column chromatography (ethyl acetate/hexane=0/100→20/80) to give the title compound (3.16 g, yield 73%).

$^1$H-NMR (CDCl$_3$) δ: 3.96 (3H, s), 4.77 (4H, s), 6.39 (1H, d, J=9.1 Hz), 7.18-7.37 (10H, m), 7.51 (1H, d, J=9.1 Hz),
MS (ESI+): 411 (M+H).

Reference Example 19 methyl 6-(dibenzylamino)-3-[(1E)-3-methoxy-3-oxoprop-1-en-1-yl]pyridine-2-carboxylate

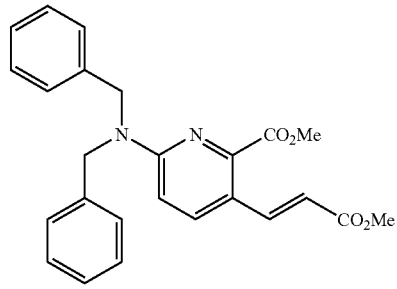

A suspension of methyl 3-bromo-6-(dibenzylamino)pyridine-2-carboxylate (3.16 g, 7.68 mmol), palladium acetate (172 mg, 0.768 mmol), triphenylphosphine (404 mg, 1.54 mmol), potassium carbonate-(1.59 g, 11.5 mmol) and methyl acrylate (1.21 mL, 15.4 mmol) in N,N-dimethylformamide (77 mL) was stirred with heating at 120° C. for 12 hr. The reaction solution was diluted with diethyl ether, washed with water and saturated brine, and dried over anhydrous sodium sulfate. The solvent was evaporated under reduced pressure, and the residue was purified by silica gel column chromatography (ethyl acetate/hexane=10/90→40/60) to give the title compound (2.60 g, yield 81%).

$^1$H-NMR (CDCl$_3$) δ: 3.78 (3H, s), 3.98 (3H, s), 4.83 (4H, s), 6.17 (1H, d, J=15.7 Hz), 6.58 (1H, d, J=9.1 Hz), 7.20-7.36 (10H, m), 7.68 (1H, d, J=9.1 Hz), 8.11 (1H, d, J=15.7 Hz).

Reference Example 20 methyl 6-(dibenzylamino)-3-(3-methoxy-3-oxopropyl)pyridine-2-carboxylate

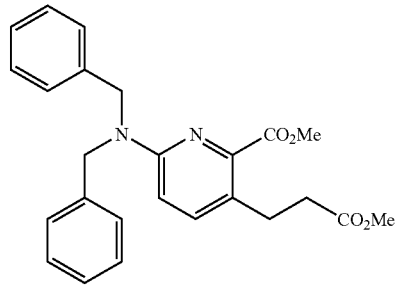

To a solution of methyl 6-(dibenzylamino)-3-[(1E)-3-methoxy-3-oxoprop-1-en-1-yl]pyridine-2-carboxylate (2.60 g, 6.24 mmol) and nickel(II) chloride hexahydrate (891 mg, 3.75 mmol) in methanol (62 mL) was added sodium tetrahydroborate (472 mg, 12.5 mmol) under ice-cooling, and the mixture was stirred for 5 min. The reaction solution was diluted with saturated aqueous ammonium chloride solution, and the organic solvent was evaporated under reduced pressure. The residue was diluted with ethyl acetate, washed with saturated brine, and dried over anhydrous sodium sulfate. The solvent was evaporated under reduced pressure, and the residue was purified by silica gel column chromatography (ethyl acetate/hexane=10/90→30/70) to give the title compound (2.24 g, yield 86%).

$^{1}$H-NMR (CDCl$_{3}$) δ: 2.64 (2H, t, J=7.6 Hz), 3.04 (2H, t, J=7.6 Hz), 3.66 (3H, s), 3.92 (3H, s), 4.79 (4H, s), 6.51 (1H, d, J=8.8 Hz), 7.14-7.40 (11H, m),

MS (ESI+): 419 (M+H).

Reference Example 21

2-methyl-6,7-dihydrocyclopenta[e]indazol-8(2H)-one

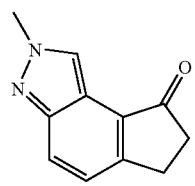

To a suspension of 60% sodium hydride (145 mg, 3.62 mmol) in tetrahydrofuran (10 mL) were added a solution of methyl 5-(3-methoxy-3-oxopropyl)-2-methyl-2H-indazole-4-carboxylate (500 mg, 1.81 mmol) in tetrahydrofuran (10 mL) and methanol (1 drop), and the mixture was heated under reflux for 3 hr. The reaction solution was concentrated to dryness to give yellow-brown crystals. The obtained crystals were gradually added to 12M hydrochloric acid (5 mL) heated to 100° C., and the mixture was stirred for 4 hr. The reaction solution was neutralized with 8M aqueous sodium hydroxide solution, and the mixture was extracted with ethyl acetate. The extract was washed with saturated brine, and dried over anhydrous magnesium sulfate. The solvent was evaporated under reduced pressure, and the residue was purified by silica gel column chromatography (ethyl acetate) to give the title compound (285 mg, yield 85%).

$^{1}$H-NMR (CDCl$_{3}$) δ: 2.65-2.80 (2H, m), 3.14-3.25 (2H, m), 4.25 (3H, s), 7.36 (1H, d, J=8.9 Hz), 7.95 (1H, d, J=8.9 Hz), 8.36 (1H, s), melting point: 162-164° C. (recrystallized from ethyl acetate),

MS (ESI+): 187 (M+H), elemental analysis: for C$_{11}$H$_{10}$N$_{2}$O

Calculated (%): C, 70.95; H, 5.41; N, 15.04

Found (%): C, 70.87; H, 5.37; N, 15.16.

Reference Example 22

1,2-dimethyl-6,7-dihydrocyclopenta[e]indazol-8(2H)-one

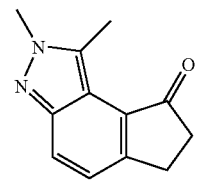

To a suspension of methyl 5-(3-methoxy-3-oxopropyl)-2,3-dimethyl-2H-indazole-4-carboxylate (666 mg, 2.29 mmol) and 60% sodium hydride (183 mg, 4.59 mmol) in tetrahydrofuran (23 mL) was added methanol (1 drop), and the mixture was heated under reflux for 3 hr. The reaction solution was concentrated to dryness to give yellow-brown crystals. The obtained crystals were gradually added to 12M hydrochloric acid (12 mL) heated to 100° C., and the mixture was stirred for 1 hr. The reaction solution was neutralized with 1M aqueous sodium hydroxide solution, and extracted with ethyl acetate. The extract was washed with saturated brine, and dried over anhydrous sodium sulfate. The solvent was evaporated under reduced pressure, and the residue was purified by silica gel column chromatography (ethyl acetate/hexane=20/80→70/30) to give the title compound (364 mg, yield 79%).

$^{1}$H-NMR (CDCl$_{3}$) δ: 2.64-2.78 (2H, m), 3.04 (3H, s), 3.11-3.23 (2H, m), 4.09 (3H, s), 7.26 (1H, d, J=8.8 Hz), 7.83 (1H, d, J=8.8 Hz), melting point: 157-159° C. (recrystallized from ethyl acetate/hexane),

MS (ESI+): 201 (M+H), elemental analysis: for C$_{12}$H$_{12}$N$_{2}$O

Calculated (%): C, 71.98; H, 6.04; N, 13.99

Found (%): C, 71.88; H, 6.00; N, 14.04.

Reference Example 23

3-benzyl-2-methyl-6,7-dihydroindeno[4,5-d]imidazol-8(3H)-one

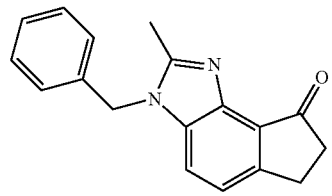

To a suspension of 60% sodium hydride (33 mg, 0.81 mmol) in tetrahydrofuran (5 mL) were added a solution of methyl 1-benzyl-5-(3-methoxy-3-oxopropyl)-2-methyl-1H-benzimidazole-4-carboxylate (148 mg, 0.40 mmol) in tetrahydrofuran (3 mL) and methanol (1 drop), and the mixture was heated under reflux for 2.5 hr. The reaction solution was concentrated to dryness to give yellow-brown crystals. The obtained crystals were gradually added to 12M hydrochloric acid (3 mL) heated to 100° C., and the mixture was stirred for 2 hr. The reaction solution was neutralized with 8M aqueous sodium hydroxide solution, and extracted with ethyl acetate. The extract was washed with saturated brine, and dried over anhydrous magnesium sulfate. The solvent was evaporated under reduced pressure to give the title compound (62 mg, yield 56%).

$^1$H-NMR (CDCl$_3$) δ: 2.66 (3H, s), 2.74-2.84 (2H, m), 3.17-3.26 (2H, m), 5.38 (2H, s), 6.95-7.07 (1H, m), 7.17-7.36 (5H, m), 7.43 (1H, d, J=8.1 Hz),

MS (ESI+): 277 (M+H).

Reference Example 24

(2-methyl-6,7-dihydrocyclopenta[e]indazol-8(2H)-ylidene)acetonitrile

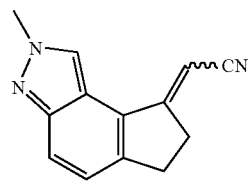

To a suspension of 60% sodium hydride (116 mg, 2.90 mmol) in tetrahydrofuran (8 mL) was added diethyl cyanomethylphosphonate (516 μL, 3.19 mmol), and the mixture was stirred at room temperature for 30 min. A solution of 2-methyl-6,7-dihydrocyclopenta[e]indazol-8(2H)-one (180 mg, 0.97 mmol) in tetrahydrofuran (2 mL) was added thereto, and the mixture was stirred at 50° C. for 30 min. The reaction solution was diluted with water, extracted with ethyl acetate, washed with water and saturated brine, and dried over anhydrous sodium sulfate. The solvent was evaporated under reduced pressure, and the residue was purified by silica gel column chromatography (ethyl acetate/hexane=35/65→70/30) to give the title compound (138 mg, yield 68%).

$^1$H-NMR (CDCl$_3$) δ: 3.16-3.21 (4H, m), 4.27 (3H, s), 5.53 (1H, s), 7.29 (1H, d, J=8.9 Hz), 7.79 (1H, d, J=8.9 Hz), 8.00 (1H, s), melting point: 189-192° C. (recrystallized from ethyl acetate/hexane),

MS (ESI+): 210 (M+H), elemental analysis: for C$_{13}$H$_{11}$N$_3$

Calculated (%): C, 74.62; H, 5.30; N, 20.08

Found (%): C, 74.48; H, 5.27; N, 20.16.

Reference Example 25

(1,2-dimethyl-6,7-dihydrocyclopenta[e]indazol-8(2H)-ylidene)acetonitrile

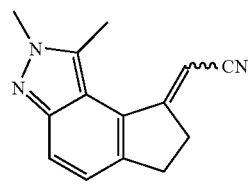

To a suspension of 60% sodium hydride (58.1 mg, 1.45 mmol) in tetrahydrofuran (4 mL) was added diethyl cyanomethylphosphonate (255 μL, 1.58 mmol), and the mixture was stirred at room temperature for 15 min. A solution of 1,2-dimethyl-6,7-dihydrocyclopenta[e]indazol-8(2H)-one (243 mg, 1.21 mmol) in tetrahydrofuran (8 mL) was added thereto, and the mixture was stirred at 60° C. for 24 hr. The reaction solution was diluted with saturated aqueous sodium hydrogen carbonate solution, extracted with ethyl acetate, washed with water and saturated brine, and dried over anhydrous sodium sulfate. The solvent was evaporated under reduced pressure, and the residue was purified by silica gel column chromatography (ethyl acetate/hexane=30/70→80/20) to give the title compound (122 mg) as a mixture with 1,2-dimethyl-6,7-dihydrocyclopenta[e]indazol-8(2H)-one. The obtained title compound was used for the reaction of Reference Example 28 without purification.

MS (ESI+): 224 (M+H).

Reference Example 26

(3-benzyl-2-methyl-6,7-dihydroindeno[4,5-d]imidazol-8(3H)-ylidene)acetonitrile

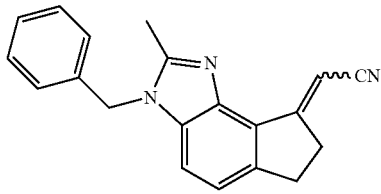

To a suspension of 60% sodium hydride (32 mg, 0.80 mmol) in tetrahydrofuran (5 mL) was added diethyl cyanomethylphosphonate (142 μL, 0.88 mmol), and the mixture was stirred at room temperature for 30 min. A solution of 3-benzyl-2-methyl-6,7-dihydroindeno[4,5-d]imidazol-8(3H)-one (73.4 mg, 0.27 mmol) in tetrahydrofuran (2 mL) was added thereto, and the mixture was stirred at room temperature for 30 min. The reaction solution was diluted with water, extracted with ethyl acetate, washed with water and saturated brine, and dried over anhydrous sodium sulfate. The solvent was evaporated under reduced pressure, and the residue was purified by silica gel column chromatography (ethyl acetate/hexane=30/70→80/20) to give the title compound (53.3 mg, yield 67%).

$^1$H-NMR (CDCl$_3$) δ: 2.61 (3H, s), 3.09-3.24 (4H, m), 5.34 (2H, s), 6.63-6.70 (1H, m), 6.95-7.05 (2H, m), 7.08-7.16 (1H, m), 7.19-7.37 (4H, m),

MS (ESI+): 300 (M+H).

Reference Example 27

2-(2-methyl-6,7-dihydrocyclopenta[e]indazol-8(2H)-ylidene)ethanamine

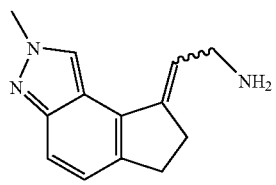

To a solution of (2-methyl-6,7-dihydrocyclopenta[e]indazol-8(2H)-ylidene)acetonitrile (600 mg, 2.87 mmol) in ethanol (14 mL) were added Raney cobalt (6 g) and 2M ammonia/ethanol solution (14 mL), and the mixture was stirred under a hydrogen atmosphere at room temperature for 3 hr. The catalyst was filtered off through celite, and the filtrate was concentrated under reduced pressure to give the title compound (614 mg, yield 99%).

$^1$H-NMR (CDCl$_3$) δ: 2.77-2.89 (2H, m), 3.01-3.15 (2H, m), 3.55 (2H, d, J=6.9 Hz), 4.23 (3H, s), 5.89-6.01 (1H, m), 7.20 (1H, d, J=8.8 Hz), 7.57 (1H, d, J=8.8 Hz), 8.11 (1H, s), hidden (2H),

MS (ESI+): 214 (M+H).

Reference Example 28

2-(1,2-dimethyl-6,7-dihydrocyclopenta[e]indazol-8 (2H)-ylidene)ethanamine

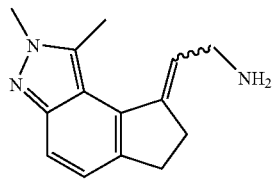

To a solution of (1,2-dimethyl-6,7-dihydrocyclopenta[e]indazol-8(2H)-ylidene)acetonitrile obtained in Reference Example 25 in ethanol (2.5 mL) were added Raney cobalt (1.2 g) and 2M ammonia/ethanol solution (2.5 mL), and the mixture was stirred under a hydrogen atmosphere at room temperature for 3 hr. The catalyst was filtered off through celite, and the filtrate was concentrated under reduced pressure to give the title compound. The obtained title compound was used for the reaction of Example 7 without purification.

MS (ESI+): 228 (M+H).

Reference Example 29

5,6-dihydro-7H-cyclopenta[c]pyridin-7-one

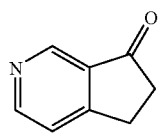

A solution of methyl 4-(3-ethoxy-3-oxopropyl)nicotinate (4.80 g, 20.2 mmol) in tetrahydrofuran (100 mL) was added to a suspension of 60% sodium hydride (3.73 g, 93.3 mmol) in tetrahydrofuran (50 mL) at room temperature. Methanol (100 μL) was added to the mixture at room temperature, and the mixture was heated under reflux for 4 hr. After cooling to room temperature, the mixture was concentrated under reduced pressure. The residue was added to 12M hydrochloric acid (50 mL) at 0° C., and the mixture was stirred at 110° C. for 30 min. The mixture was alkalified with sodium hydrogen carbonate, the insoluble material was filtered off, and the filtrate was extracted with ethyl acetate. The extract was dried over anhydrous sodium sulfate, and the solvent was evaporated under reduced pressure. The residue was washed with hexane to give the title compound (1.57 g, yield 58%).

$^1$H-NMR (CDCl$_3$) δ: 2.66-2.76 (2H, m), 3.14-3.23 (2H, m), 7.42-7.50 (1H, m), 8.71 (1H, d, J=5.2 Hz), 9.00 (1H, d, J=0.8 Hz).

Reference Example 30

2-(dibenzylamino)-5,6-dihydro-7H-cyclopenta[b]pyridin-7-one

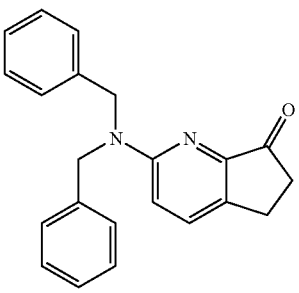

To a suspension of methyl 6-(dibenzylamino)-3-(3-methoxy-3-oxopropyl)pyridine-2-carboxylate (2.02 g, 4.83 mmol) and 60% sodium hydride (386 mg, 9.65 mmol) in tetrahydrofuran (48 mL) was added methanol (1 drop), and the mixture was heated under reflux for 1.5 hr. The reaction solution was concentrated to dryness, 12M hydrochloric acid (24 mL) was added, and the mixture was stirred at 110° C. for 15 min. The reaction solution was diluted with ethyl acetate, neutralized with saturated aqueous sodium hydrogen carbonate solution, and washed with saturated brine. This was dried over anhydrous sodium sulfate, and the solvent was evaporated under reduced pressure. The residue was purified by silica gel column chromatography (ethyl acetate/hexane=10/90→40/60) to give the title compound (1.17 g, yield 74%).

$^1$H-NMR (CDCl$_3$) δ: 2.64-2.75 (2H, m), 2.91-3.03 (2H, m), 4.87 (4H, s), 6.68 (1H, d, J=8.8 Hz), 7.15-7.34 (10H, m), 7.51 (1H, d, J=8.8 Hz),

MS (ESI+): 329 (M+H).

Reference Example 31

6,7-dihydro-5H-cyclopenta[c]pyridin-7-ylacetonitrile

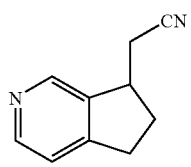

To a solution of diethyl cyanomethylphosphonate (346 mg, 1.95 mmol) in tetrahydrofuran (10 mL) was added 60% sodium hydride (54.0 mg, 1.35 mmol) under ice-cooling, and the mixture was stirred at room temperature for 30 min. The mixture was added to a solution of 5,6-dihydro-7H-cyclopenta[c]pyridin-7-one (130 mg, 0.976 mmol) in tetrahydrofuran (5 mL) under ice-cooling, and the mixture was stirred for 15 min. The reaction solution was diluted with saturated aqueous sodium hydrogen carbonate solution, and the mixture was extracted with ethyl acetate. The extract was dried over anhydrous sodium sulfate, and the solvent was evaporated under reduced pressure. The residue was purified by silica gel column chromatography (ethyl acetate/hexane=50/50→80/20). To a solution of the purified product in methanol (10 mL) was added palladium-carbon powder (30 mg), and the mixture was stirred under a hydrogen atmosphere at room temperature for 4 hr. The catalyst was filtered off, and the filtrate was evaporated under reduced pressure. The residue was purified by silica gel column chromatography (ethyl acetate/hexane=40/60→70/30) to give the title compound (95.0 mg, yield 62%).

$^1$H-NMR (CDCl$_3$) δ: 1.87-2.03 (1H, m), 2.42-3.14 (5H, m), 3.53-3.66 (1H, m), 7.22 (1H, dd, J=4.9, 0.8 Hz), 8.46 (1H, d, J=4.9 Hz), 8.55 (1H, s).

Reference Example 32

[2-(dibenzylamino)-5,6-dihydro-7H-cyclopenta[b]pyridin-7-ylidene]acetonitrile

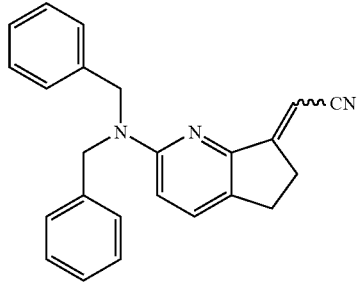

To a suspension of 60% sodium hydride (146 mg, 3.65 mmol) in tetrahydrofuran (20 mL) was added diethyl cyanomethylphosphonate (640 μL, 3.96 mmol), and the mixture was stirred at room temperature for 15 min. A solution of 2-(dibenzylamino)-5,6-dihydro-7H-cyclopenta[b]pyridin-7-one (1.00 g, 3.04 mmol) in tetrahydrofuran (10 mL) was added thereto, and the mixture was further stirred for 15 min. The reaction solution was diluted with saturated aqueous ammonium chloride solution, diluted with ethyl acetate, washed with saturated brine, and dried over anhydrous sodium sulfate. The solvent was evaporated under reduced pressure, and the residue was purified by silica gel column chromatography (ethyl acetate/hexane=10/90→30/70) to give the title compound (1.01 g, yield 95%).

$^1$H-NMR (CDCl$_3$) δ: 2.87-2.99 (2H, m), 3.00-3.12 (2H, m), 4.82 (4H, s), 5.99 (1H, t, J=2.7 Hz), 6.52 (1H, d, J=8.7 Hz), 7.17-7.41 (11H, m),
MS (ESI+): 352 (M+H).

Reference Example 33

[2-(dibenzylamino)-6,7-dihydro-5H-cyclopenta[b]pyridin-7-yl]acetonitrile

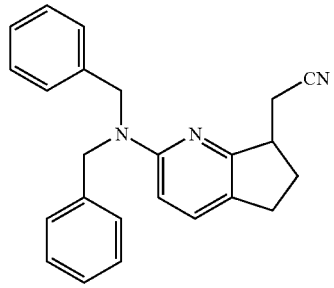

[2-(Dibenzylamino)-5,6-dihydro-7H-cyclopenta[b]pyridin-7-ylidene]acetonitrile (1.01 g, 2.87 mmol) was dissolved in methanol (40 mL), 20% palladium hydroxide-carbon powder (200 mg) was added, and the mixture was stirred under a hydrogen atmosphere at room temperature for 60 hr. The catalyst was filtered off, and the filtrate was concentrated under reduced pressure to give the title compound. The obtained title compound was used for the reaction of Reference Example 34 without purification.

$^1$H-NMR (CDCl$_3$) δ: 1.81-1.97 (1H, m), 2.42-2.63 (2H, m), 2.71-2.85 (2H, m), 2.90 (1H, dd, J=16.8, 4.4 Hz), 3.26-3.40 (1H, m), 4.71 (2H, d, J=16.2 Hz), 4.85 (2H, d, J=16.2 Hz), 6.28 (1H, d, J=8.5 Hz), 7.19-7.38 (11H, m).

Reference Example 34

7-(2-aminoethyl)-N,N-dibenzyl-6,7-dihydro-5H-cyclopenta[b]pyridin-2-amine

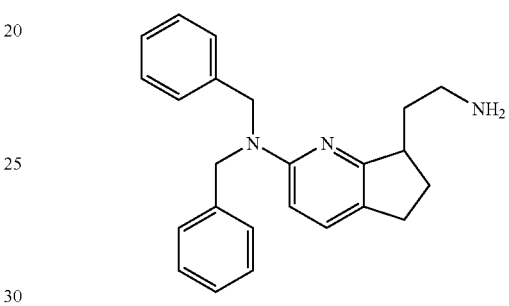

To a solution of [2-(dibenzylamino)-6,7-dihydro-5H-cyclopenta[b]pyridin-7-yl]acetonitrile obtained in Reference Example 33 in ethanol (14 mL) were added Raney cobalt (10 g) and 2M ammonia/ethanol solution (14 mL), and the mixture was stirred under a hydrogen atmosphere at room temperature for 10 hr. The catalyst was filtered off through celite, and the filtrate was concentrated under reduced pressure to give the title compound. The obtained title compound was used for the reaction of Reference Example 35 without purification.

$^1$H-NMR (CDCl$_3$) δ: 1.51-1.75 (2H, m), 1.95-2.11 (1H, m), 2.24-2.40 (1H, m), 2.60-2.89 (4H, m), 2.97-3.12 (1H, m), 4.70 (2H, d, J=16.2 Hz), 4.88 (2H, d, J=16.2 Hz), 6.22 (1H, d, J=8.5 Hz), 7.14-7.39 (11H, m), hidden (2H).

Reference Example 35

N-{2-[2-(dibenzylamino)-6,7-dihydro-5H-cyclopenta[b]pyridin-7-yl]ethyl}acetamide

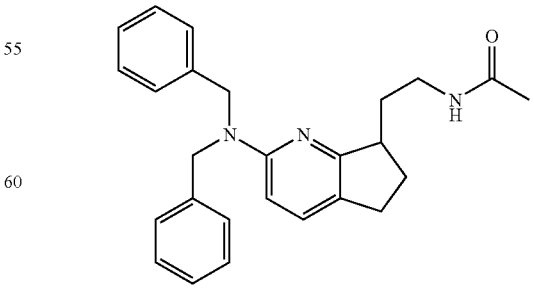

7-(2-Aminoethyl)-N,N-dibenzyl-6,7-dihydro-5H-cyclopenta[b]pyridin-2-amine obtained in Reference Example 34 was dissolved in tetrahydrofuran (28 mL), triethylamine (441 μL, 3.16 mmol) and acetic anhydride (298 μL, 3.16 mmol) were added, and the mixture was stirred at room temperature for 15 min. The reaction solution was diluted with saturated aqueous sodium hydrogen carbonate solution, diluted with ethyl acetate, washed with saturated brine, and dried over anhydrous sodium sulfate. The solvent was evaporated under reduced pressure, and the residue was purified by silica gel column chromatography (ethyl acetate/hexane=30/70→70/30) to give the title compound (0.91 g, total yield from Reference Example 33, 79%).

$^1$H-NMR (CDCl$_3$) δ: 1.60-1.91 (3H, m), 1.75 (3H, s), 2.24-2.37 (1H, m), 2.62-2.85 (2H, m), 2.94-3.07 (1H, m), 3.12-3.28 (1H, m), 3.40-3.56 (1H, m), 4.73 (2H, d, J=16.5 Hz), 4.85 (2H, d, J=16.5 Hz), 6.04 (1H, brs), 6.29 (1H, d, J=8.5 Hz), 7.17-7.36 (11H, m).

Reference Example 36

N-[2-(2-amino-6,7-dihydro-5H-cyclopenta[b]pyridin-7-yl)ethyl]acetamide

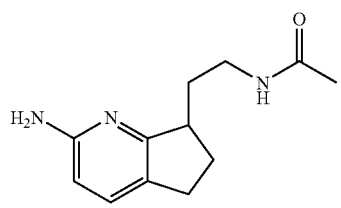

(N-{2-[2-(Dibenzylamino)-6,7-dihydro-5H-cyclopenta[b]pyridin-7-yl]ethyl}acetamide (870 mg, 2.18 mmol) was dissolved in acetic acid (22 mL), 20% palladium hydroxide-carbon powder (220 mg) was added, and the mixture was stirred under a hydrogen atmosphere at room temperature for 20 hr. The catalyst was filtered off, and the filtrate was concentrated under reduced pressure, diluted with ethyl acetate, and washed with saturated aqueous sodium hydrogen carbonate solution and saturated brine. This was dried over anhydrous sodium sulfate and the solvent was evaporated under reduced pressure to give the title compound (35.3 mg, yield 7%).

$^1$H-NMR (CDCl$_3$) δ: 1.71-1.94 (3H, m) 2.00 (3H, s) 2.25-2.40 (1H, m) 2.60-2.83 (2H, m) 2.94-3.07 (1H, m) 3.25-3.40 (1H, m) 3.40-3.55 (1H, m) 4.28 (2H, brs) 6.31 (1H, d, J=8.3 Hz) 7.28 (1H, d, J=8.3 Hz) 7.66 (1H, brs).

Reference Example 37 ethyl 9-(cyanomethyl)-8,9-dihydro-7H-cyclopenta[c]pyrazolo[1,5-a]pyridine-1-carboxylate

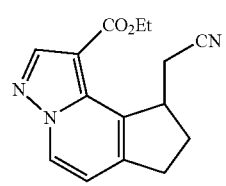

To a solution of 6,7-dihydro-5H-cyclopenta[c]pyridin-7-ylacetonitrile (1.77 g, 11.2 mmol) in acetonitrile (22 mL) was added 1-(aminooxy)-2,4-dinitrobenzene (5.00 g, 25.1 mmol), and the mixture was stirred at 40° C. for 16 hr. The solvent was evaporated under reduced pressure. Half of the residue was dissolved in dimethylformamide (22 mL), ethyl propiolate (681 μL, 6.72 mmol) and potassium carbonate (1.55 g, 11.2 mmol) were added, and the mixture was stirred at room temperature for 3 hr. The reaction solution was diluted with water, and the mixture was extracted with diethyl ether. The extract was dried over anhydrous sodium sulfate, and the solvent was evaporated under reduced pressure. The residue was purified by silica gel column chromatography (ethyl acetate/hexane=10/90→50/50) to give the title compound (440 mg).

$^1$H-NMR (CDCl$_3$) δ: 1.40 (3H, t, J=7.2 Hz), 2.20-2.32 (1H, m), 2.43-2.61 (1H, m), 2.66-2.75 (1H, m), 2.80-2.91 (1H, m), 2.91-3.04 (1H, m), 3.25-3.41 (1H, m), 4.34 (2H, q, J=7.2 Hz), 4.41-4.51 (1H, m), 6.90 (1H, d, J=6.9 Hz), 8.39 (1H, s), 8.41 (1H, d, J=6.9 Hz).

Reference Example 38 ethyl 9-(cyanomethyl)-2-methyl-8,9-dihydro-7H-cyclopenta[c]pyrazolo[1,5-a]pyridine-1-carboxylate

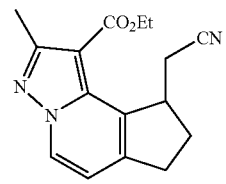

To a solution of 6,7-dihydro-5H-cyclopenta[c]pyridin-7-ylacetonitrile (90.0 mg, 0.569 mmol) in acetonitrile (1.0 mL) was added 1-(aminooxy)-2,4-dinitrobenzene (113 mg, 0.567 mmol), and the mixture was stirred at 40° C. for 12 hr. The solvent was evaporated under reduced pressure. The residue was dissolved in dimethylformamide (1.0 mL), ethyl 2-butynoate (80.0 μL, 0.686 mmol) and potassium carbonate (94.4 mg, 0.683 mmol) were added, and the mixture was stirred at room temperature for 4 hr. The reaction solution was diluted with water, and the mixture was extracted with ethyl acetate. The extract was dried over anhydrous sodium sulfate, and the solvent was evaporated under reduced pressure. The residue was purified by silica gel column chromatography (ethyl acetate/hexane=10/90→40/60) to give the title compound (51.2 mg, yield 32%).

$^1$H-NMR (CDCl$_3$) δ: 1.42 (3H, t, J=7.2 Hz), 2.18-2.31 (1H, m), 2.42-2.66 (5H, m), 2.76-2.86 (1H, m), 2.90-3.02 (1H, m), 3.20-3.36 (1H, m), 4.36 (2H, q, J=7.2 Hz), 4.44-4.56 (1H, m), 6.84 (1H, d, J=6.8 Hz), 8.31 (1H, d, J=6.8 Hz), melting point: 136-140° C. (recrystallized from ethyl acetate/hexane),

MS (ESI+): 284 (M+H), elemental analysis: for $C_{16}H_{17}N_3O_2$

Calculated (%): C, 67.83; H, 6.05; N, 14.83

Found (%): C, 67.68; H, 6.01; N, 14.86.

Reference Example 39 ethyl 9-(cyanomethyl)-2-ethyl-8,9-dihydro-7H-cyclopenta[c]pyrazolo[1,5-a]pyridine-1-carboxylate

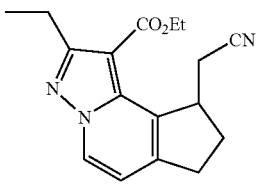

To a solution of 6,7-dihydro-5H-cyclopenta[c]pyridin-7-ylacetonitrile (1.77 g, 11.2 mmol) in acetonitrile (22 mL) was added 1-(aminooxy)-2,4-dinitrobenzene (5.00 g, 25.1 mmol), and the mixture was stirred at 40° C. for 16 hr. The solvent was evaporated under reduced pressure. Half of the residue was dissolved in dimethylformamide (22 mL), ethyl 2-pentynoate (886 µL, 6.72 mmol) and potassium carbonate (1.55 g, 11.2 mmol) were added, and the mixture was stirred at room temperature for 16 hr. The reaction solution was diluted with water, and the mixture was extracted with diethyl ether. The extract was dried over anhydrous sodium sulfate, and the solvent was evaporated under reduced pressure. The residue was purified by silica gel column chromatography (ethyl acetate/hexane=5/95→40/60) to give the title compound (644 mg).

$^{1}$H-NMR (CDCl$_{3}$) δ: 1.33 (3H, t, J=7.4 Hz), 1.41 (3H, t, J=7.2 Hz), 2.18-2.29 (1H, m), 2.40-2.63 (2H, m), 2.75-2.84 (1H, m), 2.88-2.99 (1H, m), 3.07 (2H, q, J=7.4 Hz), 3.19-3.34 (1H, m), 4.35 (2H, q, J=7.2 Hz), 4.44-4.53 (1H, m), 6.82 (1H, d, J=6.9 Hz), 8.31 (1H, d, J=6.9 Hz).

Reference Example 40 ethyl 9-(2-aminoethyl)-8,9-dihydro-7H-cyclopenta[c]pyrazolo[1,5-a]pyridine-1-carboxylate

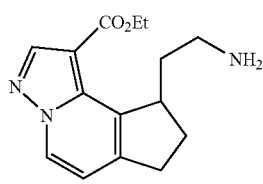

Ethyl 9-(cyanomethyl)-8,9-dihydro-7H-cyclopenta[c]pyrazolo[1,5-a]pyridine-1-carboxylate (150 mg, 0.557 mmol) and Raney cobalt (1.5 g) were suspended in 2M ammonia/ethanol solution (28 mL), and the mixture was stirred under a hydrogen atmosphere at room temperature for 12 hr. The catalyst was filtered off through celite, and the filtrate was concentrated under reduced pressure to give the title compound (150 mg, yield 99%).

$^{1}$H-NMR (CDCl$_{3}$) δ: 1.33-1.55 (4H, m), 1.71-1.93 (1H, m), 2.01-2.37 (2H, m), 2.75-3.56 (4H, m), 4.14-4.37 (3H, m), 6.84 (1H, d, J=6.9 Hz), 8.32-8.39 (2H, m), hidden (2H),

MS (ESI+): 274 (M+H).

Reference Example 41

2-(8,9-dihydro-7H-cyclopenta[c]pyrazolo[1,5-a]pyridin-9-yl)ethanamine hydrochloride

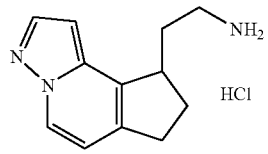

A mixture of ethyl 9-(2-aminoethyl)-8,9-dihydro-7H-cyclopenta[c]pyrazolo[1,5-a]pyridine-1-carboxylate (105 mg, 0.384 mmol) in 12M hydrochloric acid (4 mL) was stirred at 110° C. for 14 hr, and concentrated under reduced pressure to give the title compound (91.1 mg, yield 99%).

$^{1}$H-NMR (METHANOL-d$_{4}$) δ: 1.80-1.97 (1H, m), 1.98-2.14 (1H, m), 2.30-2.62 (2H, m), 2.98-3.26 (4H, m), 3.61-3.76 (1H, m), 6.98 (1H, d, J=3.3 Hz), 7.27 (1H, d, J=7.1 Hz), 8.34-8.41 (1H, m), 8.64 (1H, d, J=7.1 Hz), hidden (3H),

MS (ESI+): 202 (M+H).

Reference Example 42 ethyl 9-(2-aminoethyl)-2-methyl-8,9-dihydro-7H-cyclopenta[c]pyrazolo[1,5-a]pyridine-1-carboxylate

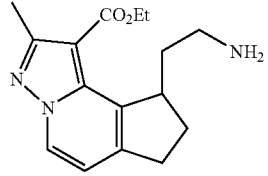

Ethyl 9-(cyanomethyl)-2-methyl-8,9-dihydro-7H-cyclopenta[c]pyrazolo[1,5-a]pyridine-1-carboxylate (145 mg, 0.512 mmol) and Raney cobalt (1.5 g) were suspended in 2M ammonia/methanol solution (50 mL), and the mixture was stirred under a hydrogen atmosphere at room temperature for 14 hr. The catalyst was filtered off through celite, and the filtrate was concentrated under reduced pressure to give the title compound (145 mg, yield 99%).

$^{1}$H-NMR (CDCl$_{3}$) δ: 1.41 (3H, t, J=7.0 Hz), 1.63-2.41 (6H, m), 2.63 (3H, s), 2.80-3.11 (2H, m), 4.14-4.42 (3H, m), 6.78 (1H, d, J=6.6 Hz), 8.23 (1H, d, J=6.6 Hz), hidden (2H),

MS (ESI+): 288 (M+H).

Reference Example 43

2-(2-methyl-8,9-dihydro-7H-cyclopenta[c]pyrazolo[1,5-a]pyridin-9-yl)ethanamine hydrochloride

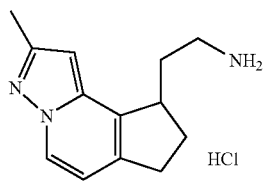

A mixture of ethyl 9-(2-aminoethyl)-2-methyl-8,9-dihydro-7H-cyclopenta[c]pyrazolo[1,5-a]pyridine-1-carboxylate (140 mg, 0.487 mmol) in 12M hydrochloric acid (5 mL) was stirred at 100° C. for 2 days, and concentrated under reduced pressure to give the title compound. The obtained title compound was used for the reaction of Example 18 without purification.

$^1$H-NMR (METHANOL-$d_4$) δ: 1.77-1.95 (1H, m), 2.00-2.12 (1H, m), 2.29-2.57 (2H, m), 2.61 (3H, s), 2.98-3.27 (4H, m), 3.61-3.74 (1H, m), 7.27 (1H, d, J=6.9 Hz), 8.56 (1H, d, J=6.9 Hz), hidden (4H),
MS (ESI+): 216 (M+H).

Reference Example 44 ethyl 9-(2-aminoethyl)-2-ethyl-8,9-dihydro-7H-cyclopenta[c]pyrazolo[1,5-a]pyridine-1-carboxylate

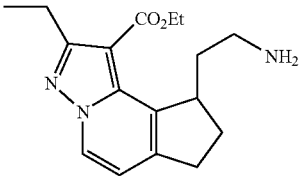

Ethyl 9-(cyanomethyl)-2-ethyl-8,9-dihydro-7H-cyclopenta[c]pyrazolo[1,5-a]pyridine-1-carboxylate (80.0 mg, 0.269 mmol) and Raney cobalt (800 mg) were suspended in 2M ammonia/ethanol solution (13 mL), and the mixture was stirred under a hydrogen atmosphere at room temperature for 4 hr. The catalyst was filtered off through celite, and the filtrate was concentrated under reduced pressure to give the title compound (81.0 mg, yield 100%).

$^1$H-NMR (CDCl$_3$) δ: 1.29-1.46 (7H, m), 1.67-1.80 (1H, m), 1.97-2.39 (2H, m), 2.64-3.16 (6H, m), 4.14-4.26 (1H, m), 4.27-4.42 (2H, m), 6.77 (1H, d, J=6.9 Hz), 8.25 (1H, d, J=6.9 Hz), hidden (2H).

Reference Example 45 methyl 5-fluoro-2-methyl-3-nitrobenzoate

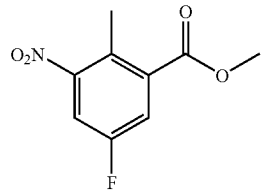

To a solution of 5-fluoro-2-methylbenzoic acid (5.00 g, 32.4 mmol) in concentrated sulfuric acid (40 mL) was added a mixture of fuming nitric acid (1.61 mL) and concentrated sulfuric acid (7.5 mL) at −10° C., and the mixture was stirred for 1 hr. The reaction solution was poured into ice-cold water, and the mixture was extracted with ethyl acetate. The extract was washed with saturated brine, and dried over anhydrous sodium sulfate. The solvent was evaporated under reduced pressure. This was dissolved in methanol (80 mL), concentrated hydrochloric acid (1.2 mL) was added, and the mixture was heated under reflux for 36 hr. The solvent was evaporated under reduced pressure, and the residue was diluted with ethyl acetate, and washed with saturated aqueous sodium hydrogen carbonate solution and saturated brine. This was dried over anhydrous sodium sulfate and the solvent was evaporated under reduced pressure to give the title compound (3.20 g, yield 46%).

$^1$H-NMR (CDCl$_3$) δ: 2.59 (3H, s), 3.95 (3H, s), 7.61 (1H, dd, J=7.3, 3.0 Hz), 7.75 (1H, dd, J=8.2, 3.0 Hz).

Reference Example 46 methyl 3-amino-5-fluoro-2-methylbenzoate

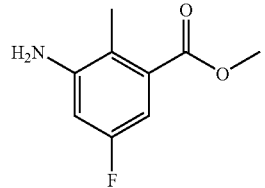

To a solution of methyl 5-fluoro-2-methyl-3-nitrobenzoate (3.20 g, 15.0 mmol) in methanol (150 mL) was added palladium-carbon powder (320 mg), and the mixture was stirred under a hydrogen atmosphere at room temperature for 4 hr. The catalyst was filtered off, and the filtrate was concentrated under reduced pressure to give the title compound (1.47 g, yield 54%).

$^1$H-NMR (CDCl$_3$) δ: 2.30 (3H, s), 3.84 (2H, brs), 3.88 (3H, s), 6.52 (1H, dd, J=9.8, 2.8 Hz), 6.91 (1H, dd, J=9.1, 2.8 Hz),
MS (ESI+): 184 (M+H).

Reference Example 47 methyl 3-amino-6-bromo-5-fluoro-2-methylbenzoate

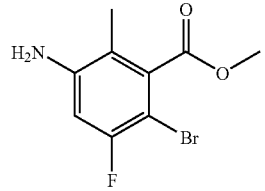

To a solution of methyl 3-amino-5-fluoro-2-methylbenzoate (1.37 g, 7.48 mmol) in acetonitrile (57 mL) was added N-bromosuccinimide (1.01 g, 5.66 mmol) under ice-cooling, and the mixture was stirred for 2 hr. The reaction solution was concentrated under reduced pressure, and the residue was purified by silica gel column chromatography (ethyl acetate/hexane=10/90→30/70) to give the title compound (1.33 g, yield 68%).

$^1$H-NMR (CDCl$_3$) δ: 2.05 (3H, s), 3.83 (2H, brs), 3.95 (3H, s), 6.49 (1H, d, J=9.9 Hz),

MS (ESI+): 262 (M+H).

Reference Example 48 methyl 5-bromo-6-fluoro-1H-indazole-4-carboxylate

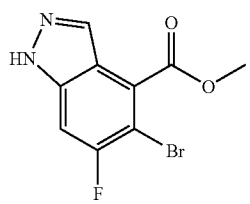

To a solution of methyl 3-amino-6-bromo-5-fluoro-2-methylbenzoate (1.33 g, 5.09 mmol) in acetic acid (25 mL) heated to 50° C. was added a solution of sodium nitrite (369 mg, 5.34 mmol) in water (1 mL), and the mixture was stirred for 1.5 hr and concentrated under reduced pressure. The residue was diluted with ethyl acetate, washed with saturated aqueous sodium hydrogen carbonate solution and saturated brine, and dried over anhydrous sodium sulfate. The solvent was evaporated under reduced pressure, and the residue was purified by silica gel column chromatography (ethyl acetate/hexane=5/95→40/60) to give the title compound (700 mg, yield 52%).

$^1$H-NMR (CDCl$_3$) δ: 4.08 (3H, s), 7.39 (1H, d, J=7.7 Hz), 8.23 (1H, s), 10.36 (1H, brs), melting point: 169-171° C. (recrystallized from ethyl acetate/hexane),

MS (ESI+): 273 (M+H), elemental analysis: for C$_9$H$_6$N$_2$O$_2$FBr.0.5H$_2$O

Calculated (%): C, 38.32; H, 2.49; N, 9.93

Found (%): C, 38.37; H, 2.48; N, 9.93.

Reference Example 49 methyl 5-bromo-6-fluoro-2-methyl-2H-indazole-4-carboxylate

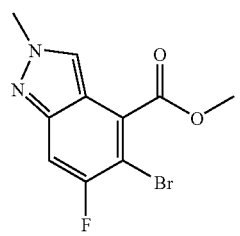

To a solution of methyl 5-bromo-6-fluoro-1H-indazole-4-carboxylate (700 mg, 2.56 mmol) in ethyl acetate (26 mL) was added trimethyloxonium tetrafluoroborate (569 mg, 3.85 mmol) at room temperature, and the mixture was stirred for 2.5 hr. The reaction solution was diluted with saturated aqueous sodium hydrogen carbonate solution, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane=10/90→50/50) to give the title compound (570 mg, yield 78%).

$^1$H-NMR (CDCl$_3$) δ: 4.03 (3H, s), 4.21 (3H, s), 7.52 (1H, dd, J=8.8, 0.8 Hz), 8.14 (1H, s), melting point: 146-147° C. (recrystallized from ethyl acetate/hexane),

MS (ESI+): 287 (M+H), elemental analysis: for C$_{10}$H$_8$N$_2$O$_2$FBr

Calculated (%): C, 41.84; H, 2.81; N, 9.76

Found (%): C, 41.78; H, 2.79; N, 9.80.

Reference Example 50 methyl 6-fluoro-5-[(1E)-3-methoxy-3-oxoprop-1-en-1-yl]-2-methyl-2H-indazole-4-carboxylate

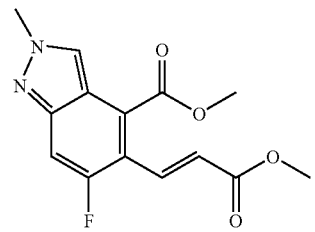

A suspension of methyl 5-bromo-6-fluoro-2-methyl-2H-indazole-4-carboxylate (503 mg, 1.75 mmol), palladium acetate (39.3 mg, 0.175 mmol), triphenylphosphine (91.8 mg, 0.350 mmol), potassium carbonate (266 mg, 1.93 mmol) and methyl acrylate (314 μL, 3.50 mmol) in N,N-dimethylformamide (8.8 mL) was stirred with heating at 100° C. for 1 hr. The reaction solution was diluted with ethyl acetate, washed with water and saturated brine, and dried over anhydrous sodium sulfate. The solvent was evaporated under reduced pressure, and the residue was purified by silica gel column chromatography (ethyl acetate/hexane=10/90→60/40) to give the title compound (452 mg, yield 88%).

$^1$H-NMR (CDCl$_3$) δ: 3.83 (3H, s), 4.02 (3H, s), 4.23 (3H, s), 6.50 (1H, dd, J=16.2, 2.7 Hz), 7.53 (1H, d, J=11.5 Hz), 8.19 (1H, d, J=16.2 Hz), 8.23 (1H, s), melting point: 130-132° C. (recrystallized from ethyl acetate/hexane),

MS (ESI+): 293 (M+H), elemental analysis: for C$_{14}$H$_{13}$N$_2$O$_4$F

Calculated (%): C, 57.53; H, 4.48; N, 9.59

Found (%): C, 57.51; H, 4.40; N, 9.60.

Reference Example 51 methyl 6-fluoro-5-(3-methoxy-3-oxopropyl)-2-methyl-2H-indazole-4-carboxylate

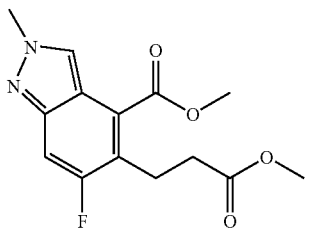

To a solution of methyl 6-fluoro-5-[(1E)-3-methoxy-3-oxoprop-1-en-1-yl]-2-methyl-2H-indazole-4-carboxylate (430 mg, 21.47 mmol) in THF/methanol (5 mL/5 mL) was added palladium-carbon powder (86 mg), and the mixture was stirred under a hydrogen atmosphere at room temperature for 18 hr. The catalyst was filtered off, and the filtrate was concentrated under reduced pressure to give the title compound (407 mg, yield 94%).

$^1$H-NMR (CDCl$_3$) δ: 2.60-2.72 (2H, m), 3.32-3.43 (2H, m), 3.69 (3H, s), 4.00 (3H, s), 4.20 (3H, s), 7.48 (1H, d, J=10.4 Hz), 8.17 (1H, s),

MS (ESI+): 294 (M+H).

Reference Example 52

5-fluoro-2-methyl-6,7-dihydrocyclopenta[e]indazol-8(2H)-one

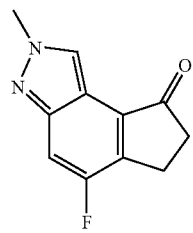

To a solution of methyl 6-fluoro-5-(3-methoxy-3-oxopropyl)-2-methyl-2H-indazole-4-carboxylate (407 mg, 1.38 mmol) in tetrahydrofuran (14 mL) was added a solution of sodium methoxide (28%, 533 mg, 2.76 mmol) in methanol, and the mixture was stirred at 60° C. for 1 hr. The reaction solution was concentrated to dryness, 10% aqueous sulfuric acid solution (14 mL) was added, and the mixture was heated under reflux for 3 hr. The reaction solution was diluted with ethyl acetate, neutralized with saturated aqueous sodium hydrogen carbonate solution, and extracted with ethyl acetate. The extract was washed with saturated brine, and dried over anhydrous sodium sulfate. The solvent was evaporated under reduced pressure to give the title compound (269 mg, yield 95%).

$^1$H-NMR (CDCl$_3$) δ: 2.78 (2H, t, J=2.0 Hz), 3.16-3.26 (2H, m), 4.24 (3H, s), 7.56 (1H, d, J=9.6 Hz), 8.35 (1H, s), melting point: 190-192° C. (recrystallized from ethyl acetate),

MS (ESI+): 205 (M+H), elemental analysis: for C$_{11}$H$_9$N$_2$OF.0.1H$_2$O

Calculated (%): C, 64.13; H, 4.49; N, 13.59

Found (%): C, 63.91; H, 4.21; N, 13.40.

Reference Example 53

(5-fluoro-2-methyl-6,7-dihydrocyclopenta[e]indazol-8(2H)-ylidene)acetonitrile

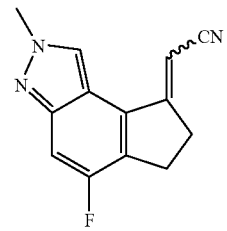

To a suspension of 60% sodium hydride (59.0 mg, 1.48 mmol) in tetrahydrofuran (8 mL) was added diethyl cyanomethylphosphonate (260 μL, 1.60 mmol) at room temperature, and the mixture was stirred for 15 min. A suspension of 5-fluoro-2-methyl-6,7-dihydrocyclopenta[e]indazol-8(2H)-one (252 mg, 1.23 mmol) in tetrahydrofuran (4 mL) was added thereto, and the mixture was stirred at room temperature for 4 hr. Saturated aqueous ammonium chloride solution was added to the reaction solution, and the mixture was diluted with ethyl acetate, washed with water and saturated brine, and dried over anhydrous sodium sulfate. The solvent was evaporated under reduced pressure. The obtained crystals were washed with diisopropyl ether to give the title compound (178 mg, yield 64%).

$^1$H-NMR (CDCl$_3$) δ: 3.22 (4H, s), 4.25 (3H, s), 5.58 (1H, s), 7.39 (1H, d, J=9.3 Hz), 8.00 (1H, s), melting point: 249-252° C. (recrystallized from tetrahydrofuran),

MS (ESI+): 228 (M+H), elemental analysis: for C$_{13}$H$_{10}$N$_3$F.0.1H$_2$O

Calculated (%): C, 68.71; H, 4.44; N, 18.49

Found (%): C, 68.46; H, 4.35; N, 18.36.

Reference Example 54

2-(5-fluoro-2-methyl-6,7-dihydrocyclopenta[e]indazol-8(2H)-ylidene)ethanamine

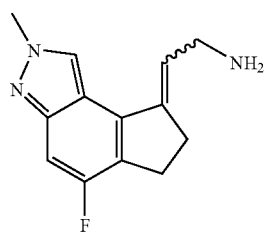

To a solution of (5-fluoro-2-methyl-6,7-dihydrocyclopenta[e]indazol-8(2H)-ylidene)acetonitrile (156 mg, 0.686 mmol) in tetrahydrofuran/methanol (5 mL/5 mL) were added Raney cobalt (1.5 g) and 2M ammonia/methanol solution (2 mL), and the mixture was stirred under a hydrogen atmosphere at room temperature for 4 hr. The catalyst was filtered off through celite, and the filtrate was concentrated under reduced pressure to give the title compound (157 mg, yield 99%).

$^1$H-NMR (CDCl$_3$) δ: 2.75-2.93 (2H, m), 3.01-3.15 (2H, m), 3.47-3.69 (2H, m), 4.20 (3H, s), 5.86-6.04 (1H, m), 7.16 (1H, d, J=9.9 Hz), 8.09 (1H, s).

Reference Example 55 methyl 3-amino-6-bromo-5-chloro-2-methylbenzoate

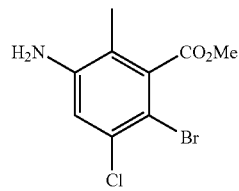

To a solution of methyl 3-amino-6-bromo-2-methylbenzoate (960 mg, 3.93 mmol) in acetonitrile (40 mL) was added N-chlorosuccinimide (525 mg, 3.93 mmol) under ice-cooling, and the mixture was stirred at 60° C. for 15 hr. The reaction mixture was diluted with ethyl acetate, washed with saturated aqueous sodium hydrogen carbonate solution, and dried over anhydrous sodium sulfate. The solvent was evaporated under reduced pressure, and the residue was purified by silica gel column chromatography (ethyl acetate/hexane=0/100→30/70) to give the title compound (1.05 g, yield 96%).

$^1$H-NMR (CDCl$_3$) δ: 2.13 (3H, s), 3.93 (3H, s), 4.13 (2H, brs), 7.36 (1H, s),

MS (ESI+): 278 (M+H).

Reference Example 56 methyl 5-bromo-6-chloro-1H-indazole-4-carboxylate

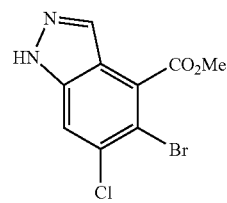

To a solution of methyl 3-amino-6-bromo-5-chloro-2-methylbenzoate (500 mg, 1.80 mmol) in acetic acid (9 mL) was added a solution of sodium nitrite (137 mg, 1.99 mmol) in water (0.9 mL) at room temperature, and the mixture was stirred for 24 hr. The organic solvent was evaporated under reduced pressure. The residual aqueous solution was diluted with saturated aqueous sodium hydrogen carbonate solution, and the mixture was extracted with ethyl acetate. The extract was washed with saturated brine, and dried over anhydrous sodium sulfate. The solvent was evaporated under reduced pressure, and the residue was purified by silica gel column chromatography (NH, ethyl acetate) to give the title compound (398 mg, yield 76%).

$^1$H-NMR (CDCl$_3$) δ: 4.05 (3H, s), 7.66 (1H, s), 8.31 (1H, s), 10.60 (1H, brs),

MS (ESI+): 289 (M+H).

Reference Example 57 methyl 5-bromo-6-chloro-2-methyl-2H-indazole-4-carboxylate

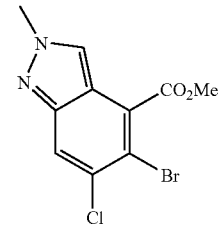

To a solution of methyl 5-bromo-6-chloro-1H-indazole-4-carboxylate (390 mg, 1.35 mmol) in ethyl acetate (27 mL) was added trimethyloxonium tetrafluoroborate (260 mg, 1.76 mmol) at room temperature, and the mixture was stirred for 2 hr. The reaction solution was diluted with ethyl acetate, washed with saturated aqueous sodium hydrogen carbonate solution, and dried over anhydrous sodium sulfate. The solvent was evaporated under reduced pressure, and the residue was purified by silica gel column chromatography (NH, ethyl acetate/hexane=10/90→40/60) to give the title compound (336 mg, yield 82%).

$^1$H-NMR (CDCl$_3$) δ: 4.00 (3H, s), 4.26 (3H, s), 7.58 (1H, s), 8.23 (1H, s), melting point: 141-142° C. (recrystallized from ethyl acetate/hexane),

MS (ESI+): 303 (M+H), elemental analysis: for C$_{10}$H$_8$N$_2$BrClO$_2$

Calculated (%): C, 39.57; H, 2.66; N, 9.23

Found (%): C, 39.48; H, 2.60; N, 9.25.

Reference Example 58 methyl 6-chloro-5-[(1E)-3-methoxy-3-oxoprop-1-en-1-yl]-2-methyl-2H-indazole-4-carboxylate

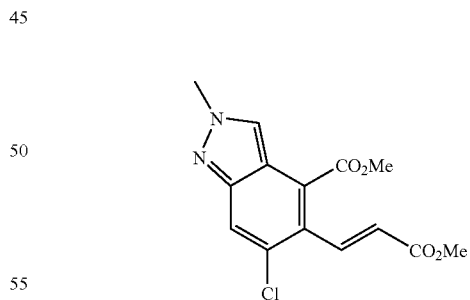

A suspension of methyl 5-bromo-6-chloro-2-methyl-2H-indazole-4-carboxylate (330 mg, 1.09 mmol), palladium acetate (24.5 mg, 0.109 mmol), triphenylphosphine (57.2 mg, 0.218 mmol), potassium carbonate (226 g, 1.64 mmol) and methyl acrylate (147 μL, 1.64 mmol) in N,N-dimethylformamide (11 mL) was stirred with heating at 100° C. for 1 hr. The reaction solution was diluted with ethyl acetate, washed with water and saturated brine, and dried over anhydrous sodium sulfate. The solvent was evaporated under reduced pressure, and the residue was purified by silica gel column chromatography (ethyl acetate/hexane=30/70→60/40) to give the title compound (270 mg, yield 80%).

$^1$H-NMR (CDCl$_3$) δ: 4.28 (3H, s), 6.37 (1H, d, J=15.9 Hz), 7.56 (1H, s), 8.34 (1H, s), 8.56 (1H, d, J=15.9 Hz),

MS (ESI+): 309 (M+H).

Reference Example 59 methyl 6-chloro-5-(3-methoxy-3-oxopropyl)-2-methyl-2H-indazole-4-carboxylate

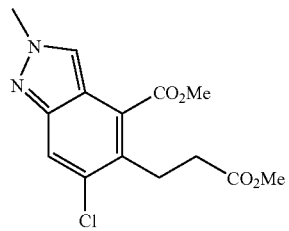

To a solution of methyl 6-chloro-5-[(1E)-3-methoxy-3-oxoprop-1-en-1-yl]-2-methyl-2H-indazole-4-carboxylate (440 mg, 1.43 mmol) in tetrahydrofuran (10 mL) was added 5% platinum-activated carbon (88 mg), and the mixture was stirred under a hydrogen atmosphere at room temperature for 2 days. The catalyst was filtered off, and the filtrate was concentrated under reduced pressure. The residue was purified by silica gel column chromatography (ethyl acetate/hexane=30/70→70/30) to give the title compound (295 mg, yield 66%).

$^1$H-NMR (CDCl$_3$) δ: 2.69 (2H, t, J=7.8 Hz), 3.34 (2H, t, J=7.8 Hz), 3.68 (3H, s), 3.98 (3H, s), 4.26 (3H, s), 7.26 (1H, s), 8.26 (1H, s),

MS (ESI+): 311 (M+H).

Reference Example 60

5-chloro-2-methyl-6,7-dihydrocyclopenta[e]indazol-8(2H)-one

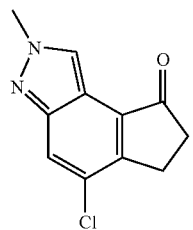

To a solution of methyl 6-chloro-5-(3-methoxy-3-oxopropyl)-2-methyl-2H-indazole-4-carboxylate (295 mg, 0.948 mmol) in tetrahydrofuran (10 mL) was added 28% sodium methoxide methanol solution (390 μL), and the mixture was heated under reflux for 2 hr. The reaction solution was concentrated to dryness to give crystals. The obtained crystals were added to 10% sulfuric acid (10 mL) heated to 100° C., and the mixture was heated under reflux for 4 hr. The reaction solution was neutralized with 8M aqueous sodium hydroxide solution, and the mixture was extracted with ethyl acetate. The extract was washed with saturated brine, and dried over anhydrous sodium sulfate. The solvent was evaporated under reduced pressure to give the title compound (174 mg, yield 83%).

$^1$H-NMR (CDCl$_3$) δ: 2.70-2.80 (2H, m), 3.15-3.23 (2H, m), 4.29 (3H, s), 7.40 (1H, s), 8.39 (1H, s), melting point: 207-209° C. (recrystallized from ethyl acetate),

MS (ESI+): 221 (M+H), elemental analysis: for C$_{11}$H$_9$N$_2$ClO

Calculated (%): C, 59.88; H, 4.11; N, 12.70

Found (%): C, 59.76; H, 4.03; N, 12.69.

Reference Example 61

(5-chloro-2-methyl-6,7-dihydrocyclopenta[e]indazol-8(2H)-ylidene)acetonitrile

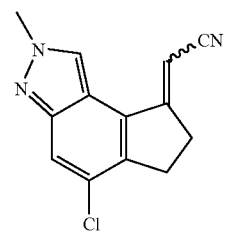

To a suspension of 60% sodium hydride (34.8 mg, 0.870 mmol) in tetrahydrofuran (3 mL) was added diethyl cyanomethylphosphonate (152 μL, 0.94 mmol), and the mixture was stirred at room temperature for 15 min. A suspension of 5-chloro-2-methyl-6,7-dihydrocyclopenta[e]indazol-8(2H)-one (160 mg, 0.725 mmol) in tetrahydrofuran (3 mL) was added thereto, and the mixture was stirred at 50° C. for 4 hr. A solution prepared by adding diethyl cyanomethylphosphonate (152 μL, 0.94 mmol) to a suspension of 60% sodium hydride (34.8 mg, 0.870 mmol) in tetrahydrofuran (3 mL), and stirring the mixture at room temperature for 15 min was added to the reaction solution, and the mixture was further stirred at 50° C. for 4 hr. The reaction solution was diluted with saturated aqueous sodium hydrogen carbonate solution, and the mixture was extracted with ethyl acetate. The extract was washed with water and saturated brine, and dried over anhydrous sodium sulfate. The solvent was evaporated under reduced pressure and the residue was washed with diisopropyl ether to give the title compound (131 mg, yield 74%).

$^1$H-NMR (CDCl$_3$) δ: 3.16-3.22 (4H, m), 4.31 (3H, s), 5.49-5.52 (1H, m), 7.33 (1H, s), 8.05 (1H, s), melting point: 224-226° C. (recrystallized from ethyl acetate),

MS (ESI+): 244 (M+H), elemental analysis: for C$_{13}$H$_{10}$N$_3$Cl

Calculated (%): C, 64.07; H, 4.14; N, 17.24

Found (%): C, 63.98; H, 4.07; N, 17.25.

Reference Example 62

2-(5-chloro-2-methyl-6,7-dihydrocyclopenta[e]indazol-8(2H)-ylidene)ethanamine

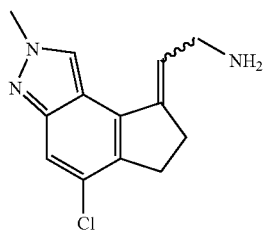

(5-Chloro-2-methyl-6,7-dihydrocyclopenta[e]indazol-8(2H)-ylidene)acetonitrile (116 mg, 2.87 mmol) was dissolved in a mixture of methanol (5 mL) and tetrahydrofuran (5 mL), Raney cobalt (1 g) and 8M ammonia/methanol solution (2 mL) were added to the solution, and the mixture was stirred under a hydrogen atmosphere at room temperature for 4 hr. The catalyst was filtered off through celite, and the filtrate was concentrated under reduced pressure to give the title compound (118 mg, yield 100%).

$^1$H-NMR (CDCl$_3$) δ: 2.80-2.88 (2H, m), 3.52-3.57 (2H, m), 4.28 (3H, s), 5.89-5.98 (1H, m), 7.24 (1H, s), 8.17 (1H, s), MS (ESI+): 248 (M+H).

Reference Example 63 methyl 9-(cyanomethyl)-2-phenyl-8,9-dihydro-7H-cyclopenta[c]pyrazolo[1,5-a]pyridine-1-carboxylate

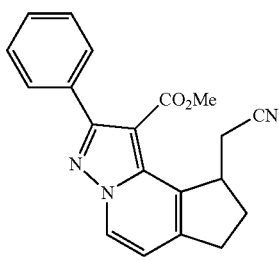

To a solution of 2-[(aminooxy)sulfonyl]-1,3,5-trimethylbenzene (about 16.4 mmol) in acetonitrile (80 mL) was added a solution of 6,7-dihydro-5H-cyclopenta[c]pyridin-7-ylacetonitrile (1.30 g, 8.22 mmol) in acetonitrile (40 mL), and the mixture was stirred at room temperature for 30 min. N,N-Dimethylformamide (40 mL) was added, and the mixture was concentrated under reduced pressure. To 46% of the residual solution were added methyl 3-phenylpropiolate (671 µL, 4.55 mmol) and potassium carbonate (1.31 g, 9.48 mmol), and the mixture was stirred at room temperature for 18 hr. The reaction solution was diluted with water, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane=25/75) to give the title compound (523 mg).

$^1$H-NMR (CDCl$_3$) δ: 2.23-2.33 (1H, m), 2.45-2.69 (2H, m), 2.82-2.91 (1H, m), 2.93-3.05 (1H, m), 3.24-3.39 (1H, m), 3.70 (3H, s), 4.42-4.51 (1H, m), 6.92 (1H, d, J=6.9 Hz), 7.40-7.48 (3H, m), 7.56-7.64 (2H, m), 8.42 (1H, d, J=6.9 Hz), melting point: 214-215° C. (recrystallized from ethyl acetate),
MS (ESI+): 332 (M+H),
elemental analysis: for C$_{20}$H$_{17}$N$_3$O$_2$
Calculated (%): C, 72.49; H, 5.17; N, 12.68
Found (%): C, 72.45; H, 5.13; N, 12.70.

Reference Example 64 methyl 9-(2-aminoethyl)-2-phenyl-8,9-dihydro-7H-cyclopenta[c]pyrazolo[1,5-a]pyridine-1-carboxylate

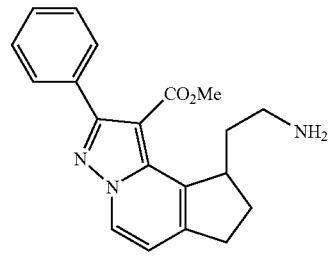

Methyl 9-(cyanomethyl)-2-phenyl-8,9-dihydro-7H-cyclopenta[c]pyrazolo[1,5-a]pyridine-1-carboxylate (300 mg, 0.905 mmol) and Raney cobalt (3 g) were suspended in 2M ammonia/ethanol solution (15 mL), and the suspension was stirred under a hydrogen atmosphere at room temperature for 12 hr. The catalyst was filtered off through celite, and the filtrate was concentrated under reduced pressure to give the title compound (295 mg, yield 97%).

$^1$H-NMR (CDCl$_3$) δ: 1.37-1.53 (1H, m), 1.72-1.86 (1H, m), 2.01-2.13 (1H, m), 2.23-2.40 (1H, m), 2.73-2.98 (3H, m), 3.00-3.14 (1H, m), 3.70 (3H, s), 4.08-4.19 (1H, m), 6.86 (1H, d, J=6.9 Hz), 7.39-7.49 (3H, m), 7.59-7.66 (2H, m), 8.36 (1H, d, J=6.9 Hz), hidden (2H),
MS (ESI+): 336 (M+H).

Reference Example 65

2-(2-phenyl-8,9-dihydro-7H-cyclopenta[c]pyrazolo[1,5-a]pyridin-9-yl)ethanamine

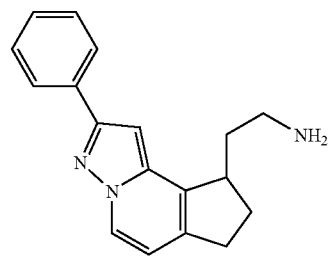

Methyl 9-(2-aminoethyl)-2-phenyl-8,9-dihydro-7H-cyclopenta[c]pyrazolo[1,5-a]pyridine-1-carboxylate (295 mg, 0.881 mmol) was dissolved in 40% (v/v) sulfuric acid (6 mL), and the mixture was stirred at 100° C. for 3 days. The reaction solution was diluted with water and neutralized with sodium hydrogen carbonate, and the mixture was extracted with ethyl acetate. The extract was dried over anhydrous sodium sulfate. The solvent was evaporated under reduced pressure to give the title compound. The obtained title compound was used for the reaction of Example 34 without purification.

$^1$H-NMR (DMSO-d$_6$) δ: 1.46-1.65 (1H, m), 1.79-1.95 (1H, m), 2.06-2.21 (1H, m), 2.24-2.40 (1H, m), 2.61-3.12 (4H, m), 3.44-3.58 (1H, m), 6.82 (1H, d, J=7.0 Hz), 7.02 (1H, s), 7.30-7.53 (3H, m), 7.96-8.05 (2H, m), 8.51 (1H, d, J=7.0 Hz), hidden (2H),

MS (ESI+): 278 (M+H).

Example 1

N-[2-(2-methyl-6,7-dihydrocyclopenta[e]indazol-8 (2H)-ylidene)ethyl]acetamide

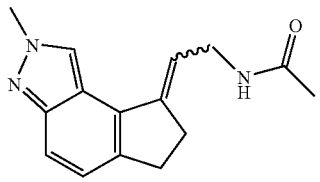

2-(2-Methyl-6,7-dihydrocyclopenta[e]indazol-8(2H)-ylidene)ethanamine (400 mg, 1.88 mmol) was dissolved in tetrahydrofuran (19 mL), triethylamine (287 μL, 2.06 mmol) and acetic anhydride (195 μL, 2.06 mmol) were added under ice-cooling, and the mixture was stirred for 15 min. The reaction solution was diluted with saturated aqueous sodium hydrogen carbonate solution, diluted with ethyl acetate, washed with water and saturated brine, and dried over anhydrous sodium sulfate. The solvent was evaporated under reduced pressure, and the residue was purified by silica gel column chromatography (methanol/ethyl acetate=0/100→10/90) to give the title compound (393 mg, yield 82%).

$^1$H-NMR (CDCl$_3$) δ: 2.03 (3H, s), 2.81-2.93 (2H, m), 3.05-3.13 (2H, m), 4.06-4.15 (2H, m), 4.23 (3H, s), 5.62 (1H, brs), 5.81-5.91 (1H, m), 7.20 (1H, d, J=8.8 Hz), 7.60 (1H, d, J=8.8 Hz), 8.06 (1H, s), melting point: 200-202° C. (recrystallized from ethyl acetate/hexane),

MS (ESI+): 256 (M+H), elemental analysis: for C$_{15}$H$_{17}$N$_3$O

Calculated (%): C, 70.56; H, 6.71; N, 16.46

Found (%): C, 70.20; H, 6.78; N, 16.41.

Example 2

N-[2-(2-methyl-2,6,7,8-tetrahydrocyclopenta[e]indazol-8-yl)ethyl]acetamide

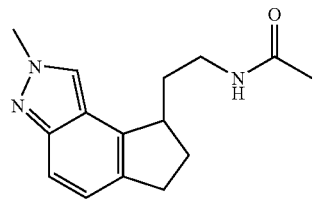

To a solution of N-[2-(2-methyl-6,7-dihydrocyclopenta[e]indazol-8(2H)-ylidene)ethyl]acetamide (311 mg, 1.22 mmol) in methanol (12 mL) was added palladium-carbon powder (31 mg), and the mixture was stirred under a hydrogen atmosphere at room temperature for 3 hr. The catalyst was filtered off, and the filtrate was concentrated under reduced pressure and purified by silica gel column chromatography (methanol/ethyl acetate=0/100→25/75) to give the title compound (229 mg, yield 73%).

$^1$H-NMR (CDCl$_3$) δ: 1.64-1.85 (2H, m), 1.90 (3H, s), 2.16-2.29 (1H, m), 2.32-2.46 (1H, m), 2.82-3.10 (2H, m), 3.24-3.52 (3H, m), 4.20 (3H, s), 5.48 (1H, brs), 7.17 (1H, d, J=8.7 Hz), 7.52 (1H, d, J=8.7 Hz), 7.88 (1H, s), melting point: 123-125° C. (recrystallized from ethyl acetate/hexane),

MS (ESI+): 258 (M+H), elemental analysis: for C$_{15}$H$_{19}$N$_3$O

Calculated (%): C, 70.01; H, 7.44; N, 16.3.3

Found (%): C, 69.73; H, 7.43; N, 16.27.

Example 3

N-{2-[((8S)-2-methyl-2,6,7,8-tetrahydrocyclopenta[e]indazol-8-yl]ethyl}acetamide

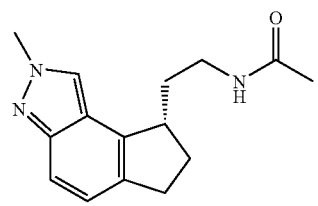

N-[2-(2-Methyl-2,6,7,8-tetrahydrocyclopenta[e]indazol-8-yl)ethyl]acetamide (about 70 mg) was fractionated by high performance liquid chromatography (instrument: Prep LC 2000 (manufactured by Nihon Waters K.K.), column: CHIRALPAK AD (50 mm ID×500 mm L, manufactured by Dicel Chemical Industries, Ltd.), mobile phase: hexane/ethanol=90/10, flow rate: 80 mL/min, column temperature: room temperature, sample concentration: 1.0 mg/mL (hexane/ethanol=90/10), injection amount: about 35 mg). A fraction solution containing an optically active compound having a shorter retention time under the above-mentioned high performance liquid chromatography conditions was concentrated. The concentrate was re-dissolved in ethanol, and re-concentrated to dryness. Hexane was further added, and the mixture was concentrated to dryness again to give the title compound (37 mg, 99% ee). The enantiomer excess (ee) was measured by high performance liquid chromatography (column: CHIRALPAK AD-H (4.6 mm ID×250 mm L, manufactured by Dicel Chemical Industries, Ltd.), mobile phase: hexane/ethanol=90/10, flow rate: 1.0 mL/min, column temperature: room temperature, sample concentration: 1 mg/mL (hexane/ethanol=90/10), injection volume: 10 μL).

$^1$H-NMR (CDCl$_3$) δ: 1.63-1.95 (2H, m), 1.89 (3H, s), 2.14-2.30 (1H, m), 2.32-2.49 (1H, m), 2.82-3.12 (2H, m), 3.26-3.56 (3H, m), 4.20 (3H, s), 5.45 (1H, brs), 7.17 (1H, d, J=8.7 Hz), 7.53 (1H, d, J=8.7 Hz), 7.88 (1H, s),

MS (ESI+): 258 (M+H).

Example 4

N-{2-[(8R)-2-methyl-2,6,7,8-tetrahydrocyclopenta[e]indazol-8-yl]ethyl}acetamide

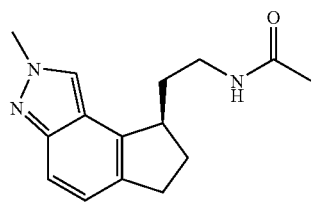

N-[2-(2-Methyl-2,6,7,8-tetrahydrocyclopenta[e]indazol-8-yl)ethyl]acetamide (about 70 mg) was fractionated by high performance liquid chromatography (instrument: Prep LC 2000 (manufactured by Nihon Waters K.K.), column: CHIRALPAK AD (50 mm ID×500 mm L, manufactured by Dicel Chemical Industries, Ltd.), mobile phase: hexane/ethanol=90/10, flow rate: 80 mL/min, column temperature: room temperature, sample concentration: 1.0 mg/mL (hexane/ethanol=90/10), injection amount: about 35 mg). A fraction solution containing an optically active compound having a longer retention time under the above-mentioned high performance liquid chromatography conditions was concentrated. The concentrate was re-dissolved in ethanol, and concentrated to dryness. Hexane was further added, and the mixture was concentrated to dryness again to give the title compound (36 mg, 99% ee). The enantiomer excess (ee) was measured by high performance liquid chromatography (column: CHIRALPAK AD-H (4.6 mm ID×250 mm L, manufactured by Dicel Chemical Industries, Ltd.), mobile phase: hexane/ethanol=90/10, flow rate: 1.0 mL/min, column temperature: room temperature, sample concentration: 1 mg/mL (hexane/ethanol=90/10), injection volume: 10 μL).

$^1$H-NMR (CDCl$_3$) δ: 1.65-1.95 (2H, m), 1.90 (3H, s), 2.15-2.30 (1H, m), 2.32-2.48 (1H, m), 2.82-3.11 (2H, m), 3.23-3.54 (3H, m), 4.20 (3H, s), 5.48 (1H, brs), 7.17 (1H, d, J=8.7 Hz), 7.52 (1H, d, J=8.7 Hz), 7.88 (1H, s),

MS (ESI+): 258 (M+H).

Example 5

N-[2-(2-methyl-6,7-dihydrocyclopenta[e]indazol-8(2H)-ylidene)ethyl]propanamide

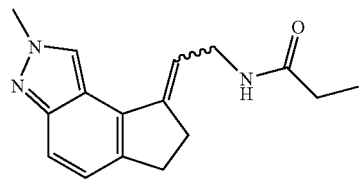

2-(2-Methyl-6,7-dihydrocyclopenta[e]indazol-8(2H)-ylidene)ethanamine (100 mg, 0.469 mmol) was dissolved in tetrahydrofuran (4.7 mL), triethylamine (72.0 μL, 0.516 mmol) and propionic anhydride (66.2 μL, 0.516 mmol) were added under ice-cooling, and the mixture was stirred for 15 min. The reaction solution was diluted with saturated aqueous sodium hydrogen carbonate solution, and the solvent was evaporated under reduced pressure. The residue was purified by silica gel column chromatography (methanol/ethyl acetate=0/100→5/95) to give the title compound (108 mg, yield 85%).

$^1$H-NMR (CDCl$_3$) δ: 1.20 (3H, t, J=7.4 Hz), 2.25 (2H, q, J=7.4 Hz), 2.81-2.94 (2H, m), 3.04-3.15 (2H, m), 4.05-4.16 (2H, m), 4.23 (3H, s), 5.56 (1H, brs), 5.81-5.92 (1H, m), 7.20 (1H, d, J=8.8 Hz), 7.60 (1H, d, J=8.8 Hz), 8.07 (1H, s), melting point: 185-187° C. (recrystallized from ethyl acetate/hexane),

MS (ESI+): 270 (M+H), elemental analysis: for C$_{16}$H$_{19}$N$_3$O

Calculated (%): C, 71.35; H, 7.11; N, 15.60

Found (%): C, 71.29; H, 7.04; N, 15.69.

Example 6

N-[2-(2-methyl-2,6,7,8-tetrahydrocyclopenta[e]indazol-8-yl)ethyl]propanamide

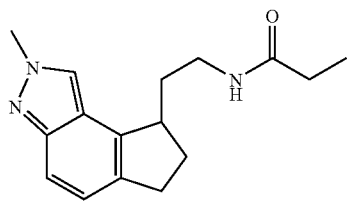

To a solution of N-[2-(2-methyl-6,7-dihydrocyclopenta[e]indazol-8(2H)-ylidene)ethyl]propanamide (83 mg, 0.225 mmol) in methanol (2 mL) was added palladium-carbon powder (8 mg), and the mixture was stirred under a hydrogen atmosphere at room temperature for 3 hr. The catalyst was filtered off, and the filtrate was concentrated under reduced pressure and purified by thin layer chromatography (methanol/ethyl acetate=10/90) to give the title compound (45.1 mg, yield 74%).

$^1$H-NMR (CDCl$_3$) δ: 1.11 (3H, t, J=7.4 Hz), 1.67-1.82 (1H, m), 1.82-1.97 (1H, m), 2.11 (2H, q, J=7.4 Hz), 2.17-2.31 (1H, m), 2.33-2.48 (1H, m), 2.84-3.11 (2H, m), 3.28-3.53 (3H, m), 4.21 (3H, s), 5.38 (1H, brs), 7.17 (1H, d, J=8.8 Hz), 7.52 (1H, d, J=8.8 Hz), 7.88 (1H, s), melting point: 105-107° C. (recrystallized from ethyl acetate/hexane),

MS (ESI+): 272 (M+H), elemental analysis: for C$_{16}$H$_{21}$N$_3$O

Calculated (%): C, 70.82; H, 7.80; N, 15.49

Found (%): C, 70.54; H, 7.78; N, 15.52.

Example 7

N-[2-(1,2-dimethyl-6,7-dihydrocyclopenta[e]indazol-8(2H)-ylidene)ethyl]acetamide

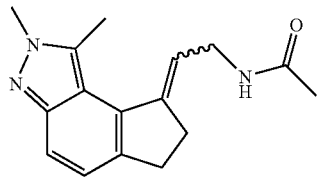

2-(1,2-Dimethyl-6,7-dihydrocyclopenta(e)indazol-8(2H)-ylidene)ethanamine obtained in Reference Example 28 was dissolved in tetrahydrofuran (5 mL), triethylamine (69.8 μL, 0.5 mmol) and acetic anhydride (47.3 μL, 0.5 mmol) were added under ice-cooling, and the mixture was stirred for 15 min. The reaction solution was diluted with saturated aqueous sodium hydrogen carbonate solution, diluted with ethyl acetate, washed with water and saturated brine, and dried over anhydrous sodium sulfate. The solvent was evaporated under reduced pressure, and the residue was purified by silica gel column chromatography (methanol/ethyl acetate=0/100→10/90) to give the title compound (60.3 mg, total yield from Reference Example 25, 20%).

$^1$H-NMR (CDCl$_3$) δ: 2.02 (3H, s), 2.76-2.87 (5H, m), 2.97-3.06 (2H, m), 4.03-4.13 (5H, m), 5.61 (1H, brs), 5.98-6.09 (1H, m), 7.13 (1H, d, J=8.8 Hz), 7.50 (1H, d, J=8.8 Hz), melting point: 200-203° C. (recrystallized from ethyl acetate),

MS (ESI+): 270 (M+H), elemental analysis: for C$_{16}$H$_{19}$N$_3$O.0.1H$_2$O

Calculated (%): C, 70.87; H, 7.13; N, 15.49

Found (%): C, 70.76; H, 7.05; N, 15.43.

Example 8

N-[2-(1,2-dimethyl-2,6,7,8-tetrahydrocyclopenta[e]indazol-8-yl)ethyl]acetamide

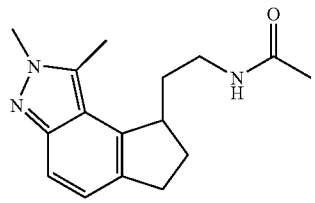

To a solution of N-[2-(1,2-dimethyl-6,7-dihydrocyclopenta[e]indazol-8(2H)-ylidene)ethyl]acetamide (55.7 mg, 0.207 mmol) in methanol (2 mL) was added palladium-carbon powder (10 mg), and the mixture was stirred under a hydrogen atmosphere at room temperature for 7 hr. The catalyst was filtered off, and the filtrate was concentrated under reduced pressure and purified by thin layer chromatography (methanol/ethyl acetate=13/87) to give the title compound (38.2 mg, yield 68%).

$^1$H-NMR (CDCl$_3$) δ: 1.64-1.73 (1H, m), 1.84 (3H, s), 1.86-1.96 (1H, m), 1.98-2.10 (1H, m), 2.25-2.41 (1H, m), 2.68 (3H, s), 2.81-2.93 (1H, m), 2.95-3.08 (1H, m), 3.21-3.33 (1H, m), 3.36-3.51 (1H, m), 3.55-3.65 (1H, m), 4.07 (3H, s), 5.32 (1H, brs), 7.12 (1H, d, J=8.8 Hz), 7.44 (1H, d, J=8.8 Hz), melting point: 146-149° C. (recrystallized from ethyl acetate),

MS (ESI+): 272 (M+H), elemental analysis: for C$_{16}$H$_{21}$N$_3$O

Calculated (%): C, 70.82; H, 7.80; N, 15.49

Found (%): C, 70.49; H, 7.81; N, 15.42.

Example 9

N-[2-(2-methyl-1,6,7,8-tetrahydroindeno[4,5-d]imidazol-8-yl)ethyl]acetamide

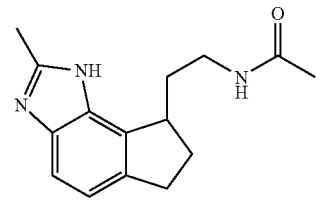

(3-Benzyl-2-methyl-6,7-dihydroindeno[4,5-d]imidazol-8(3H)-ylidene)acetonitrile was dissolved in 2M ammonia/ethanol solution (14 mL), Raney cobalt (10 g) was added, and the mixture was stirred under a hydrogen atmosphere at room temperature for 14 hr. The catalyst was filtered off through celite, and the filtrate was concentrated under reduced pressure. The residue was dissolved in tetrahydrofuran (3 mL), triethylamine (34.9 μL, 0.25 mmol) and acetic anhydride (18.9 μL, 0.20 mmol) were added, and the mixture was stirred at room temperature for 30 min. The reaction solution was concentrated under reduced pressure, and the residue was purified by silica gel column chromatography (methanol/ethyl acetate=5/95→15/85). The purified product was dissolved in methanol (3 mL), palladium-carbon powder (20 mg) was added, and the mixture was stirred under a hydrogen atmosphere at room temperature for 5 hr. The catalyst was filtered off, and the filtrate was concentrated under reduced pressure, and the residue was purified by silica gel column chromatography (methanol/ethyl acetate=5/95→20/80) to give the title compound (13.4 mg, yield 31%).

$^1$H-NMR (CDCl$_3$) δ: 1.74-2.01 (3H, m), 2.09 (3H, s), 2.28-2.46 (1H, m), 2.63 (3H, s), 2.79-2.95 (1H, m), 2.98-3.15 (1H, m), 3.26 (1H, brs), 3.34-3.55 (2H, m), 7.07 (1H, d, J=8.2 Hz), 7.38 (1H, d, J=8.2 Hz), hidden (2H),

MS (ESI+): 258 (M+H).

Example 10

N-[2-(1-methyl-8,9-dihydro-7H-cyclopenta[c]pyrazolo[1,5-a]pyridin-9-yl)ethyl]acetamide

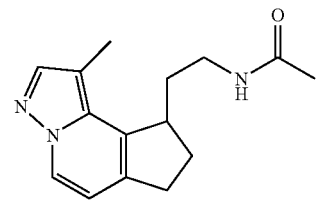

To a solution of ethyl 9-(2-aminoethyl)-8,9-dihydro-7H-cyclopenta[c]pyrazolo[1,5-a]pyridine-1-carboxylate (45.0 mg, 0.165 mmol) in tetrahydrofuran (1.7 mL) was added 1.5M diisobutylaluminum hydride toluene solution (1.3 mL, 1.95 mmol) at room temperature, and the mixture was stirred for 3 hr. Sodium sulfate decahydrate (1.3 g) was added, and the mixture was filtered through celite, and the filtrate was concentrated under reduced pressure. To a mixture of the residue and triethylamine (34.5 μL, 0.248 mmol) in tetrahydrofuran (1.7 mL) was added acetic anhydride (23.4 μL, 0.248 mmol) under ice-cooling, and the mixture was stirred at room temperature for 15 min. Water (50 μL) was added, and the solvent was evaporated under reduced pressure. The residue was purified by silica gel column chromatography (methanol/ethyl acetate=0/100→5/95) and recrystallization (ethyl acetate/diisopropyl ether) to give the title compound (7.3 mg, yield 17%).

$^1$H-NMR (CDCl$_3$) δ: 1.58-1.72 (1H, m), 1.83-1.98 (4H, m), 2.02-2.15 (1H, m), 2.21-2.36 (1H, m), 2.40 (3H, s), 2.73-3.10 (2H, m), 3.28-3.50 (2H, m), 3.51-3.64 (1H, m), 5.39 (1H, brs), 6.57 (1H, d, J=7.1 Hz), 7.69 (1H, s), 8.22 (1H, d, J=7.1 Hz), melting point: 121-122° C. (recrystallized from ethyl acetate/diisopropyl ether),

MS (ESI+): 258 (M+H).

Example 11

N-[2-(8,9-dihydro-7H-cyclopenta[c]pyrazolo[1,5-a] pyridin-9-yl)ethyl]acetamide

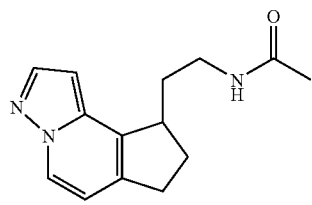

To a mixture of 2-(8,9-dihydro-7H-cyclopenta[c]pyrazolo [1,5-a]pyridin-9-yl)ethanamine hydrochloride (45.5 mg, 0.191 mmol) and triethylamine (206 μL, 1.48 mmol) in tetrahydrofuran (1.5 mL) was added acetic anhydride (42.0 μL, 0.444 mmol) under ice-cooling, and the mixture was stirred at room temperature for 15 min. Water (50 μL) was added, and the solvent was evaporated under reduced pressure. The residue was purified by silica gel column chromatography (methanol/ethyl acetate=0/100→10/90) and recrystallization (ethyl acetate/diisopropyl ether) to give the title compound (22.4 mg, yield 48%).

$^1$H-NMR (CDCl$_3$) δ: 1.66-1.82 (1H, m), 1.92 (3H, s), 1.93-2.04 (1H, m), 2.14-2.27 (1H, m), 2.34-2.50 (1H, m), 2.80-3.10 (2H, m), 3.24-3.54 (3H, m), 5.44 (1H, brs), 6.38 (1H, d, J=2.2 Hz), 6.66 (1H, d, J=7.1 Hz), 7.91 (1H, d, J=2.2 Hz), 8.32 (1H, d, J=7.1 Hz), melting point: 100-101° C. (recrystallized from ethyl acetate/diisopropyl ether),

MS (ESI+): 244 (M+H).

Example 12

N-[2-(8,9-dihydro-7H-cyclopenta[c]pyrazolo[1,5-a] pyridin-9-yl)ethyl]propanamide

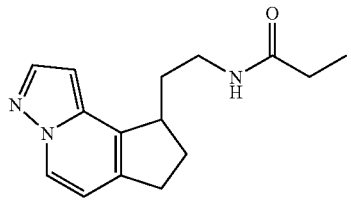

To a mixture of 2-(8,9-dihydro-7H-cyclopenta[c]pyrazolo [1,5-a]pyridin-9-yl)ethanamine hydrochloride (45.5 mg, 0.191 mmol) and triethylamine (206 μL, 1.48 mmol) in tetrahydrofuran (1.5 mL) was added propionic anhydride (56.9 μL, 0.444 mmol) under ice-cooling, and the mixture was stirred at room temperature for 15 min. Water (50 μL) was added, and the solvent was evaporated under reduced pressure. The residue was purified by silica gel column chromatography (ethyl acetate/hexane=50/50→100/0) and recrystallization (ethyl acetate/diisopropyl ether) to give the title compound (23.3 mg, yield 47%).

$^1$H-NMR (CDCl$_3$) δ: 1.12 (3H, t, J=7.6 Hz), 1.67-1.82 (1H, m), 1.92-2.07 (1H, m), 2.08-2.27 (3H, m), 2.34-2.54 (1H, m), 2.82-3.11 (2H, m), 3.27-3.56 (3H, m), 5.42 (1H, brs), 6.38-6.42 (1H, m), 6.68 (1H, d, J=7.0 Hz), 7.93 (1H, d, J=2.3 Hz), 8.34 (1H, d, J=7.0 Hz), melting point: 72-73° C. (recrystallized from ethyl acetate/ diisopropyl ether),

MS (ESI+): 258 (M+H).

Example 13 ethyl 9-[2-(acetylamino)ethyl]-2-methyl-8,9-dihydro-7H-cyclopenta[c]pyrazolo[1,5-a]pyridine-1-carboxylate

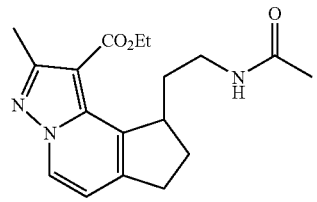

To a mixture of ethyl 9-(2-aminoethyl)-2-methyl-8,9-dihydro-7H-cyclopenta[c]pyrazolo[1,5-a]pyridine-1-carboxylate (50.0 mg, 0.174 mmol) and triethylamine (36.4 μL, 0.261 mmol) in tetrahydrofuran (2 mL) was added acetic anhydride (24.7 μL) under ice-cooling, and the mixture was stirred at room temperature for 30 min. Water (50 μL) was added, and the solvent was evaporated under reduced pressure. The residue was purified by silica gel column chromatography (methanol/ethyl acetate=0/100→5/95) and recrystallization (diisopropyl ether) to give the title compound (32.1 mg, yield 56%).

$^1$H-NMR (CDCl$_3$) δ: 1.38-1.55 (4H, m), 1.77-1.92 (1H, m), 1.96-2.10 (4H, m), 2.14-2.36 (1H, m), 2.63 (3H, s), 2.82-2.93 (1H, m), 2.97-3.13 (1H, m), 3.25-3.36 (1H, m), 3.36-3.50 (1H, m), 4.16-4.26 (1H, m), 4.29-4.41 (2H, m), 6.81 (1H, d, J=6.9 Hz), 7.21 (1H, brs), 8.25 (1H, d, J=6.9 Hz), melting point: 101-103° C. (recrystallized from diisopropyl ether),

MS (ESI+): 330 (M+H).

Example 14

N-[2-(1,2-dimethyl-8,9-dihydro-7H-cyclopenta[c]pyrazolo[1,5-a]pyridin-9-yl)ethyl]acetamide

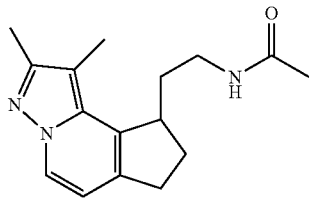

To a solution of ethyl 9-(2-aminoethyl)-2-methyl-8,9-dihydro-7H-cyclopenta[c]pyrazolo[1,5-a]pyridine-1-carboxylate (75.0 mg, 0.261 mmol) in tetrahydrofuran (2.6 mL) was added 1.5M diisobutylaluminum hydride toluene solution (2.1 mL, 3.2 mmol) at room temperature, and the mixture was stirred for 3 hr. Sodium sulfate decahydrate (2.1 g) was added and the mixture was filtered through celite. The filtrate was concentrated under reduced pressure. To a mixture of the residue and triethylamine (54.6 μL, 0.392 mmol) in tetrahydrofuran (2.5 mL) was added acetic anhydride (37.0 μL, 0.391 mmol) under ice-cooling, and the mixture was stirred at room temperature for 30 min. Water (70 μL) was added, and the solvent was evaporated under reduced pressure. The residue was purified by silica gel column chromatography (methanol/ethyl acetate=0/100→10/90) and recrystallization (ethyl acetate/diisopropyl ether) to give the title compound (24.4 mg, yield 34%).

$^1$H-NMR (CDCl$_3$) δ: 1.49-1.68 (1H, m), 1.82-1.97 (4H, m), 2.01-2.14 (1H, m), 2.21-2.34 (4H, m), 2.37 (3H, s), 2.73-2.85 (1H, m), 2.89-3.04 (1H, m), 3.26-3.50 (2H, m), 3.51-3.62 (1H, m), 5.41 (1H, brs), 6.48 (1H, d, J=6.9 Hz), 8.12 (1H, d, J=6.9 Hz), melting point: 134-135° C. (recrystallized from ethyl acetate/diisopropyl ether),

MS (ESI+): 272 (M+H).

Example 15 ethyl 9-{2-[(tert-butoxycarbonyl)amino]ethyl}-2-methyl-8,9-dihydro-7H-cyclopenta[c]pyrazolo[1,5-a]pyridine-1-carboxylate

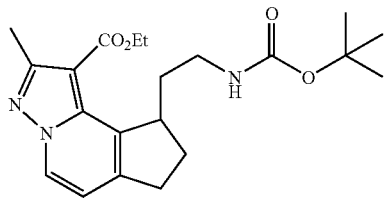

To a solution of ethyl 9-(2-aminoethyl)-2-methyl-8,9-dihydro-7H-cyclopenta[c]pyrazolo[1,5-a]pyridine-1-carboxylate (100 mg, 0.348 mmol) in tetrahydrofuran (3.5 mL) was added di-t-butyl dicarbonate (95.9 μL, 0.417 mmol) under ice-cooling, and the mixture was stirred at room temperature for 30 min. The solvent was evaporated under reduced pressure, and the residue was purified by silica gel column chromatography (ethyl acetate/hexane=0/100→30/70) to give the title compound (135 mg, yield 100%).

$^1$H-NMR (CDCl$_3$) δ: 1.34-1.55 (13H, m), 1.69-1.87 (1H, m), 1.98-2.10 (1H, m), 2.17-2.37 (1H, m), 2.62 (3H, s), 2.80-2.95 (1H, m), 2.96-3.13 (1H, m), 3.20-3.29 (2H, m), 4.16-4.28 (1H, m), 4.37 (2H, q, J=7.1 Hz), 5.71 (1H, brs), 6.78 (1H, d, J=6.9 Hz), 8.24 (1H, d, J=6.9 Hz),

MS (ESI+): 388 (M+H).

Example 16 ethyl (9S)-9-{2-[(tert-butoxycarbonyl)amino]ethyl}-2-methyl-8,9-dihydro-7H-cyclopenta[c]pyrazolo[1,5-a]pyridine-1-carboxylate

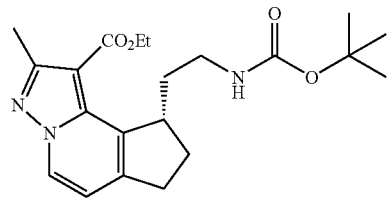

Ethyl 9-{2-[(tert-butoxycarbonyl)amino]ethyl}-2-methyl-8,9-dihydro-7H-cyclopenta[c]pyrazolo[1,5-a]pyridine-1-carboxylate (300 mg) was fractionated by high performance liquid chromatography (instrument: Prep LC 2000 (manufactured by Nihon Waters K.K.), column: CHIRALPAK AD (50 mm ID×500 mm L, manufactured by Dicel Chemical Industries, Ltd.), mobile phase: A) hexane 100%, B) hexane/ethanol=70/30, mixing ratio: A/B=80/20, flow rate: 60 mL/min, column temperature: 30° C., sample concentration: 10 mg/mL (hexane/ethanol=95/5), injection amount: 300 mg). A fraction solution containing an optically active compound having a shorter retention time under the above-mentioned high performance liquid chromatography conditions was concentrated to give the title compound (146 mg, 99.7% ee). The enantiomer excess (ee) was measured by high performance liquid chromatography (column: CHIRALPAK AD (4.6 mm ID×250 mm L, manufactured by Dicel Chemical Industries, Ltd.), mobile phase: hexane/ethanol=95/5, flow rate: 0.5 mL/min, column temperature: 30° C., sample concentration: 0.25 mg/mL (hexane/ethanol=95/5), injection volume: 10 μL).

$^1$H-NMR (CDCl$_3$) δ: 1.36-1.52 (13H, m), 1.70-1.85 (1H, m), 1.97-2.08 (1H, m), 2.16-2.33 (1H, m), 2.61 (3H, s), 2.80-2.92 (1H, m), 2.95-3.09 (1H, m), 3.19-3.39 (2H, m), 4.15-4.26 (1H, m), 4.36 (2H, q, J=7.1 Hz), 5.70 (1H, brs), 6.77 (1H, d, J=6.9 Hz), 8.23 (1H, d, J=6.9 Hz). -

Example 17 ethyl (9R)-9-{2-[(tert-butoxycarbonyl)amino]ethyl}-2-methyl-8,9-dihydro-7H-cyclopenta[c]pyrazolo[1,5-a]pyridine-1-carboxylate

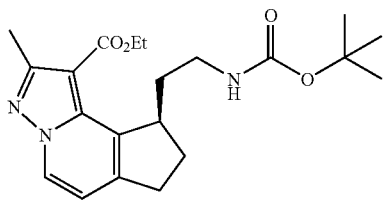

Ethyl 9-{2-[(tert-butoxycarbonyl)amino]ethyl}-2-methyl-8,9-dihydro-7H-cyclopenta[c]pyrazolo[1,5-a]pyridine-1-carboxylate (300 mg) was fractionated by high performance liquid chromatography (instrument: Prep LC 2000 (manufactured by Nihon Waters K.K.), column: CHIRALPAK AD (50 mm ID×500 mm L, manufactured by Dicel Chemical Industries, Ltd.), mobile phase: A) hexane 100%, B) hexane/ethanol=70/30, mixing ratio: A/B=80/20, flow rate: 60 mL/min, column temperature: 30° C., sample concentration: 10 mg/mL (hexane/ethanol=95/5), injection amount: 300 mg). A fraction solution containing an optically active compound having a longer retention time under the above-mentioned high performance liquid chromatography conditions was concentrated to give the title compound (140 mg, 99.7% ee). The enantiomer excess (ee) was measured by high performance liquid chromatography (column: CHIRALPAK AD (4.6 mm ID×250 mm L, manufactured by Dicel Chemical Industries, Ltd.), mobile phase: hexane/ethanol=95/5, flow rate: 0.5 mL/min, column temperature: 30° C., sample concentration: 0.25 mg/mL (hexane/ethanol=95/5), injection volume: 10 μL).

$^1$H-NMR (CDCl$_3$) δ: 1.37-1.55 (13H, m), 1.69-1.87 (1H, m), 2.00-2.10 (1H, m), 2.18-2.34 (1H, m), 2.62 (3H, s), 2.81-2.92 (1H, m), 2.97-3.11 (1H, m), 3.20-3.31 (2H, m), 4.16-4.26 (1H, m), 4.37 (2H, q, J=7.0 Hz), 5.71 (1H, brs), 6.78 (1H, d, J=6.9 Hz), 8.24 (1H, d, J=6.9 Hz).

Example 18

N-[2-(2-methyl-8,9-dihydro-7H-cyclopenta[c]pyrazolo[1,5-a]pyridin-9-yl)ethyl]acetamide

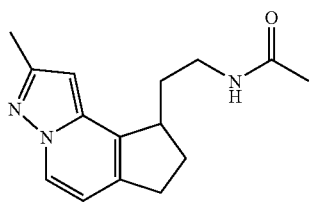

To a mixture of 2-(2-methyl-8,9-dihydro-7H-cyclopenta[c]pyrazolo[1,5-a]pyridin-9-yl)ethanamine hydrochloride obtained in Reference Example 43 and triethylamine (1.36 mL, 9.76 mmol) in tetrahydrofuran (5 mL) was added acetic anhydride (115 μL, 1.22 mmol) under ice-cooling, and the mixture was stirred for 15 min. The reaction solution was diluted with saturated aqueous sodium hydrogen carbonate solution, and the mixture was extracted with ethyl acetate. The extract was dried over anhydrous sodium sulfate, and the solvent was evaporated under reduced pressure. The residue was purified by silica gel column chromatography (ethyl acetate/hexane=50/50→100/0) and recrystallization (ethyl acetate/diisopropyl ether) to give the title compound (56.6 mg, total yield from Reference Example 43, 45%).

$^1$H-NMR (CDCl$_3$) δ: 1.63-1.78 (1H, m), 1.88-2.03 (4H, m), 2.11-2.26 (1H, m), 2.33-2.45 (1H, m), 2.47 (3H, s), 2.78-3.07 (2H, m), 3.24-3.50 (3H, m), 5.43 (1H, brs), 6.15 (1H, s), 6.57 (1H, d, J=7.2 Hz), 8.21 (1H, d, J=7.2 Hz), melting point: 106-107° C. (recrystallized from ethyl acetate/diisopropyl ether),

MS (ESI+): 258 (M+H), elemental analysis: for C$_{15}$H$_{19}$N$_3$O.0.1H$_2$O

Calculated (%): C, 69.52; H, 7.47; N, 16.22

Found (%): C, 69.67; H, 7.43; N, 16.38.

Example 19

N-{2-[(9S)-2-methyl-8,9-dihydro-7H-cyclopenta[c]pyrazolo[1,5-a]pyridin-9-yl]ethyl}acetamide

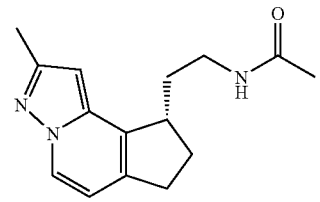

A mixture of ethyl (9S)-9-{2-[(tert-butoxycarbonyl)amino]ethyl}-2-methyl-8,9-dihydro-7H-cyclopenta[c]pyrazolo[1,5-a]pyridine-1-carboxylate (140 mg, 0.361 mmol) in 12M hydrochloric acid (4 mL) was stirred at 100° C. for 3 days, and concentrated under reduced pressure. To a mixture of the residue and triethylamine (503 μL, 3.61 mmol) in tetrahydrofuran (3.6 mL) was added acetic anhydride (102 μL, 1.08 mmol) under ice-cooling, and the mixture was stirred at room temperature for 10 min. Water (50 μL) was added, and the solvent was evaporated under reduced pressure. The residue was purified by silica gel column chromatography (methanol/ethyl acetate=0/100→5/95) to give the title compound (69.7 mg, yield 75%, >99.9% ee). The enantiomer excess (ee) was measured by high performance liquid chromatography (column: CHIRALPAK AD-H mm ID×250 mm L, manufactured by Dicel Chemical Industries, Ltd.), mobile phase: hexane/ethanol=95/5, flow rate: 1.0 mL/min, column temperature: 30° C., sample concentration: 0.5 mg/mL (hexane/ethanol=95/5), injection volume: 10 μL).

$^1$H-NMR (CDCl$_3$) δ: 1.63-1.78 (1H, m), 1.89-2.10 (4H, m), 2.11-2.27 (1H, m), 2.33-2.45 (1H, m), 2.47 (3H, s), 2.79-

3.06 (2H, m), 3.24-3.48 (3H, m), 5.42 (1H, brs), 6.16 (1H, s), 6.58 (1H, d, J=7.0 Hz), 8.21 (1H, d, J=7.0 Hz).

Example 20

N-{2-[(9R)-2-methyl-8,9-dihydro-7H-cyclopenta[c]pyrazolo[1,5-a]pyridin-9-yl]ethyl}acetamide

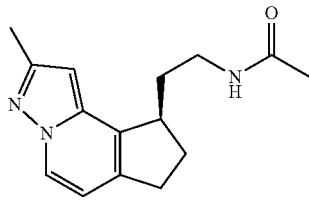

A mixture of ethyl (9R)-9-{2-[(tert-butoxycarbonyl)amino]ethyl}-2-methyl-8,9-dihydro-7H-cyclopenta[c]pyrazolo[1,5-a]pyridine-1-carboxylate (135 mg, 0.348 mmol) in 12M hydrochloric acid (4 mL) was stirred at 100° C. for 3 days, and concentrated under reduced pressure. To a mixture of the residue and triethylamine (485 μL, 3.48 mmol) in tetrahydrofuran (3.5 mL) was added acetic anhydride (98.7 μL, 1.04 mmol) under ice-cooling, and the mixture was stirred at room temperature for 10 min. Water (50 μL) was added, and the solvent was evaporated under reduced pressure. The residue was purified by silica gel column chromatography (methanol/ethyl acetate=0/100→5/95) to give the title compound (86.0 mg, yield 96%, 99.9% ee). The enantiomer excess (ee) was measured by high performance liquid chromatography (column: CHIRALPAK AD-H mm ID×250 mm L, manufactured by Dicel Chemical Industries, Ltd.), mobile phase: hexane/ethanol=95/5, flow rate: 1.0 mL/min, column temperature: 30° C., sample concentration: 0.5 mg/mL (hexane/ethanol=95/5), injection volume: 10 μL).

$^1$H-NMR (CDCl$_3$) δ: 1.64-1.77 (1H, m), 1.89-2.10 (4H, m), 2.12-2.25 (1H, m), 2.33-2.45 (1H, m), 2.47 (3H, s), 2.80-3.05 (2H, m), 3.25-3.47 (3H, m), 5.43 (1H, brs), 6.15 (1H, s), 6.58 (1H, d, J=7.0 Hz), 8.21 (1H, d, J=7.0 Hz).

Example 21

N-[2-(2-ethyl-8,9-dihydro-7H-cyclopenta[c]pyrazolo[1,5-a]pyridin-9-yl)ethyl]acetamide

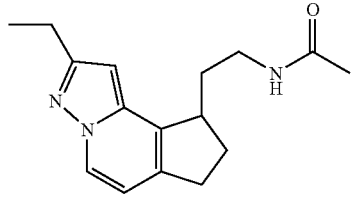

A mixture of ethyl 9-(2-aminoethyl)-2-ethyl-8,9-dihydro-7H-cyclopenta[c]pyrazolo[1,5-a]pyridine-1-carboxylate (81.0 mg, 0.269 mmol) in 12M hydrochloric acid (3 mL) was stirred at 100° C. for 3 days, and the mixture was concentrated under reduced pressure. To a mixture of the residue and triethylamine (375 μL, 2.69 mmol) in tetrahydrofuran (2.7 mL) was added acetic anhydride (76.3 μL, 0.807 mmol) under ice-cooling, and the mixture was stirred at room temperature for 15 min. Water (50 μL) was added, and the solvent was evaporated under reduced pressure. The residue was purified by silica gel column chromatography (methanol/ethyl acetate=0/100→5/95) to give the title compound (62.9 mg, yield 85%).

$^1$H-NMR (CDCl$_3$) δ: 1.35 (3H, t, J=7.6 Hz), 1.62-1.77 (1H, m), 1.86-2.02 (4H, m), 2.13-2.26 (1H, m), 2.30-2.48 (1H, m), 2.76-3.05 (4H, m), 3.23-3.48 (3H, m), 5.52 (1H, brs), 6.58 (1H, d, J=6.8 Hz), 8.22 (1H, d, J=6.8 Hz).

Example 22

N-[2-(2-methyl-7,8-dihydro-6H-cyclopenta[e]imidazo[1,2-a]pyridin-8-yl)ethyl]acetamide

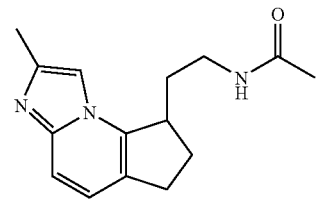

A suspension of N-[2-(2-amino-6,7-dihydro-5H-cyclopenta[b]pyridin-7-yl)ethyl]acetamide (17.6 mg, 0.0803 mmol), bromoacetone (16.5 mg, 0.120 mmol) and sodium hydrogen carbonate (10.1 mg, 0.12 mmol) in ethanol (1 mL) was heated under reflux for 4 hr. The solvent was evaporated under reduced pressure, and N,N-dimethylformamide (1 mL) was added. The mixture was irradiated with 150 W microwave and stirred at 160° C. for 30 min. The solvent was evaporated under reduced pressure, and the residue was purified by thin layer chromatography (methanol/ethyl acetate=17/83 and NH; methanol/ethyl acetate=5/95) to give the title compound (2.0 mg, yield 10%).

$^1$H-NMR (CDCl$_3$) δ: 1.67-1.81 (1H, m), 1.89 (3H, s), 2.04-2.19 (2H, m), 2.37-2.54 (1H, m), 2.47 (3H, s), 2.81-2.97 (1H, m), 2.97-3.12 (1H, m), 3.20-3.35 (1H, m), 3.35-3.51 (2H, m), 5.42 (1H, brs), 7.08 (1H, d, J=8.8 Hz), 7.19 (1H, s), 7.39 (1H, d, J=8.8 Hz).

MS (ESI+): 258 (M+H).

Example 23

N-{2-[(8S)-1-fluoro-2-methyl-2,6,7,8-tetrahydrocyclopenta[e]indazol-8-yl]ethyl}acetamide

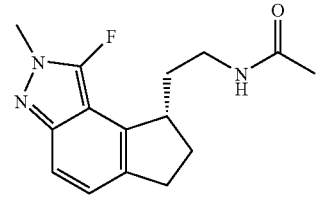

To a solution of N-{2-[(8S)-2-methyl-2,6,7,8-tetrahydrocyclopenta[e]indazol-8-yl]ethyl}acetamide (1.01 g, 3.91 mmol) in acetonitrile (39.2 mL) was added xenon difluoride (728 mg, 4.30 mmol) under ice-cooling, and the mixture was stirred for 18 hr. The reaction solution was diluted with ethyl acetate, washed with saturated aqueous sodium hydrogen carbonate solution and saturated brine, and dried over anhydrous sodium sulfate. The solvent was evaporated under reduced pressure, and the residue was purified by silica gel column chromatography (NH, ethyl acetate/hexane=50/50→100/0) and preparative TLC (methanol/ethyl acetate=10/90) to give the title compound (86.4 mg, yield 8.0%).

¹H-NMR (CDCl₃) δ: 1.65-1.80 (1H, m), 1.88-2.00 (1H, m), 1.93 (3H, s), 2.05-2.19 (1H, m), 2.31-2.47 (1H, m), 2.79-3.07 (2H, m), 3.25-3.57 (3H, m), 4.03 (3H, d, J=1.6 Hz), 5.38 (1H, brs), 7.12 (1H, d, J=8.8 Hz), 7.30 (1H, dd, J=8.8, 2.2 Hz), melting point: 155-156° C. (recrystallized from ethyl acetate/hexane),

MS (ESI+): 276 (M+H), elemental analysis: for $C_{15}H_{18}N_3FO\cdot0.1H_2O$

Calculated (%): C, 65.01; H, 6.61; N, 15.16

Found (%): C, 64.96; H, 6.48; N, 15.22.

Example 24

N-{2-[(8S)-1-chloro-2-methyl-2,6,7,8-tetrahydrocyclopenta[e]indazol-8-yl]ethyl}acetamide

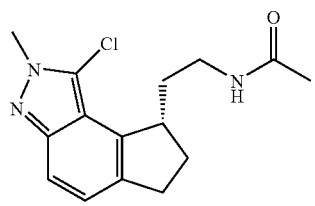

To a solution of N-{2-[(8S)-2-methyl-2,6,7,8-tetrahydrocyclopenta[e]indazol-8-yl]ethyl}acetamide (80 mg, 0.311 mmol) in acetonitrile (3.1 mL) was added N-chlorosuccinimide (45.7 mg, 0.342 mmol), and the mixture was stirred at 50° C. for 5 hr. The solvent was evaporated under reduced pressure, and the residue was purified by silica gel column chromatography (methanol/ethyl acetate=0/100→10/90), preparative HPLC (acetonitrile/water=10/90→90/10) and recrystallization (ethyl acetate/hexane) to give the title compound (20.1 mg, yield 22%).

¹H-NMR (CDCl₃) δ: 1.63-1.77 (1H, m), 1.91 (3H, s), 1.95-2.13 (2H, m), 2.25-2.40 (1H, m), 2.81-2.93 (1H, m), 2.96-3.10 (1H, m), 3.27-3.48 (2H, m), 3.61-3.72 (1H, m), 4.13 (3H, s), 5.35 (1H, brs), 7.17 (1H, d, J=8.8 Hz), 7.45 (1H, d, J=8.8 Hz), melting point: 168-171° C. (recrystallized from ethyl acetate/hexane),

MS (ESI+): 291 (M+H), elemental analysis: for $C_{15}H_{18}N_3ClO$

Calculated (%): C, 61.75; H, 6.22; N, 14.40

Found (%): C, 61.59; H, 6.28; N, 14.40.

Example 25

N-{2-[(8S)-1-bromo-2-methyl-2,6,7,8-tetrahydrocyclopenta[e]indazol-8-yl]ethyl}acetamide

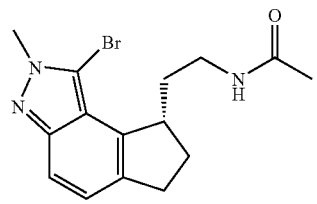

To a solution of N-{2-[(8S)-2-methyl-2,6,7,8-tetrahydrocyclopenta[e]indazol-8-yl]ethyl}acetamide (50 mg, 0.194 mmol) in acetonitrile (2.0 mL) was added N-bromosuccinimide (34.6 mg, 0.194 mmol), and the mixture was stirred at room temperature for 15 min. The solvent was evaporated under reduced pressure, and the residue was purified by silica gel column chromatography (methanol/ethyl acetate=0/100→5/95) to give the title compound (60.3 mg, yield 92%).

¹H-NMR (CDCl₃) δ: 1.57-1.72 (1H, m), 1.91 (3H, s), 1.93-2.13 (2H, m), 2.23-2.41 (1H, m), 2.76-2.93 (1H, m), 2.95-3.10 (1H, m), 3.25-3.52 (2H, m), 3.61-3.78 (1H, m), 4.16 (3H, s), 5.44 (1H, brs), 7.16 (1H, d, J=8.8 Hz), 7.48 (1H, d, J=8.8 Hz), melting point: 167-169° C. (recrystallized from methanol/ethyl acetate),

MS (ESI+): 236 (M+H), elemental analysis: for $Cl_5HlBN_3BrO$

Calculated (%): C, 53.58; H, 5.40; N, 12.50

Found (%): C, 53.40; H, 5.28; N, 12.46.

Example 26

N-[2-(5-fluoro-2-methyl-6,7-dihydrocyclopenta[e]indazol-8(2H)-ylidene)ethyl]acetamide

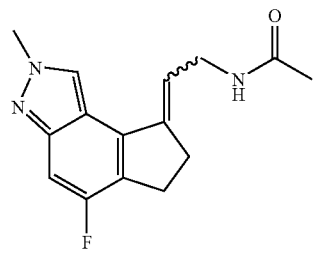

2-(5-Fluoro-2-methyl-6,7-dihydrocyclopenta[e]indazol-8 (2H)-ylidene)ethanamine (78.0 mg, 0.337 mmol) was dissolved in tetrahydrofuran (3.4 mL), triethylamine (56.4 μL, 0.404 mmol) and acetic anhydride (35.0 μL, 0.371 mmol) were added under ice-cooling, and the mixture was stirred for 15 min. The reaction solution was diluted with saturated aqueous sodium hydrogen carbonate solution, diluted with ethyl acetate, washed with water and saturated brine, and dried over anhydrous sodium sulfate. The solvent was evaporated under reduced pressure. The obtained crystals were washed with diisopropyl ether to give the title compound (82.0 mg, yield 89%).

¹H-NMR (CDCl₃) δ: 2.03 (3H, s), 2.85-2.95 (2H, m), 3.08 (2H, s), 4.04-4.13 (2H, m), 4.20 (3H, s), 5.62 (1H, brs), 5.85-5.95 (1H, m), 7.19 (1H, d, J=9.9 Hz), 8.05 (1H, s),
MS (ESI+): 274 (M+H).

Example 27

N-[2-(5-fluoro-2-methyl-6,7-dihydrocyclopenta[e]indazol-8(2H)-ylidene)ethyl]propanamide

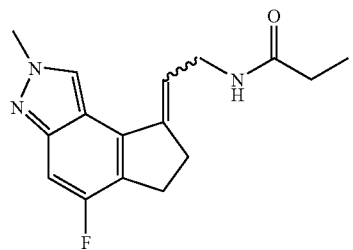

2-(5-Fluoro-2-methyl-6,7-dihydrocyclopenta[e]indazol-8(2H)-ylidene)ethanamine (78.0 mg, 0.337 mmol) was dissolved in tetrahydrofuran (3.4 mL), triethylamine (56.4 μL, 0.404 mmol) and propionic anhydride (47.6 μL, 0.371 mmol) were added under ice-cooling, and the mixture was stirred for 15 min. The reaction solution was diluted with saturated aqueous sodium hydrogen carbonate solution, and the solvent was evaporated under reduced pressure. The residue was purified by silica gel column chromatography (methanol/ethyl acetate=3/97→15/85) to give the title compound (83.2 mg, yield 86%).

¹H-NMR (CDCl₃) δ: 1.20 (3H, t, J=7.5 Hz), 2.26 (2H, q, J=7.5 Hz), 2.88-2.95 (2H, m), 3.06-3.15 (2H, m), 4.06-4.15 (2H, m), 4.21 (3H, s), 5.57 (1H, brs), 5.87-5.96 (1H, m), 7.20 (1H, d, J=9.3. Hz), 8.06 (1H, s),
MS (ESI+): 288 (M+H).

Example 28

N-[2-(5-fluoro-2-methyl-2,6,7,8-tetrahydrocyclopenta[e]indazol-8-yl)ethyl]acetamide

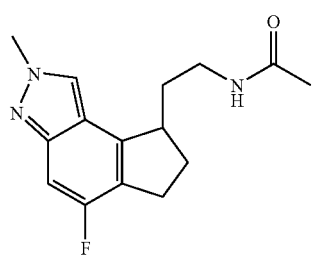

To a solution of N-[2-(5-fluoro-2-methyl-6,7-dihydrocyclopenta[e]indazol-8(2H)-ylidene)ethyl]acetamide (82.0 mg, 0.300 mmol) in methanol (3 mL) was added palladium-carbon powder (8.2 mg), and the mixture was stirred under a hydrogen atmosphere at room temperature for 32 hr. The catalyst was filtered off, and the filtrate was concentrated under reduced pressure. The residue was purified by silica gel column chromatography (NH, methanol/ethyl acetate=0/100→5/95) to give the title compound (63.9 mg, yield 77%).

¹H-NMR (CDCl₃) δ: 1.67-1.81 (1H, m), 1.85-1.97 (1H, m), 1.93 (3H, s), 2.14-2.30 (1H, m), 2.35-2.52 (1H, m), 2.87-3.12 (2H, m), 3.27-3.53 (3H, m), 4.18 (3H, s), 5.45 (1H, brs), 7.12 (1H, d, J=10.2 Hz), 7.89 (1H, s),
melting point: 116-119° C. (recrystallized from ethyl acetate/hexane),
MS (ESI+): 276 (M+H),
elemental analysis: for C₁₅H₁₈N₃FO.0.2H₂O
Calculated (%): C, 64.59; H, 6.64; N, 15.06
Found (%): C, 64.48; H, 6.83; N, 15.09.

Example 29

N-[2-(5-fluoro-2-methyl-2,6,7,8-tetrahydrocyclopenta[e]indazol-8-yl)ethyl]propanamide

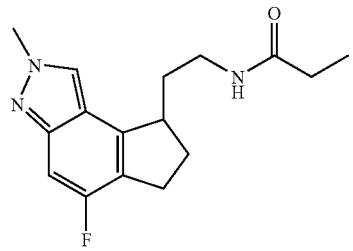

To a solution of N-[2-(5-fluoro-2-methyl-6,7-dihydrocyclopenta[e]indazol-8(2H)-ylidene)ethyl]propanamide (83.2 mg, 0.290 mmol) in methanol (2.9 mL) was added palladium-carbon powder (8.3 mg), and the mixture was stirred under a hydrogen atmosphere at room temperature for 7 hr. The catalyst was filtered off, and the filtrate was concentrated under reduced pressure. The residue was purified by silica gel column chromatography (methanol/ethyl acetate=0/100→15/85) to give the title compound (77.2 mg, yield 92%).

¹H-NMR (CDCl₃) δ: 1.12 (3H, t, J=7.6 Hz), 1.65-1.78 (1H, m), 1.85-1.99 (1H, m), 2.07-2.28 (3H, m), 2.35-2.51 (1H, m), 2.86-3.11 (2H, m), 3.25-3.53 (3H, m), 4.17 (3H, s), 5.45 (1H, brs), 7.11 (1H, d, J=10.2 Hz), 7.88 (1H, s),
melting point: 117-119° C. (recrystallized from ethyl acetate),
MS (ESI+): 290 (M+H),
elemental analysis: for C₁₆H₂₀N₃FO
Calculated (%): C, 66.42; H, 6.97; N, 14.52
Found (%): C, 66.22; H, 7.05; N, 14.42.

Example 30

N-[2-(5-chloro-2-methyl-6,7-dihydrocyclopenta[e]indazol-8(2H)-ylidene)ethyl]acetamide

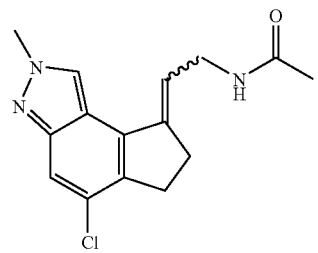

2-(5-Chloro-2-methyl-6,7-dihydrocyclopenta[e]indazol-8 (2H)-ylidene)ethanamine (105 mg, 0.424 mmol) was dissolved in tetrahydrofuran (4 mL), triethylamine (88.6 µL, 0.636 mmol) and acetic anhydride (48.1 µL, 0.509 mmol) were added under ice-cooling, and the mixture was stirred for 10 min. The reaction solution was diluted with saturated aqueous sodium hydrogen carbonate solution, and the mixture was extracted with ethyl acetate. The extract was washed with saturated brine and dried over anhydrous sodium sulfate, and the solvent was evaporated under reduced pressure. The residue was purified by silica gel column chromatography (methanol/ethyl acetate=0/100→5/95) to give the title compound (96.7 mg, yield 79%).

$^1$H-NMR (CDCl$_3$) δ: 2.03 (3H, s), 2.83-2.91 (2H, m), 3.03-3.11 (2H, m), 4.04-4.11 (2H, m), 4.27 (3H, s), 5.62 (1H, brs), 5.80-5.88 (1H, m), 7.24 (1H, s), 8.11 (1H, s), melting point: 177-178° C. (recrystallized from ethyl acetate/hexane),

MS (ESI+): 290 (M+H), elemental analysis: for C$_{15}$H$_{16}$N$_3$ClO

Calculated (%): C, 62.18; H, 5.57; N, 14.50

Found (%): C, 62.11; H, 5.57; N, 14.37.

Example 31

N-[2-(5-chloro-2-methyl-2,6,7,8-tetrahydrocyclopenta[e]indazol-8-yl)ethyl]acetamide

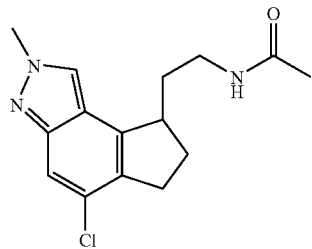

To a solution of N-[2-(5-chloro-2-methyl-6,7-dihydrocyclopenta[e]indazol-8(2H)-ylidene)ethyl]acetamide (79.5 mg, 0.274 mmol) in tetrahydrofuran (5 mL) was added 5% platinum-activated carbon (32 mg), and the mixture was stirred under a hydrogen atmosphere at room temperature for 7 hr. The catalyst was filtered off, and the filtrate was concentrated under reduced pressure. The residue was purified by silica gel column chromatography (methanol/ethyl acetate=0/100→25/75), liquid chromatography (water/acetonitrile=90/10→0/100) and recrystallization (ethyl acetate/hexane) to give the title compound (23.3 mg, yield 29%).

$^1$H-NMR (CDCl$_3$) δ: 1.63-1.77 (1H, m), 1.81-1.92 (1H, m), 1.93 (3H, s), 2.14-2.28 (1H, m), 2.32-2.47 (1H, m), 2.83-3.07 (2H, m), 3.26-3.48 (3H, m), 4.25 (3H, s), 5.45 (1H, brs), 7.20 (1H, s), 7.95 (1H, s), melting point: 143-144° C. (recrystallized from ethyl acetate/hexane),

MS (ESI+): 292 (M+H), elemental analysis: for C$_{15}$H$_{18}$N$_3$ClO

Calculated (%): C, 61.75; H, 6.22; N, 14.40

Found (%): C, 61.75; H, 6.19; N, 14.56.

Example 32

N-[2-(2-methyl-8,9-dihydro-7H-cyclopenta[c]pyrazolo[1,5-a]pyridin-9-yl)ethyl]propanamide

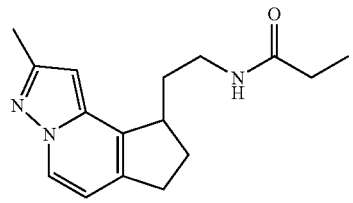

To a mixture of 2-(2-methyl-8,9-dihydro-7H-cyclopenta[c]pyrazolo[1,5-a]pyridin-9-yl)ethanamine (69.7 mg, 0.324 mmol) and triethylamine (90.3 µL, 0.648 mmol) in tetrahydrofuran (3 mL) was added propionic anhydride (49.9 µL, 0.389 mmol) under ice-cooling, and the mixture was stirred for 15 min. The reaction solution was diluted with saturated aqueous sodium hydrogen carbonate solution, and the solvent was evaporated under reduced pressure. The residue was purified by silica gel column chromatography (ethyl acetate) to give the title compound (66.8 mg, yield 76%).

$^1$H-NMR (CDCl$_3$) δ: 1.10 (3H, t, J=7.6 Hz), 1.62-1.77 (1H, m), 1.88-2.02 (1H, m), 2.07-2.25 (3H, m), 2.32-2.44 (1H, m), 2.46 (3H, s), 2.78-3.05 (2H, m), 3.22-3.48 (3H, m), 5.38 (1H, brs), 6.14 (1H, s), 6.57 (1H, d, J=7.0 Hz), 8.20 (1H, d, J=7.0 Hz), melting point: 100-102° C. (recrystallized from ethyl acetate/hexane),

MS (ESI+): 272 (M+H), elemental analysis: for C$_{16}$H$_{21}$N$_3$O

Calculated (%): C, 70.82; H, 7.80; N, 15.49

Found (%): C, 70.99; H, 7.90; N, 15.61.

Example 33

N-[2-(2-methyl-8,9-dihydro-7H-cyclopenta[c]pyrazolo[1,5-a]pyridin-9-yl)ethyl]cyclopropanecarboxamide

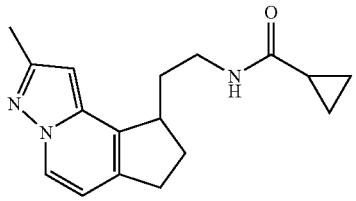

To a mixture of 2-(2-methyl-8,9-dihydro-7H-cyclopenta[c]pyrazolo[1,5-a]pyridin-9-yl)ethanamine (69.7 mg, 0.324 mmol) and triethylamine (90.3 µL, 0.648 mmol) in tetrahydrofuran (3 mL) was added cyclopropanecarbonyl chloride (35.3 µL, 0.389 mmol) under ice-cooling, and the mixture was stirred for 15 min. The reaction solution was diluted with saturated aqueous sodium hydrogen carbonate solution, and the solvent was evaporated under reduced pressure. The residue was purified by silica gel column chromatography (ethyl acetate) to give the title compound (68.0 mg, yield 74%).

[$^1$H-NMR (CDCl$_3$) δ: 0.66-0.76 (2H, m), 0.89-0.99 (2H, m), 1.17-1.30 (1H, m), 2.33-2.45 (1H, m), 2.47 (3H, s), 2.79-3.08 (2H, m), 3.27-3.51 (3H, m), 5.59 (1H, brs), 6.16 (1H, s), 6.58 (1H, d, J=7.0 Hz), 8.21 (1H, d, J=7.0 Hz),
melting point: 112-113° C. (recrystallized from ethyl acetate/hexane),
MS (ESI+): 284 (M+H),
elemental analysis: for C$_{17}$H$_{21}$N$_3$O
Calculated (%): C, 72.06; H, 7.47; N, 14.83
Found (%): C, 71.98; H, 7.63; N, 14.87.

Example 34

N-[2-(2-phenyl-8,9-dihydro-7H-cyclopenta[c]pyrazolo[1,5-a]pyridin-9-yl)ethyl]acetamide

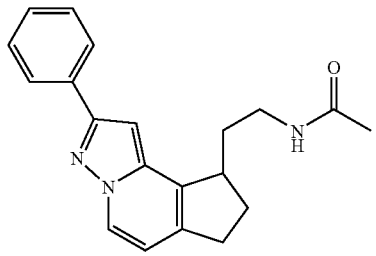

2-(2-Phenyl-8,9-dihydro-7H-cyclopenta[c]pyrazolo[1,5-a]pyridin-9-yl)ethanamine (200 mg, 0.721 mmol) was dissolved in tetrahydrofuran (7 mL), triethylamine (201 μL, 1.44 mmol) and acetic anhydride (81.8 μL, 0.865 mmol) were added under ice-cooling, and the mixture was stirred for 15 min. Saturated aqueous sodium hydrogen carbonate solution was added to the reaction solution, and the solvent was evaporated under reduced pressure. The residue was purified by silica gel column chromatography (ethyl acetate) to give the title compound (195 mg, total yield from Reference Example 65, 69%).
$^1$H-NMR (CDCl$_3$) δ: 1.69-1.85 (1H, m), 1.95 (3H, s), 1.95-2.06 (1H, m), 2.20-2.34 (1H, m), 2.37-2.52 (1H, m), 2.83-3.09 (2H, m), 3.29-3.56 (3H, m), 5.49 (1H, brs), 6.64-6.70 (2H, m), 7.33-7.50 (3H, m), 7.94-8.01 (2H, m), 8.34 (1H, d, J=7.0 Hz),
melting point: 159-160° C. (recrystallized from ethyl acetate),
MS (ESI+): 320 (M+H),
elemental analysis: for C$_{20}$H$_{21}$N$_3$O
Calculated (%): C, 75.21; H, 6.63; N, 13.16
Found (%): C, 75.17; H, 6.63; N, 13.21.

Formulation Example 1

| | |
|---|---|
| (1) Compound obtained in Example 1 | 10.0 g |
| (2) Lactose | 60.0 g |
| (3) Cornstarch | 35.0 g |
| (4) Gelatin | 3.0 g |
| (5) Magnesium stearate | 2.0 g |

A mixture of the compound (10.0 g) obtained in Example 1, lactose (60.0 g) and cornstarch (35.0 g) is granulated using 10 wt % aqueous gelatin solution (30 mL) (3.0 g as gelatin) by passing a 1 mm mesh sieve, dried at 40° C. and sieved again. The obtained granules are mixed with magnesium stearate (2.0 g) and the mixture is compressed. The obtained core tablets are coated with a sugar coating using an aqueous suspension of saccharose, titanium dioxide, talc and gum arabic. The coated tablets are glazed with beeswax to give 1000 coated tablets.

Formulation Example 2

| | |
|---|---|
| (1) Compound obtained in Example 1 | 10.0 g |
| (2) Lactose | 70.0 g |
| (3) Cornstarch | 50.0 g |
| (4) Soluble starch | 7.0 g |
| (5) Magnesium stearate | 3.0 g |

The compound (10.0 g) obtained in Example 1 and magnesium stearate (3.0 g) are granulated using aqueous soluble starch solution (70 mL) (7.0 g as soluble starch), dried and mixed with lactose (70.0 g) and cornstarch (50.0 g). The mixture is compressed to give 1000 tablets.

Experimental Example 1

Melatonin receptor binding inhibitory test
(1) Preparation of CHO-hMelR7 Cells Expressing Human Melatonin 1 Receptors
A cDNA fragment (SEQ ID NO: 1) encoding full-length of human melatonin 1 receptors (human MT$_1$ receptors) was incorporated into expression vector pAKKO-111H (former name pAKKO1.11H; Biochim Biophys Acta. Vol. 1219(2), pp. 251-259, 1994) to give plasmid pAKKO-hMelR7 for animal cell expression. CHO/dhfr-cells (ATCC, #CRL-9096) were plated at a concentration of 0.3×10$^6$ cells/dish in a 6 cm culture dish (Becton Dickinson), and cultured under the conditions of 37° C., 5% CO$_2$ for 48 hr. The cells were transfected with pAKKO-hMelR7 plasmid DNA (5 μg) using Cellphect Transfection Kit (Amersham, #27-9268-01). The transfected cells were cultured in Dulbecco's modified Eagle medium (DMEM) (Sigma, #D6046) containing 10% dialyzed FBS (Biowest, #S180D), 1× Non-Essential Amino Acid (Invitrogen, #11140-050) and 50 μg/mL Gentamycin (Invitrogen, #15750-060), and the cell line that stably expressed the plasmid gene was selected. By a receptor binding assay using 2-[$^{125}$I] Iodomelatonin, CHO-hMelR7 cell line showing specific binding of 2-[$^{125}$I] Iodomelatonin was selected from the obtained clones.
(2) Preparation of CHO-hMT2 Cells Expressing Human Melatonin 2 Receptors
A cDNA fragment (SEQ ID NO: 2) encoding full-length of human melatonin 2 receptors (human MT$_2$ receptors) was incorporated into expression vector pCMV-Script (Stratagene, #212220) to give the plasmid that was pCMV-human MT2 receptors expression vector for animal cell expression. CHO-K1 cells (ATCC, #CCL-61) were plated at the concentration of 1.5×10$^5$ cells/cm$^2$ in a 6 well plate (ASAHI TECHNO GLASS), and cultured under the conditions of 37° C., 5% CO$_2$ for 24 hr. For gene transfection, solution obtained by blending pCMV-human MT2 receptors expression vector (1.9 μg), Lipofectamine Transfection Reagent (Invitrogen, #18324-012) (11.3 μL) and Minimum Essential Medium Eagle (MEM) medium (Sigma, M8042) (93.8 μL), and reacting at room temperature for 20 min was added to the cells per one well. The transfected cells were cultured in MEM medium containing 10% FBS (Life Technology) and 300 μg/mL Geneticin (GIBCO, #10131), and the cell line that stably expressed the plasmid gene was selected. By a receptor binding assay using 2-[$^{125}$I] Iodomelatonin, CHO-hMT2 cell line showing specific binding of 2-[$^{125}$I] Iodomelatonin was selected from the obtained clones.

(3) Preparation of Cellular Membrane Fraction of CHO Cell (CHO-hMelR7 and CHO-hMT2) Stably Expressing Human $MT_1$ and $MT_2$ Receptors CHO-hMelR7 and CHO-hMT2 cells were plated using Cellfactory (Nunc, #170009) under the conditions of $1\times10^8$ cells/2000 mL/flask. The cells were grown to confluent, and recovered by the following method. As the medium for CHO-hMelR7 and CHO-hMT2, MEM α containing 10% FBS and penicillin/streptomycin was used. 300 ng/mL of geneticin was added to the medium for CHO-hMT2.

The medium was discarded, cells were washed twice with 200 mL of EDTA/PBS(−), 200 mL of EDTA/PBS(−) was further added, and the cells were stood still at room temperature for 20 min until they were released. The cells were recovered in four 50 mL tubes (Becton Dickinson, #352070), and centrifuged at 1,500 rpm for 10 min at 4° C. using a low speed cooling centrifuge (Hitachi, CF$_7$D2). The supernatant was discarded, the pellets in the four tubes were suspended in 10 mL of PBS(−), and combined in one tube (Becton Dickinson, #352070). The mixture was further centrifuged at 1,500 rpm for 10 min at 4° C., and the obtained pellets were suspended in 20 mL of ice-cooled homogenizing buffer [10 mM NaHCO$_3$, 5 mM EDTA, Protease inhibitor Complete (Roche), pH 7.4]. The cell suspension was homogenized 3 times using a polytron homogenizer at 20,000 rpm for 30 sec. The obtained homogenate was centrifuged (2,000 rpm, 10 min, 4° C.) using a low speed cooling centrifuge. The supernatant was recovered in an ultracentrifugation tube and ultracentrifuged (40,000 rpm, 60 min, 4° C.) using an ultracentrifuge (Beckman, L-90K). To the obtained pellets was added a suspending buffer [50 mM Tris-HCl, 1 mM EDTA, Protease inhibitor Complete (Roche), pH 7.4], and the pellets were suspended by pipetting. The protein concentration of this suspension was measured, diluted to 2 mg/mL to give cellular membrane fractions of CHO-hMelR7 and CHO-hMT2 cells. The membrane fractions were dispensed to 1.5 mL tubes (Eppendorf, #0030120.086) by 100 µL, preserved in a freezer (−80° C.) and used for a binding assay. Protein was quantified using BCA protein assay kit (Pierce) with BSA as the standard.

(4) Preparation of Membrane Fraction Suspension

Immediately before use, the membrane fractions of CHO-hMelR7 and CHO-hMT2 cells of the above-mentioned (3) were diluted 20-fold with assay buffer (50 mM Tris-HCl, pH 7.7).

(5) Preparation of 2-[$^{125}$I] Iodomelatonin Solution

2-[$^{125}$I] Iodomelatonin (#NEX236, PerkinElmer) was diluted with the assay buffer to 400 pM for $MT_1$ and 1 nM for $MT_2$.

(6) Binding Reaction

The assay buffer (80 µL) of the above-mentioned (4) was added to each well of a 96-well plate (type 3363, Corning). Then, a test compound (compound solution diluted with DMSO to 200-fold of the final measurement concentration) was added by 2 µL. 2 µL of DMSO was added to each well of the total binding control section, and 100 µM cold Melatonin solution (Sigma, diluted with DMSO to 100 µM) was added to each well of the nonspecific binding control section by 2 µL. Then, the membrane fraction suspension (100 µL) was added. 2-[$^{125}$I] Iodomelatonin solution of the above-mentioned (5) was added to each well mentioned above by 20 µL, and a binding reaction was carried out at 25° C. for 2.5 hr in a micromixer (TAITEC, Bioshaker M.BR-024).

(7) Measurement

Using a cell harvester (PerkinElmer), the binding reaction mixture in each well of the 96-well plate was transferred to a treated (immersed in 50 mM Tris, pH 7.7 in advance) filter plate (UniFilter GF/C, PerkinElmer) and filtered. After filtration, the plate was washed 4 times with the assay buffer, and dried in a dryer (42° C.) for 2 hr or more. 25 µL of a liquid scintillator (MicroScint O, PerkinElmer) was added to each well of the filter plate after drying, and the luminescence of scintillator was measured by TopCount (PerkinElmer) for 1 min.

Specific binding is a value obtained by subtracting nonspecific binding from the total binding. The binding inhibitory activity of the test compound is shown by the ratio of the value obtained by subtracting the measurement value when the test compound was added from the total binding, to the specific binding. The compound concentration ($IC_{50}$ value) showing 50% of binding inhibitory activity was calculated from the dose reaction curve.

The binding inhibitory activity of the compound of Examples 1, 2, 3, 5, 6, 7, 8, 11, 12, 14, 18, 19, 21, 22, 23, 24, 25, 28, 29, 30, 31, 32 and 33 was not more than 100 nM as $IC_{50}$ value for $MT_1$.

The binding inhibitory activity of the compound of Examples 1, 2, 3, 5, 6, 7, 8, 11, 12, 14, 18, 19, 21, 22, 23, 24, 25, 28, 29, 30, 31, 32, 33 and 34 was not more than 100 nM as $IC_{50}$ value for $MT_2$.

This application is based on application No. 2006-356344 filed in Japan, the contents of which are incorporated hereinto by reference.

The invention claimed is:
1. A compound represented by the formula:

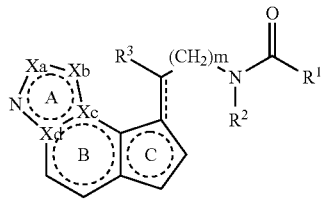
(I)

wherein
$R^1$ is $C_{1-6}$ alkyl or $C_{3-6}$ cycloalkyl,
$R^2$ is a hydrogen atom or $C_{1-6}$ alkyl,
$R^3$ is a hydrogen atom or $C_{1-6}$ alkyl,
m is 0, 1 or 2,
the tricycle of ring A, ring B and ring C is a ring represented by the formula

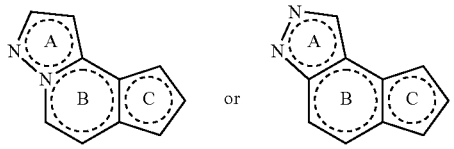

wherein ring A optionally has 1 or 2 substituents selected from the group consisting of a halogen atom, $C_{1-6}$ alkyl, $C_{6-10}$ aryl and $C_{1-6}$ alkoxy-carbonyl,
ring B optionally has one halogen atom, and
ring C is unsubstituted, and
------- is a single bond or a double bond,
or a salt thereof.

2. The compound of claim 1, wherein $R^1$ is $C_{1-6}$ alkyl.
3. The compound of claim 1, wherein $R^2$ is a hydrogen atom.
4. The compound of claim 1, wherein $R^3$ is a hydrogen atom.
5. The compound of claim 1, wherein m is 1.
6. The compound of claim 1, wherein
$R^2$ is a hydrogen atom;
$R^3$ is a hydrogen atom;
m is 1;
Xa is (1) CH optionally substituted by $C_{1-6}$ alkyl or $C_{6-10}$ aryl or (2) NH optionally substituted by $C_{1-6}$ alkyl; and
Xb is CH optionally substituted by a halogen atom, $C_{1-6}$ alkyl or $C_{1-6}$ alkoxy-carbonyl.
7. N-[2-(2-Methyl-6,7-dihydrocyclopenta[e]indazol-8(2H)-ylidene)ethyl]acetamide,
N-[2-(2-methyl-2,6,7,8-tetrahydrocyclopenta[e]indazol-8-yl)ethyl]acetamide,
N-[2-(2-methyl-2,6,7,8-tetrahydrocyclopenta[e]indazol-8-yl)ethyl]propanamide,
N-[2-(1-fluoro-2-methyl-2,6,7,8-tetrahydrocyclopenta[e]indazol-8-yl)ethyl]acetamide,
N-[2-(1-chloro-2-methyl-2,6,7,8-tetrahydrocyclopenta[e]indazol-8-yl)ethyl]acetamide,
N-[2-(5-fluoro-2-methyl-2,6,7,8-tetrahydrocyclopenta[e]indazol-8-yl)ethyl]acetamide,
N-[2-(5-chloro-2-methyl-2,6,7,8-tetrahydrocyclopenta[e]indazol-8-yl)ethyl]acetamide,
N-[2-(2-methyl-8,9-dihydro-7H-cyclopenta[c]pyrazolo[1,5-a]pyridin-9-yl)ethyl]acetamide, or
N-[2-(2-methyl-8,9-dihydro-7H-cyclopenta[c]pyrazolo[1,5-a]pyridin-9-yl)ethyl]propanamide,
or a salt thereof.

8. A pharmaceutical composition comprising the compound of claim 1 or a salt thereof, and a pharmacologically acceptable carrier.
9. The pharmaceutical composition of claim 8, which is a melatonin receptor agonist.
10. A compound represented by the formula

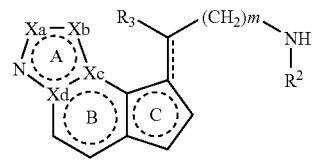

wherein
$R^2$ is a hydrogen atom or $C_{1-6}$ alkyl,
$R^3$ is a hydrogen atom or $C_{1-6}$ alkyl,
m is 0, 1 or 2,
the tricycle of ring A, ring B and ring C is a ring represented by the formula

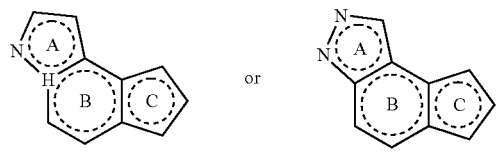

wherein ring A optionally has 1 or 2 substituents selected from the group consisting of a halogen atom, $C_{1-6}$alkyl, $C_{6-10}$ aryl and $C_{1-6}$ alkoxy-carbonyl,
ring B optionally has one halogen atom, and
ring C is unsubstituted, and
------- is a single bond or a double bond,
or a salt thereof.

* * * * *